(12) United States Patent
Wu et al.

(10) Patent No.: US 11,268,925 B2
(45) Date of Patent: Mar. 8, 2022

(54) INTERTWINED ELECTRICAL INPUT SIGNALS

(71) Applicant: ASCENSIA DIABETES CARE HOLDINGS AG, Basel (CH)

(72) Inventors: Huan-Ping Wu, Granger, IN (US); Mary Ellen Warchal-Windham, Osceola, IN (US); Bern Everett Harrison, Moscow, ID (US); Nicole D. Ellis, Edwardsburg, MI (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 470 days.

(21) Appl. No.: 16/316,589

(22) PCT Filed: Jul. 7, 2017

(86) PCT No.: PCT/IB2017/054133
§ 371 (c)(1),
(2) Date: Jan. 9, 2019

(87) PCT Pub. No.: WO2018/011692
PCT Pub. Date: Jan. 18, 2018

(65) Prior Publication Data
US 2019/0293594 A1    Sep. 26, 2019

Related U.S. Application Data

(60) Provisional application No. 62/430,232, filed on Dec. 5, 2016, provisional application No. 62/361,358, filed on Jul. 12, 2016.

(51) Int. Cl.
*G01N 27/327*  (2006.01)
*G01N 27/416*  (2006.01)
*G01N 33/487*  (2006.01)

(52) U.S. Cl.
CPC ....... *G01N 27/3274* (2013.01); *G01N 27/416* (2013.01); *G01N 33/48707* (2013.01)

(58) Field of Classification Search
None
See application file for complete search history.

(56) References Cited

U.S. PATENT DOCUMENTS 8,002,965 B2    8/2011  Beer
8,026,104 B2    9/2011  Wu
(Continued)

FOREIGN PATENT DOCUMENTS

CN    105378467 A    3/2016
EP    3 021 112 A1   5/2016
(Continued)

OTHER PUBLICATIONS

DR Thévenot, et al. "Electrochemical Biosensors: recommended definitions and classification" Pure and Applied Chemistry 71(12): p. 2333-2348, Jan. (Year: 1999).*

(Continued)

*Primary Examiner* — J. Christopher Ball
(74) *Attorney, Agent, or Firm* — Nixon Peabody LLP

(57) ABSTRACT

Devices and methods for determining one or more analyte concentrations in a sample, determining a sample type, and/or accounting for interference species in a sample are disclosed that include intertwining a first input signal, via a first electrode having a reagent, with a second input signal, via a second electrode lacking a reagent, by applying to the sample the first input signal having at least two excitations and a relaxation, and applying to the sample the second input signal having at least two excitations and a relaxation, such that the excitations of the first input signal are nonconcurrent with the excitations of the second input signal. The method further includes measuring a first output signal responsive to (Continued)

the first input signal and a second output signal responsive to the second input signal.

26 Claims, 45 Drawing Sheets

(56) References Cited

U.S. PATENT DOCUMENTS

| | | |
|---|---|---|
| 8,147,674 B2 | 4/2012 | Wu |
| 8,404,100 B2 | 3/2013 | Wu |
| 8,425,757 B2 | 4/2013 | Wu |
| 8,744,776 B2 | 6/2014 | Wu |
| 9,164,076 B2 | 10/2015 | Huang |
| 9,222,910 B2 | 12/2015 | Wu |
| 9,228,978 B2 | 1/2016 | Wu |
| 9,958,410 B2 | 5/2018 | Wu |
| 2008/0280376 A1 | 11/2008 | Handberg |
| 2009/0177406 A1 | 7/2009 | Wu |
| 2010/0267161 A1 | 10/2010 | Wu |
| 2011/0231105 A1 | 9/2011 | Wu |
| 2012/0095318 A1 | 4/2012 | Galley |
| 2013/0071869 A1 | 3/2013 | Wu |
| 2013/0116526 A1 | 5/2013 | Javitt |
| 2014/0027308 A1 | 1/2014 | Harrison |
| 2014/0138261 A1 | 5/2014 | Colas |
| 2016/0108451 A1 | 4/2016 | Fujiwara |
| 2017/0046501 A1 | 2/2017 | Coleman |

FOREIGN PATENT DOCUMENTS

| | | |
|---|---|---|
| WO | WO 2006/110504 | 10/2006 |
| WO | WO 2007/013915 | 2/2007 |
| WO | WO 2007/040913 | 4/2007 |
| WO | WO 2008/051742 | 5/2008 |
| WO | WO 2009/042631 | 4/2009 |
| WO | WO 2009/075951 | 6/2009 |
| WO | WO 2009/108239 | 9/2009 |
| WO | WO 2010/006253 | 1/2010 |
| WO | WO 2010/077660 | 7/2010 |
| WO | WO 2011/119533 | 9/2011 |
| WO | WO 2011/156152 | 12/2011 |
| WO | WO 2011/156325 | 12/2011 |
| WO | WO 2018/011692 | 1/2018 |

OTHER PUBLICATIONS

International Search Report in International Patent Application No. PCT/IB2017/054133, dated Dec. 1, 2017 (5 pages).
Written Opinion in International Patent Application No. PCT/IB2017/054133, dated Dec. 1, 2017, (10 pages).
International Search Report and Written Opinion of the International Patent Application No. PCT/IB2017/057584, dated Feb. 15, 2018 (11 pages).

\* cited by examiner

INTERTWINED ELECTRICAL INPUT SIGNALS

CROSS-REFERENCE TO RELATED APPLICATIONS

The present application is a national stage application under 35 U.S.C. § 371 of International Application No. PCT/IB2017/054133, filed on Jul. 7, 2017, entitled, "INTERTWINED ELECTRICAL INPUT SIGNALS," which claims the benefit of and priority to U.S. Provisional Application No. 62/361,358, filed Jul. 12, 2016, entitled, "INTERTWINED ELECTRICAL INPUT SIGNALS," and U.S. Provisional Application No. 62/430,232, filed Dec. 5, 2016, entitled, "INTERTWINED ELECTRICAL INPUT SIGNALS," each of which is hereby incorporated by reference herein in its entirety.

FIELD OF THE PRESENT DISCLOSURE

Aspects of the present disclosure relate generally to devices and methods for determining a concentration of an analyte in a sample.

BACKGROUND

Biosensor systems provide an analysis of a biological fluid, such as whole blood (WB), serum, plasma, urine, saliva, and interstitial or intracellular fluid. Typically, biosensor systems have a measurement device that analyzes a sample contacting a test sensor. The sample is typically in liquid form and, in addition to being a biological fluid, can be the derivative of a biological fluid, such as an extract, a dilution, a filtrate, or a reconstituted precipitate. The analysis performed by the system determines the presence and/or concentration of one or more analytes in the sample, such as alcohol, glucose, uric acid (UA), lactate, cholesterol, bilirubin (BRB), free fatty acids, triglycerides, proteins, ketones, phenylalanine, or enzymes. The analysis can be useful in the diagnosis and treatment of physiological abnormalities. For example, a diabetic individual may use a biosensor system to determine the glucose level in WB for adjustments to diet and/or medication.

In electrochemical biosensor systems, the analyte concentration is determined from an electrical signal generated by an oxidation/reduction (redox) reaction of the analyte, or a species responsive to the analyte, such as a measurable species, when an input signal is applied to the sample. The input signal can be a potential or current and can be constant, variable, or a combination thereof.

The measurement device applies an input signal to the working electrode of the test sensor, which conveys the input signal into the sample. The redox reaction of the measurable species generates an electrical output signal in response to the input signal. Specifically in the case of glucose, glucose is oxidized by an enzyme, which then transfers an electron to a mediator. The reduced mediator then travels to an electrode of the test sensor where it is electrochemically oxidized and generates an output signal. The measurement device can have the processing capability to measure and correlate the output signal with the presence and/or concentration of one or more analytes in the biological fluid.

Coulometry is one electrochemical method that has been used to quantify analytes in biological fluids. In coulometry, the analyte concentration is quantified by exhaustively oxidizing the analyte within a small volume and integrating the current over the time of oxidation to produce the electrical charge representing the analyte concentration. Thus, coulometry captures the total amount of analyte within the test sensor. An important aspect of coulometry is that towards the end of the integration curve of charge versus time, the rate at which the charge changes with time becomes substantially constant to yield a steady-state condition. The steady-state portion of the coulometric curve forms a relatively flat current region, thus allowing determination of the corresponding current. However, the coulometric method requires the complete conversion of the entire volume of analyte to reach the steady-state condition unless the true steady-state current is estimated from non-steady-state output. As a result, this method can be time consuming or less accurate due to the estimation. The sample volume of the test sensor also must be controlled to provide accurate results, which can be difficult with a mass-produced device.

Amperometry is another electrochemical method that has been used to quantify analytes in biological fluids. In amperometry, current is measured during a read pulse as a constant potential (voltage) is applied across the working electrode and the counter electrode of the test sensor. The measured current is used to quantify the analyte in the sample. Amperometry measures the rate at which the electrochemically active species, and thus the analyte, is being oxidized or reduced near the working electrode.

Voltammetry is another electrochemical method that can be used to quantify analytes in biological fluids. Voltammetry differs from amperometry in that the potential of the input signal applied across the working and counter electrodes of the test sensor changes continuously with time. The current is measured as a function of the change in potential of the input signal and/or time.

The measurement performance of a biosensor system is defined in terms of accuracy and/or precision. Increases in accuracy and/or precision provide for an improvement in measurement performance of the system, such as a reduction in the bias. Accuracy and error are opposite in describing the system performance. A more accurate reading means less error associated with the reading. Accuracy and error can be expressed in terms of bias of the system's analyte reading in comparison to a reference analyte reading, with larger bias values representing less accuracy. Precision can be expressed in terms of the spread or variance among multiple analyte readings in relation to a mean. Bias is the difference between one or more values determined from the biosensor system and one or more accepted reference values for the analyte concentration in the biological fluid. Thus, one or more error sources in the analysis results in the bias of the determined analyte concentration of a biosensor system. A competing consideration is the total time that elapses between the application of energy to the sample and the determination of analyte concentration. Shorter times may affect the accuracy and/or precision positively or negatively, but too short an assay time may compromise accuracy and/or precision.

Error can be expressed in terms of "absolute bias" or "percent bias" of the determined analyte concentration from the reference analyte concentration. Absolute bias can be expressed in the units of the measurement, such as milligrams per deciliter ($A_{Cal}-A_{Ref}$ mg/dL), while percent bias can be expressed as a percentage of the absolute bias value over the reference value ($100*[A_{Cal}-A_{Ref}]/A_{Ref}$), where A is the target analyte concentration. An example of expressing error can be found in the ISO standard of ISO 15197-2013E, where the error may be expressed in terms of absolute bias as being the glucose reading deviation from the reference glucose value ($G_{Cal}-G_{Ref}$) for glucose concentrations less than 100 mg/dL, while also expressed in terms of percent bias as being the glucose reading percent bias deviation from the reference glucose ($100*[G_{Cal}-G_{Ref}]/G_{Ref}$) for glucose concentrations at 100 mg/dL and higher. The term "combined bias" (expressed as bias/%-bias) represents absolute bias for glucose concentrations less than 100 mg/dL and percent bias for glucose concentrations of 100 mg/dL and higher. Under such an error definition, accuracy is further defined as how well the measured glucose readings are within a boundary of the combined biases (bias/% bias). For instance, ISO-2013E calls for 95% or greater of the data are within ±15 mg/dL/±15% of the reference glucose readings. It is the error boundary and the bias/%-bias that forms the basis of accuracy. The narrower the error boundary, the better the accuracy. Thus, a biosensor system having 95% or greater of the data within ±12.5 mg/dL/±12.5% is more accurate than that within ±15 mg/dL/±15%, while ±10 mg/dL/±10% is better than ±12.5 mg/dL/±12.5%, and ±5 mg/dL/±5% is better than ±10 mg/dL/±10%.

Measurement accuracy of an analyte concentration of interest may be affected by the presence of interference species within the sample. The interference species contribute to the output signal but are unrelated to the concentration of the analyte. In some cases, the interference species can affect the output signal based on directly affecting the redox reaction of the analyte. For example, when a biosensor system determines the concentration of a reduced mediator generated in response to the oxidation of an analyte, any reduced mediator generated not by oxidation of the analyte will lead to the biosensor system indicating that more analyte is present in the sample than is correct due to mediator background. In addition, an interference species can reduce the mediator, although the interference species is unrelated to the analyte. In the case of glucose, such an interference species can be xylose or another chemically similar species to glucose. In other cases, the interference species that have similar redox potentials as that of the analyte and/or the mediator, and that of the potential of an input signal applied to the sample, can be oxidized and/or reduced along with the analyte and/or the mediator and, therefore, contribute to the output signal. Interference species that do not directly affect the redox reaction of the analyte but still affect the output signal include, for example, ascorbic acid (ASA), UA, acetaminophen (AA), dopamine (Dop), and the like. The presence of one or more interference species and the inability or failure of conventional measurement systems to account for the contribution of these interference species in the analyte concentration measurement undesirably contributes to measurement inaccuracy of the analyte concentration of interest.

The concentration values obtained from an analysis with an error can be inaccurate. Thus, biosensor systems include one or more methods to correct the error, or reduce the bias, associated with an analysis. The ability to correct these analyses with error may increase the accuracy and/or precision of the concentration values obtained. An error correction system may compensate for effects from one or more error sources, such as error arising when the measurable species concentration does not correlate with the analyte concentration. For example, when a biosensor system determines the concentration of a reduced mediator generated in response to the oxidation of an analyte, any reduced mediator not generated by oxidation of the analyte will lead to the system indicating that more analyte is present in the sample than is correct due to mediator background. Thus, "mediator background" is the bias introduced into the measured analyte concentration attributable to measurable species not responsive to the underlying analyte concentration.

Measurement error or biases also may arise when the output signal does not correlate to the measurable species concentration of the sample. For example, when a biosensor system determines the concentration of a measurable species from output signal currents, output currents not responsive to the measurable species will lead to the system's indicating that more analyte is present in the sample than is correct due to interferent current. Thus, "interferent bias" is the bias introduced into the measured analyte concentration attributable to interferents producing output currents not responsive to the underlying analyte concentration.

The ability to correct these analyses may increase the accuracy and/or precision of the concentration values obtained. An error correction system may compensate for one or more error sources, such as a sample temperature or a sample hematocrit level, which are different from a reference temperature or a reference hematocrit value.

While conventional error compensation methods/systems attempt to balance various competing advantages and disadvantages, they are prone to measurement inaccuracies and suffer from performance shortcomings. Conventional systems usually are directed to detect and respond to a particular type of error, either temperature or hematocrit, for example. Such methods/systems typically do not have the ability to compensate for multiple error sources. These systems generally also lack the ability to alter the compensation for the error based on multiple output signals from a specific sample. Consequently, conventional biosensor systems may provide analysis results having determined analyte concentration values outside a desired measurement performance limit.

For at least the foregoing reasons, there is an ongoing need for electrochemical biosensor systems having improved measurement performance, especially those that may provide an increasingly accurate and/or precise determination of a biological analyte concentration without extending the analysis period and preferably reducing it. The systems, devices, and methods of the present disclosure overcome at least one of the disadvantages associated with conventional systems.

SUMMARY

Aspects of the present disclosure include apparatuses, systems, and methods related to the determination of a concentration of one or more analytes in a sample. The apparatuses, systems, and methods of the present disclosure apply intertwined input signals to the sample for determining the concentration of the analyte. The intertwined input signals are applied to the sample via a working electrode with one or more reagents and a bare electrode without the one or more reagents. The first input signal includes at least two excitations and at least one relaxation, and the second input signal includes at least one excitation and at least one relaxation, where the excitations of the first and second input signals are nonconcurrent and where the excitations of one of the input signals are separated from each other by at least one excitation of the other input signal.

Aspects of the present disclosure include apparatuses, systems, and methods for measuring one or more output signals in response to the above-intertwined input signals for determining the concentration of the one or more analytes in the sample.

Aspects of the present disclosure include apparatuses, systems, and methods for measuring one or more output signals in response to the above-intertwined input signals for determining the type of the sample, which can include a determined specific type of the sample. In certain aspects, the types can be a control and a WB sample. In some aspects, the determined specific type among one type can be specific or predetermined controls.

Aspects of the present disclosure include apparatuses, systems, and methods for measuring one or more output signals in response to the above-intertwined input signals for determining one or more interference species in the sample, a level of interference of the sample, or a combination thereof. In certain aspects, the functionality and/or operation of the apparatuses, systems, and methods can vary based on the determination of the one or more interference species in the sample, the level of interference of the sample, or a combination thereof.

Further aspects of the present disclosure include a method of determining a concentration of an analyte in a sample. The method includes intertwining a first input signal, via a first electrode having a reagent, with a second input signal, via a second electrode lacking a reagent. The intertwining includes applying to the sample, via the first electrode, the first input signal having at least two excitations and a relaxation, and applying to the sample, via the second electrode, the second input signal having at least two excitations and a relaxation, such that the excitations of the first input signal are nonconcurrent with the excitations of the second input signal. The method further includes measuring a first output signal responsive to the first input signal and a second output signal responsive to the second input signal. The method further includes determining the concentration of the analyte based on at least the first output signal and the second output signal.

Aspects of the present disclosure also include a method of determining a concentration of an analyte in a sample. The method includes intertwining a first input signal via a first electrode having a reagent with a second input signal via a second electrode lacking any reagent. The intertwining includes applying to the sample, via the first electrode, the first input signal having at least two voltage pulses, and applying to the sample, via the second electrode, the second input signal having at least two voltage pulses, such that the at least two voltage pulses of the first input signal are separated by at least one voltage pulse of the at least two voltage pulses of the second input signal. The method further includes measuring a first output signal responsive to the first input signal and a second output signal responsive to the second input signal. The method further includes determining the concentration of the analyte based on at least the first output signal and the second output signal.

Additional aspects of the present disclosure include a method of determining a concentration of an analyte in a sample. The method includes applying a first input signal to the sample. The first input signal includes a first plurality of duty cycles. Each duty cycle of the first plurality of duty cycles includes: (i) an excitation between a first electrode and a counter electrode, and (ii) a relaxation of the first electrode. The first electrode includes at least one reagent that facilitates oxidation of the analyte. The method further includes applying a second input signal to the sample. The second input signal includes a second plurality of duty cycles. Each duty cycle of the second plurality of duty cycles includes: (i) an excitation between a second electrode and the counter electrode, and (ii) a relaxation of the second electrode, the second electrode excluding the at least one reagent. The method further includes measuring a first output signal responsive to the first input signal and a second output signal responsive to the second input signal. The method further includes determining the concentration of the analyte in the sample based on the first output signal and the second output signal. In aspects of the method, at least the excitations of the first plurality of duty cycles and the second plurality of duty cycles are intertwined.

Further aspects of the present disclosure include a method of determining a concentration of an analyte in a sample. The method includes applying a first input signal to the sample. The first input signal includes a first plurality of duty cycles. Each duty cycle of the first plurality of duty cycles includes: (i) a voltage pulse applied between a first electrode and a counter electrode, and (ii) a relaxation of the first electrode. The first electrode includes at least one reagent that facilitates oxidation of the analyte. The method further includes applying a second input signal to the sample. The second input signal includes a second plurality of duty cycles. Each duty cycle of the second plurality of duty cycles includes a voltage pulse applied between a second electrode and the counter electrode, where the second electrode excludes any reagent that facilitates oxidation of the analyte. The method further includes measuring a first output signal responsive to the first input signal and a second output signal responsive to the second input signal. The method further includes determining the concentration of the analyte in the sample based on the first output signal and the second output signal. Aspects of the method include each voltage pulse applied between the first electrode and the counter electrode of the first input signal being separated from a next voltage pulse applied between the first electrode and the counter electrode of the first input signal by at least one voltage pulse applied between the second electrode and the counter electrode of the second input signal.

Still further aspects of the present disclosure include a method of analyzing a solution with a blood glucose monitoring device. The method includes applying an input signal to the solution via a bare electrode of the blood glucose monitoring device, where the input signal includes a constant voltage pulse, such as a direct current (DC) voltage. The method further includes determining a polarity of a current generated in response to the voltage pulse. The method further includes identifying the solution as a control or a blood sample based, at least in part, on the polarity of the current.

Additional aspects of the present concepts include a method of determining a type of a sample. The method includes applying an input signal to the sample via a bare electrode, where input signal includes at least two excitations and a relaxation. The method further includes measuring an output signal responsive to the input signal, and determining one or more parameters based on the output signal. The method further includes comparing the one or more parameters to one or more thresholds to determine the type of the sample.

Further aspects of the present concepts include a method of accounting for one or more interference species in a sample. The method includes intertwining a first input signal, via a first electrode having a reagent, with a second input signal, via a second electrode lacking a reagent. The intertwining includes applying to the sample, via the first electrode, the first input signal having at least two excitations and a relaxation, and applying to the sample, via the second electrode, the second input signal having at least two excitations and a relaxation, such that the excitations of the first input signal are nonconcurrent with the excitations of the second input signal. The method further includes measuring a first output signal responsive to the first input signal and a second output signal responsive to the second input signal. The method further includes determining a level of interference of the one or more interference species in the sample based, at least in part, on the second output signal.

Additional aspects of the present concepts include a method of interference management. The method includes sorting one or more signals and/or one or more parameters to separate interference data from normal data so as to define boundaries by thresholds in one, two, or more dimensions. The method further includes determining whether to apply normal calculation/compensation to data, special calculation/compensation to the data, or reject the data based on the defined boundaries.

Still additional aspects of the present concepts include a method of determining a concentration of an analyte in a sample. The method includes intertwining a first input signal, having two or more excitations and at least one relaxation of a first electrode having a reagent specific to the analyte, with a second input signal, having one or more excitations and at least one relaxation of a second electrode lacking a reagent specific to the analyte, such that each excitation of the two or more excitations of the first input signal are nonconcurrent with the one or more excitations of the second input signal. The method further includes measuring a first output signal responsive to the first input signal and a second output signal responsive to the second input signal. The method also includes determining the concentration of the analyte based on at least the first output signal and the second output signal.

Yet additional aspects of the present concepts include a method of managing interference effects for one or more interference species in a sample. The method includes applying one or more input signals to a biosensor system in contact with an analyte sample. The method further includes measuring one or more output signals of the biosensor system responsive to the one or more input signals. The method also includes determining a position of a data point in a pre-sort separation map based on one or more signals, one or more parameters, or a combination thereof relative to defined boundaries of pre-set threshold values. The method further includes determining whether to apply a normal calculation/compensation of analyte concentration to the data point, a special calculation/compensation of analyte concentration to the data point, or a rejection of the data point based on the position.

Further aspects of the present disclosure include a method of providing sample profiles. In particular, the method includes determining an analyte concentration, such as glucose, as well as reporting one or more parameters about, or concentrations of, the endogenous species within the sample. Endogenous species (chemical substances that are present naturally in the human body) include uric acid, dopamine, cholesterol, or even the %-hematocrit, etc. as part of the WB sample. Over a period of time, this sample profiling will provide data in more than one dimension, which can lead to additional therapeutic actions to address the long term health and diabetes concerns.

Aspects of the present disclosure further include one or more apparatuses and systems configured to perform or execute the methods described above. In some aspects, the one or more apparatuses and one or more components of the systems include computer-readable instructions that cause the apparatuses and the one or more components to execute operations of the methods described above.

Additional aspects of the present disclosure will be apparent to those of ordinary skill in the art in view of the detailed description of various embodiments, which is made with reference to the drawings, a brief description of which is provided below.

Figure 1:
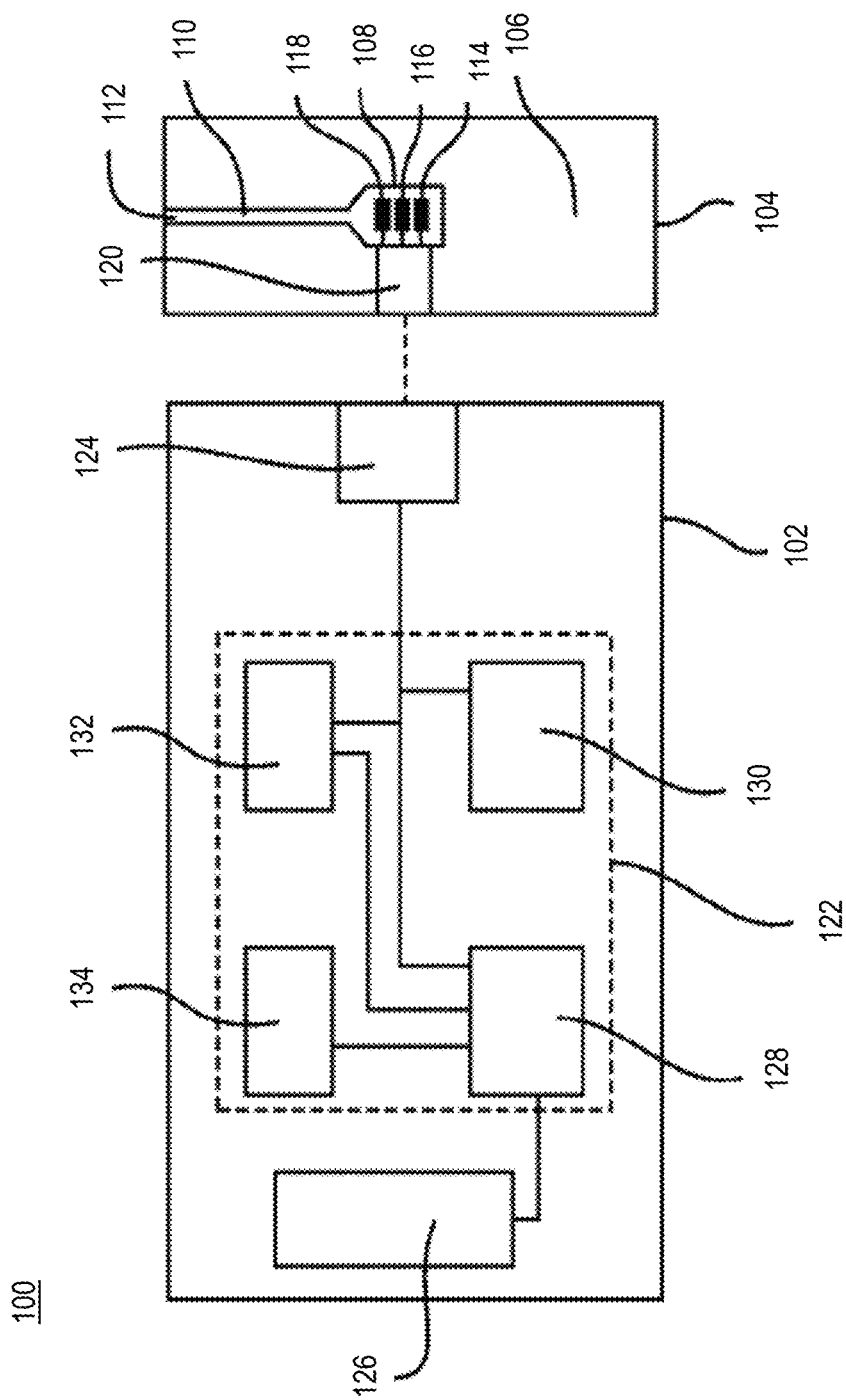
FIG. 1 depicts a schematic representation of a biosensor system that determines an analyte concentration in a sample of a biological fluid, in accord with aspects of the present disclosure.

The present disclosure is susceptible to various modifications and alternative forms, and some representative embodiments have been shown by way of example in the drawings and will be described in detail herein. It should be understood, however, that the disclosure is not intended to be limited to the particular forms illustrated and described. Rather, the present application covers all modifications, equivalents, and alternatives falling within the spirit and scope of the present disclosure, as further defined by the appended claims.

DETAILED DESCRIPTION

While this disclosure is susceptible of embodiment in many different forms, there is shown in the drawings and will herein be described in detail example implementations of the inventions and concepts herein with the understanding that the present disclosure is to be considered as an exemplification of the principles of the inventions and concepts and is not intended to limit the broad aspect of the disclosed implementations to the examples illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." For purposes of the present detailed description and accompanying figures, terms defined below and used throughout that include numbers separated by commas or numbers separated by hyphens, but otherwise identical, refer to the same term and such notations are interchangeable. For example, $i_{G1,1}$ is identical in meaning to $i_{G1-1}$, as further discussed below and as shown in the figures.

The bare or second electrode, as described and used herein, can be an electrode without any added reagent chemistry, or with one or more added inert materials. The bare electrode can also include added reagent chemistry that is not for the target analyte, in contrast to the working or first electrode described throughout as having reagent chemistry for the target analyte.

Relaxation, as described and used herein, can mean that the electrode of interest has no input signal for excitation, such as in the case of an open circuit. Relaxation can also mean that the biosensor system, as a whole, has no input signal for all electrodes. During intertwining, one electrode can be in relaxation while the other electrode is in excitation, and vice versa. However, the biosensor system cannot be in relaxation until both electrodes (or all electrodes, in the case of more than two electrodes) are in relaxation. For the working electrode having added reagent chemistry for the target analyte, as discussed in detail below, the relaxation for that particular electrode is the incubation time where the measureable species is generated from the enzyme activated chemical reaction without external influence, such as the electrochemical reaction. For the working electrode having no added reagent chemistry for the target analyte, as discussed in detail below, the relaxation time of the electrode is when all electrochemically active species (oxidizable and reducible) replenish by diffusion to a depletion layer during the input of an signal to the electrode.

FIG. 1 depicts a schematic representation of a biosensor system 100 that determines an analyte concentration in a sample of a biological fluid, in accord with aspects of the present disclosure. The biosensor system 100 includes a measurement device 102 and a test sensor 104, which can be implemented in any analytical instrument, including a bench-top device, a portable or hand-held device, or the like. The measurement device 102 and the test sensor 104 can be adapted to implement an electrochemical sensor system or the like. The biosensor system 100 adjusts one or more correlations for determining an analyte concentration of a sample based on parameters, such as one or more error parameters, generated in response to intertwined input signals applied to the sample. As explained in more detail below, the adjusted correlations based on the intertwined input signals improve the measurement performance of the biosensor system 100, for accuracy or speed or both, in determining the analyte concentration of the sample.

The biosensor system 100 can be utilized to determine concentrations of one or more various analytes within a sample, including one or more of glucose, UA, lactate, cholesterol, BRB, and the like. While a particular configuration is shown, the biosensor system 100 can have other configurations, including those with additional components, without departing from the spirit and scope of the present disclosure.

The test sensor 104 has a base 106 that forms a reservoir 108 and a channel 110 with an opening 112. The reservoir 108 and the channel 110 can be covered by a lid with a vent. Alternatively, the reservoir can be covered with a spacer and a lid with a vent. The reservoir 108 defines a partially-enclosed volume. The reservoir 108 can contain a composition that assists in retaining a liquid sample, such as water-swellable polymers or porous polymer matrices. The test sensor 104 can have other configurations without departing from the spirit and scope of the present disclosure. The test sensor 104 can be configured to analyze, for example, a single drop of WB, such as from 1-15 microliters (µL) in volume. In use, a liquid sample for analysis is transferred into the reservoir 108 by introducing the liquid to the opening 112. The liquid sample flows through the channel 110, filling the reservoir 108 while expelling the previously contained air.

The test sensor 104 includes at least three electrodes, namely a working electrode 114, a counter electrode 116, and a bare electrode 118. However, in some aspects, the test sensor 104 can include a different number of electrodes, such as more than three electrodes, including more than one working electrode 114, more than one counter electrode 116, and/or more than one bare electrode 118. By way of example, and without limitation, the test sensor 104 can include two counter electrodes 116, with the two counter electrodes 116 separately paired with the working electrode 114 and the bare electrode 118.

The working electrode 114 can include one or more reagents, such as one or more enzymes, binders, mediators, and like species. One or more of the reagents react with and transfer electrons from the analyte during the analysis and, thus, facilitate in the redox reaction of an analyte within the sample. The measurement device 102 can then measure and record the electrons as current and/or voltage passing through the test sensor 104, and translate the current and/or voltage into a measure of the analyte concentration of the sample.

An enzyme or similar species included with the reagents enhances the electron transfer from a first species to a second species during the redox reaction. The enzyme or similar species may react with the analyte, thus providing specificity to a portion of the generated output signal. A mediator can be used to maintain the oxidation state of the enzyme. Thus, in the case of the working electrode 114 with the enzyme and the mediator, the working electrode 114 is where the analyte undergoes electrochemical reaction. The counter electrode 116 is where the opposite electrochemical reaction occurs, which allows current to flow between the working electrode 114 and the counter electrode 116. Thus, if oxidation occurs at the working electrode 114, reduction occurs at the counter electrode 116.

Table 1 below provides non-limiting combinations of enzymes and mediators for use with specific analytes, where MLB is 3-(2',5'-phenylimino)-3H-phenothiazinedisulfonic acid.

TABLE 1

Analyte, enzyme, and mediator combinations

| Analyte | Enzyme | Mediator |
| --- | --- | --- |
| Glucose | Glucose Oxidase | Ferricyanide |
| Glucose | Glucose Dehydrogenase | Ferricyanide/MLB |
| Cholesterol | Cholesterol | Ferricyanide |
| Lactate | Lactate Oxidase | Ferricyanide |
| UA | Uricase | Ferricyanide |
| Alcohol | Alcohol Oxidase | Phenylenediamine |

The binder included with the reagent can include various types and molecular weights of polymers, such as carboxyl methyl cellulose (CMC), HEC (hydroxyl ethyl cellulose), and/or polyethylene oxide (PEO). In addition to binding the reagents together, the binder may assist in filtering red blood cells, preventing or inhibiting them from coating the surface of the working electrode 114, such as in the case of a blood glucose monitoring device.

In contrast, the bare electrode 118 does not include the one or more reagents that facilitate in the redox reaction of an analyte that is the focus of the biosensor system. Thus, although described as "bare," the bare electrode 118 merely does not include the same or identical one or more reagents that facilitate in the redox reaction of the analyte that are included on the working electrode 114. The bare electrode 118 can include other reagents that facilitate in the redox reaction of other species within the sample, besides the analyte of interest. Alternatively, the bare electrode 118 can merely be a bare conductor without any reagent whatsoever thereon or therein.

The bare electrode 118 can be arranged upstream from the working electrode 114 so that the effects of the one or more reagents on the working electrode 114 do not affect, or have minimal effect on, the electrical responses of the bare electrode 118. Alternatively, in some aspects, the working electrode 114 and the bare electrode 118 can be arranged in separate reservoirs 108 with substantial chemical isolation. Accordingly, the analyte that is the focus of the concentration determination of the biosensor system 100 responds to a current or voltage applied to the working electrode 114 based on the working electrode 114 having the one or more reagents. The analyte does not respond, or responds minimally, to a current or voltage applied to the bare electrode 118 based on the bare electrode 118 not having the one or more reagents.

The electrodes 114-118 can be substantially in the same plane or in more than one plane. The electrodes 114-118 can be disposed on a surface of the base 106 that forms the reservoir 108. The electrodes 114-118 can extend or project into the reservoir 108.

The test sensor 104 further includes a sample interface 120 that has conductors connected to the working electrode 114, the counter electrode 116, and the bare electrode 118. An output signal, such as a first output signal or a working output signal, can be measured from one or both of the conductors connected to the working electrode 114 and the counter electrode 116. Another output signal, such as a second output signal or a bare output signal, can be measured from one or both of the counter electrode 116 and the bare electrode 118.

The measurement device 102 includes electrical circuitry 122 connected to a sensor interface 124 and a display 126. The electrical circuitry 122 includes a processor 128 connected to a signal generator 130, an optional temperature sensor 132, and a storage medium 134. The display 126 can be analog or digital. The display 126 can include an LCD (liquid crystal display), an LED (light emitting device), an OLED (organic light emitting device), a vacuum fluorescent, electrophoretic display (ED), or other display adapted to show a numerical reading. Other electronic displays can be used. The display 126 electrically communicates with the processor 128. The display 126 can be separate from the measurement device 102, such as when in wireless communication with the processor 128. Alternatively, the display 126 can be removed from the measurement device 102, such as when the measurement device 102 electrically communicates with a remote computing device, medication dosing pump, and the like.

The signal generator 130 provides one or more electrical input signals to the sensor interface 124 in response to the processor 128. The electrical input signals can be transmitted by the sensor interface 124 to the sample interface 120 to apply the electrical input signals to the sample of the biological fluid. The electrical input signals can be a potential or a current and can be constant, variable, or a combination thereof, as further described below. The electrical input signals can be applied as a single pulse or in multiple pulses, sequences, or cycles. As discussed in detail below, the electrical input signals are preferably applied in multiple intertwined pulses. The signal generator 130 also can record one or more output signals from the sensor interface 124 as a generator-recorder.

The optional temperature sensor 132 determines the temperature of the biosensor system, including the device and the sample in the reservoir 108 of the test sensor 104. The temperature of the sample can be measured, calculated from the output signal, or assumed to be the same or similar to a measurement of the ambient temperature or the temperature of a device implementing the biosensor system 100. The temperature can be measured using a thermistor, thermometer, or other temperature sensing device. Other techniques can be used to determine the sample temperature.

The storage medium 134 can be a magnetic, optical, or semiconductor memory, another electronic storage device, or the like. The storage medium 134 can be a fixed memory device, a removable memory device, such as a memory card, remotely accessed, or the like.

The electronic processor 128 implements the analyte analysis and data treatment using computer-readable software code and data stored in the storage medium 134. The processor 128 can start the analyte analysis in response to the presence of the test sensor 104 at the sensor interface 124, the application of a sample to the test sensor 104, in response to user input, or the like. The processor 128 directs the signal generator 130 to provide the electrical input signals to the sensor interface 124. The processor 128 receives the output signals from the sensor interface 124. At least some of the output signals are generated in response to the input signals applied to the sample. Other output signals can be generated based on other characteristics, such as the temperature of the sample. In response to the output signals, the processor 128 adjusts one or more correlations for determining an analyte concentration.

More specifically, any system or method disclosed herein, including the biosensor system 100, can determine a concentration of an analyte within a sample by adjusting one or more analyte concentration correlations based on one or more error parameters, one or more predictor functions, one or more index functions, including one or more complex index functions, and the like extracted and/or generated from an output signal, such as disclosed in U.S. Pat. No. 9,164,076, filed May 27, 2011, entitled "Slope-Based Compensation Including Secondary Output Signals," U.S. Pat. No. 8,744,776, filed Jun. 6, 2011, entitled "Method for Determining Analyte Concentration Based on Complex Index Functions," International Application No. PCT/US2009/067150, filed Dec. 8, 2009, entitled, "Biosensor System With Signal Adjustment," and International Application No. PCT/US2008/085768, filed Dec. 6, 2008, entitled, "Slope-Based Compensation."

As discussed in the above-three references, the %-bias in the correlation of analyte concentrations with output signals can be represented by one or more slope deviations obtained from one or more error parameters. Error containing portions of output signals are reflected in the deviation between the hypothetical slope of the output signals and the slope of a reference correlation. By determining one or more values reflecting this deviation in slope from one or more error parameters, the measurement performance of an analysis can be improved. Predictor functions, index functions, and/or complex index functions correspond to the %-bias in the correlation between the analyte concentrations and the output signals due to one or more errors in the analysis.

Predictor functions generate correction values to compensate for error from one or more error sources to determine the target analyte concentration in the analyte concentration analysis. Such error can result in bias of the determined analyte concentrations. One or more predictor functions can be used. A predictor function that perfectly correlates with the total slope deviation would provide an ultimate total error compensation of the analyte concentration. Such a hypothetical, perfectly correlated predictor function could be used to compensate for all errors in the analysis without having to know the exact cause of the total slope deviation and, thus, the bias of the measured analyte concentration. Predictor functions include at least one index function, and one or more of the index functions can be complex.

An index function is responsive to at least one error parameter. An index function can be a calculated number that correlates with an error parameter and represents the influence of this error parameter on bias. Index functions can be experimentally determined as a regression or other equation representing the relationship between the deviation from a reference slope and the error parameter. Thus, the index function represents the influence of the error parameter on the slope deviation. Complex index functions include combinations of terms modified by weighting coefficients. The terms included in the complex index function can be selected with one or more exclusion tests.

Error parameters are responsive to error from one or more error sources in the output signal. Error parameters can be values from the analysis of the analyte, such as the one or more output signals, one or more portions of the output signals, or from other signals independent of the output signals, such as from thermocouple currents or voltages, and the like. Thus, the error parameters can be extracted directly or indirectly from the output signals. Any error parameter can be used to form the term or terms that make up the index function.

Slope deviations can be normalized to reduce the statistical effect of changes in the output signals, improve the differentiation in variations of the output signals, standardize the measurements of the output signals, a combination thereof, or the like. Since the slope deviation can be normalized, an index function also can be expressed in terms of the normalized slope deviation as a function of error parameters as generated from a multi-variable regression. In normalization, the slope deviation, index function, or other parameter is adjusted (multiplied, divided, or the like) by a variable to reduce the statistical effect of changes in the parameter, improve the differentiation in variations of the parameter, standardize measurements of the parameter, a combination thereof, or the like. The greater the correlation between a predictor or index function, and slope deviation, the better the function is at correcting error in the analysis.

An index function is complex when the function includes a combination of terms modified by weighing coefficients. The combination is preferably a linear combination, but other combination methods can be used that provide weighing coefficients for the terms. Each term can include one or more error parameters.

Applying the intertwined input signals to a test strip through a biosensor system provides information about the target analyte concentration, and also information about the target analyte in relation to the sample types, sample profiles, and/or sample environments in terms of potential interference species, endogenous species, and their interactions with the target analyte.

Figure 2A:
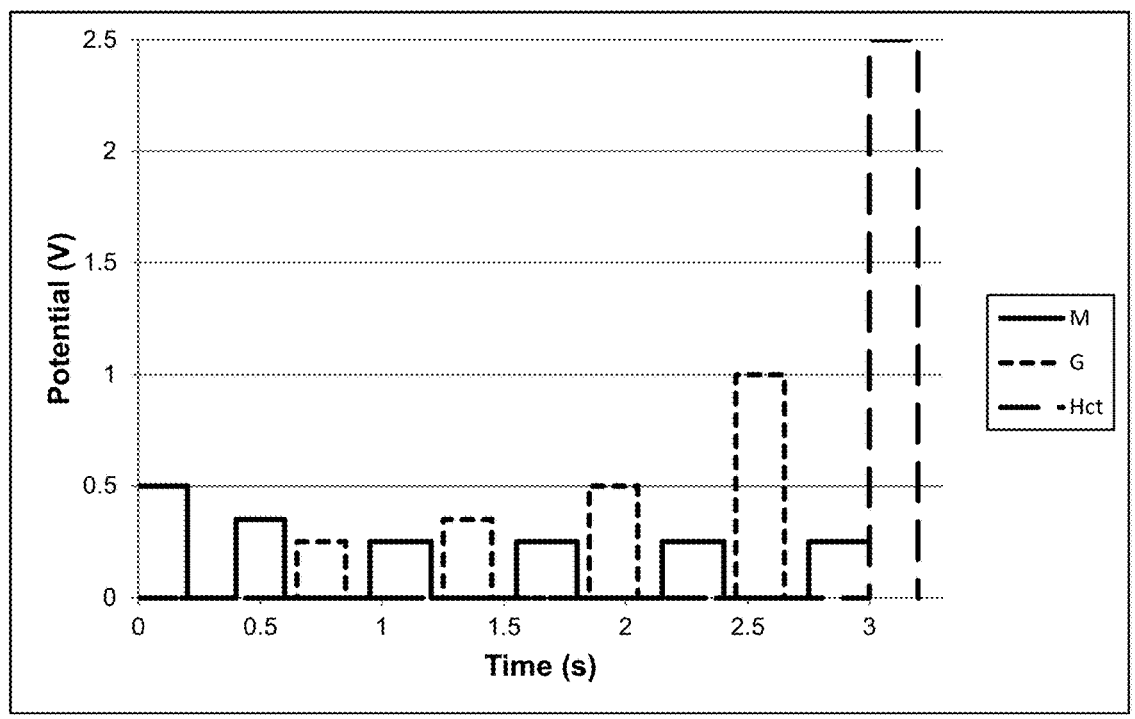
FIG. 2A is a graph illustrating an application of intertwined input signals for a biosensor system, in accord with additional aspects of the present disclosure.
Figure 2B:
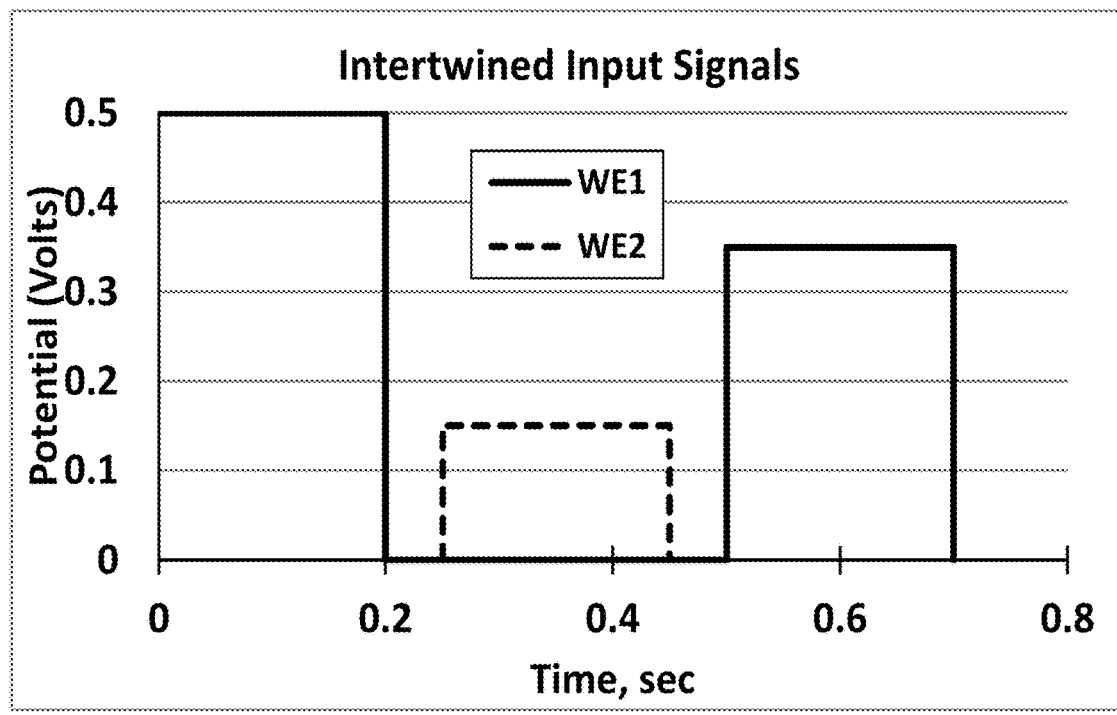
FIG. 2B is a graph illustrating an alternative application of intertwined input signals for a biosensor system, in accord with additional aspects of the present disclosure.
Figure 2C:
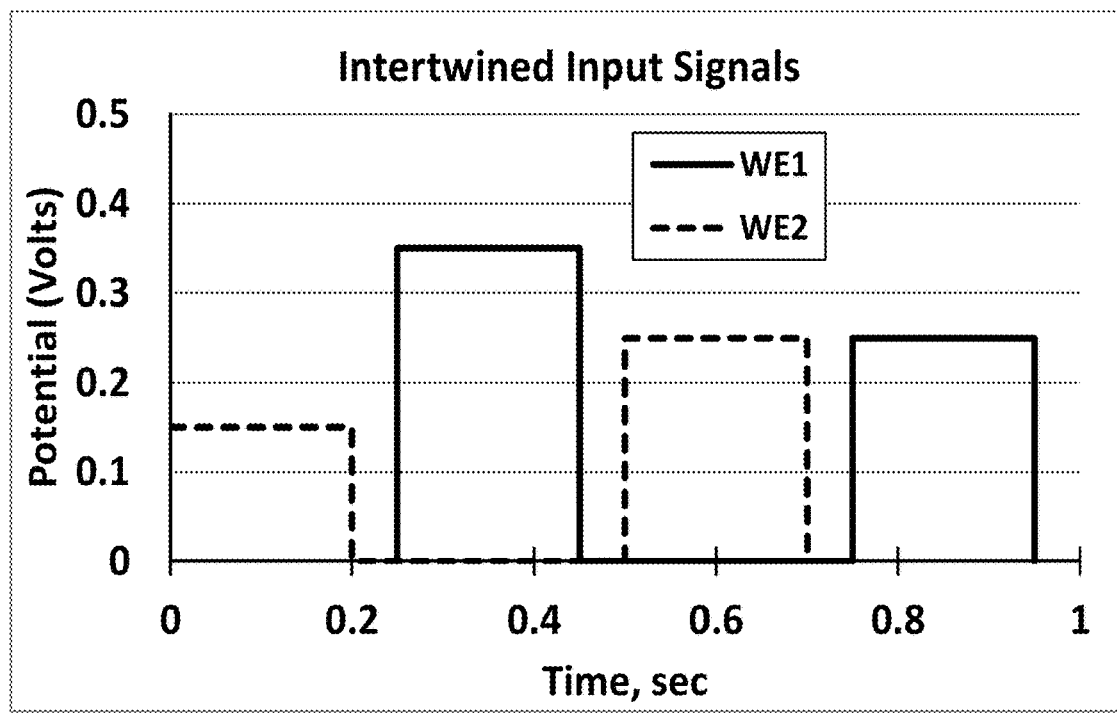
FIG. 2C is a graph illustrating an alternative application of intertwined input signals for a biosensor system, in accord with additional aspects of the present disclosure.

FIGS. 2A-2C are graphs illustrating exemplary intertwined input signals for an electrochemical biosensor system, such as the system 100 of FIG. 1, in accord with aspects of the present disclosure. More specifically, FIG. 2A shows three input signals, represented by the labels M, G, and Hct.

As described in relation to the biosensor system 100 of FIG. 1, the first input signal M includes electrical pulses (or simply pulses) of constant potential (voltage) applied across the working electrode 114 and the counter electrode 116. However, the first input signal can be applied to any biosensor system with a working electrode and a counter electrode as described herein. In some aspects, the first input signal can be described as a working input signal based on the signal being applied to the sample via the working electrode 114.

As shown, the first input signal M includes six pulses, which will be referred to here in the order in which they appear from left to right on the graph as $M_1$, $M_2$, $M_3$, $M_4$, $M_5$, and $M_6$. The pulse $M_1$ has a potential of 0.5 volt (V), the pulse $M_2$ has a potential of 0.35 V, and the remaining pulses $M_3$ to $M_6$ have potentials of 0.25 V. Because the pulses of the first input signal M are applied via the working electrode 114 with the one or more reagents, the pulses of the first input signal M probe the analyte in the sample, either directly or indirectly through a mediator or other measureable species.

The second input signal G also includes pulses of constant potential. However, as described in relation to the biosensor system 100 of FIG. 1, the pulses of the second input signal G are applied across the bare electrode 118 and the counter electrode 116. However, the second input signal can be applied to any biosensor system with a bare electrode and a counter electrode as described herein. In some aspects, the second input signal can be described as a bare input signal because the second input signal is applied via the bare electrode 118.

As shown, the second input signal G includes four pulses, which will be referred to here in the order in which they appear from left to right on the graph as $G_1$, $G_2$, $G_3$, and $G_4$. The pulse $G_1$ has a potential of 0.25 V, the pulse $G_2$ has a potential of 0.35 V, the pulse $G_3$ has a potential of 0.5 V, and the pulse $G_4$ has a potential of 1.0 V. Because the bare electrode 118 does not include one or more reagents that are responsive to the target analyte within the sample, the pulses of the second input signal G applied via the bare electrode 118 do not probe the target analyte targeted by the working electrode 114 in the sample. Instead, the pulses of the second input signal G applied via the bare electrode 118 probe the other species in the sample across the electrochemical detection window, including potential interference species in the sample as described in further detail below. Thus, measurements based on the bare electrode 118 are sensitive mostly to other oxidizable species at various potentials and not the target analyte being analyzed by the first input signal M and the working electrode 114. The resulting measurements in response to the second input signal applied via the bare electrode 118 could otherwise be incorrectly measured as contributions to the enzyme reaction at the working electrode 114, despite the resulting measurements not being related to the concentration of the analyte. Accordingly, analysis of and error parameters based on the second input signal G, alone or in combination with analysis of and error parameters based on the first input signal M, allow for compensation of the determination of the concentration of the analyte that previously could not take into account the entire electrochemical detection window.

The third input signal Hct is a single pulse for determining the hematocrit level of the sample, in the case of a WB sample. As described in relation to the biosensor system 100 of FIG. 1, the single pulse of the third input signal Hct is a constant voltage of 2.5 V applied across the bare electrode 118 and the combination of the counter electrode 116 and the working electrode 114. Alternatively, the single pulse of the third input signal Hct instead can be applied across the bare electrode 118 and the counter electrode 116, with the working electrode 114 in an open state. Although described as three separate input signals, the second input signal and the third input signal can instead be considered as a single input signal, such as the second input signal including the pulses $G_1$-$G_4$ and the pulse Hct for determining the hematocrit level.

As shown, the pulses of the first and second input signals are nonconcurrent (e.g., the first and second signals are not maximally energized at the same time, or no maximum voltage of the first input signal overlaps any maximum voltage of the second input signal). Moreover, each pulse of the first input signal is separated by the next pulse of the first input signal by a pulse of the second input signal. Based on the pulses of the first and second input signals being nonconcurrent, and a pulse of the second input signal separating the pulses of the first input signal, the pulses of the first and second input signals are described as being intertwined.

When not applying a voltage pulse, the working electrode 114 and the bare electrode 118 can be in an open circuit state. Thus, during pulses of the first input signal, the bare electrode 118 can be in an open circuit state, and during pulses of the second input signal, the working electrode 114 can be in an open circuit state.

As shown, each pulse of the first and second input signals is followed by an electrical relaxation, or simply a relaxation. Specifically, each pulse of the first input signal is immediately followed by a relaxation, such as no input potential (or open circuit), for the first input signal, and each pulse of the second input signal is immediately followed by a relaxation, such as zero potential (or open circuit), for the second input signal. The periods between pulses of the same input signal can be considered relaxations of that particular signal. The periods between pulses of all input signals, i.e., where there is no pulse, can be considered relaxations of the system 100. Thus, after a pulse of the first input signal is a relaxation of the first input signal until the next pulse of the first input signal. As shown in FIG. 2A, after a pulse of the first input signal is a relaxation of the system until the next pulse of the second input signal. The combination of a pulse followed by a relaxation within the first or second input signal can be a duty cycle. The first and second input signals, therefore, can include a plurality of duty cycles of pulses followed by relaxations.

Although described as the working electrode 114 or the bare electrode 118 being in an open state during a relaxation, or having a zero potential applied across the working electrode 114 and/or bare electrode 118, the relaxations of the working electrode 114 and the bare electrode 118 do not require that the electrodes 114 and 118 be in an open state. In some aspects, a current passing through the working electrode 114 and the bare electrode 118 can be at least half as much current as in a closed state and still be considered in a relaxation period. Alternatively, a working or bare electrode can be considered to be in a relaxation period or state when the potential applied to the electrode is lower than a redox potential of the target analyte or species, as the case may be. Alternatively, a working or bare electrode can be considered to be in a relaxation period or state when the current is reduced to at least one-half the current flow at the excitation maxima or by at least an order of magnitude in relation to the current flow at the excitation maxima.

Each pulse, as well as each relaxation, has a width, also referred to as a pulse width and a relaxation width, respectively. A pulse and relaxation pair defines a duty cycle. For each duty cycle, the pulse and relaxation widths combined are a duty cycle width or duty cycle period. The pulse widths for the pulses of the first input signal can all have the same width, can all have different widths, or can have combinations of the same and different widths. Similarly, the relaxation widths for the relaxations of the first input signal can all have the same width, can all have different widths, or can have combinations of the same and different widths. The pulse widths and the relaxation widths of the duty cycles of the first input signal can be the same width or can be different widths. In addition, the widths or periods of the duty cycle of the first input signal can be the same width or be different widths.

Similarly, the pulse widths for the pulses of the second input signal can all have the same width, can all have different widths, or can have combinations of the same and different widths. Similarly, the relaxation widths for the relaxations of the second input signal can all have the same width, can all have different widths, or can have combinations of the same and different widths. The pulse widths and the relaxation widths of the duty cycles of the second input signal can be the same width or can be different widths. In addition, the widths or periods of the duty cycle of the second input signal can be the same width or be different widths. Again, according to some aspects, the application of maximum electrical energy to the first and second input signals occurs non-concurrently. What is emphasized is that the electrical energy applied to the electrodes according to the present disclosure is not necessarily limited to any particular shape, amplitude, or duration.

For the first input signal shown in FIG. 2A, the pulse widths of the pulses $M_1$ and $M_2$ are 0.2 second (s) and the pulse widths of the pulses $M_3$, $M_4$, $M_5$, and $M_6$ are 0.25 s. For the second input signal, the pulse widths for the pulses $G_1$, $G_2$, $G_3$, and $G_4$ are 0.2 s. The relaxation widths of the first input signal are 0.2 s, 0.35 s, 0.35 s, 0.35 s, and 0.35 s after the pulses $M_1$-$M_5$, respectively. The relaxation widths of the second input signal are 0.4 s, 0.4 s, 0.4 s, and 0.35 s after the pulses $G_1$-$G_4$, respectively. The pulse width of the hematocrit pulse is 0.2 s.

The graph shown in FIG. 2A is just one example of intertwined first and second input signals, in accord with aspects of the present disclosure. In a more general case, the first and second input signals can have fewer pulses, while still including intertwined first and second input signals.

FIG. 2B shows a graph illustrating alternative exemplary intertwined input signals for an electrochemical biosensor system, such as the system 100 of FIG. 1, in accord with aspects of the present disclosure. More specifically, FIG. 2B shows two input signals, represented by the labels WE1 and WE2, where WE1 refers to the first input signal, as described herein, and WE2 refers to the second input signal, as described herein. Thus, as described in relation to the biosensor system 100 of FIG. 1, the first input signal WE1 includes two pulses of constant potential (voltage) applied across the working electrode 114 and the counter electrode 116. As described in relation to the biosensor system 100 of FIG. 1, the second input signal WE2 includes one pulse of constant potential (voltage) applied across the bare electrode 118 and the counter electrode 116. The pulses of the first input signal WE1 from left to right have potentials of 0.5 V and 0.35 V, and the pulse of the second input signal WE2 has a potential of 0.15 V.

Because the pulse of the second input signal WE2 separates the two pulses of the first input signal WE1, and the working electrode 114 is in a state of relaxation at least during the pulse of the second input signal WE2, the pulses of the first and second input signals WE1 and WE2 are intertwined, as described herein. Thus, the graph shown in FIG. 2B can be considered one of the broadest applications of intertwined first and second input signals.

FIG. 2C shows a graph illustrating yet further alternative exemplary intertwined input signals for an electrochemical biosensor system, such as the system 100 of FIG. 1, in accord with aspects of the present disclosure. More specifically, FIG. 2C shows two input signals, represented by the labels WE1 and WE2, where WE1 refers to the first input signal, as described herein, and WE2 refers to the second input signal, as described herein. Thus, as described in relation to the biosensor system 100 of FIG. 1, the first input signal WE1 includes two pulses of constant potential (voltage) applied across the working electrode 114 and the counter electrode 116. As described in relation to the biosensor system 100 of FIG. 1, the second input signal WE2 includes two pulses of constant potential (voltage) applied across the bare electrode 118 and the counter electrode 116. The pulses of the second input signal WE2 from left to right have potentials of 0.15 V and 0.25 V, and the pulses of the first input signal WE1 from left to right have potentials of 0.35 V and 0.25 V.

Again, because at least the second pulse of the second input signal WE2 separates the two pulses of the first input signal WE1, and the working electrode 114 is in a state of relaxation at least during the second pulse of the second input signal WE2, the pulses of the first and second input signals WE1 and WE2 are intertwined, as described herein. The graph shown in FIG. 2C can be considered another application of intertwined first and second input signals.

FIG. 2A-2C illustrate just some examples of intertwined first and second input signals that can be applied to a sample for determining a concentration of a target analyte in the sample. One or more characteristics of the first and/or second input signals shown in FIGS. 2A-2C can be varied without departing from the spirit and scope of the present disclosure.

In some aspects, the total numbers of pulses of the first and/or second input signals can vary from the numbers of pulses illustrated in FIGS. 2A-2C. As compared to FIG. 2A, the first input signal can have more or less than six pulses. In some aspects, the first input signal can have two pulses (as shown in FIGS. 2B and 2C), three pulses, four pulses, five pulses, seven pulses, eight pulses, nine pulses, or more. Similarly, as compared to FIG. 2A, the second input signal can have more or less than four pulses. In some aspects, the second input signal can have one pulse (as shown in FIG. 2B, during a relaxation of the first input signal) two pulses (as shown in FIG. 2C, with at least one pulse during a relaxation of the first input signal), three pulses, four pulses, five pulses, six pulses, seven pulses, eight pulses, nine pulses, or more pulses.

Figure 3:
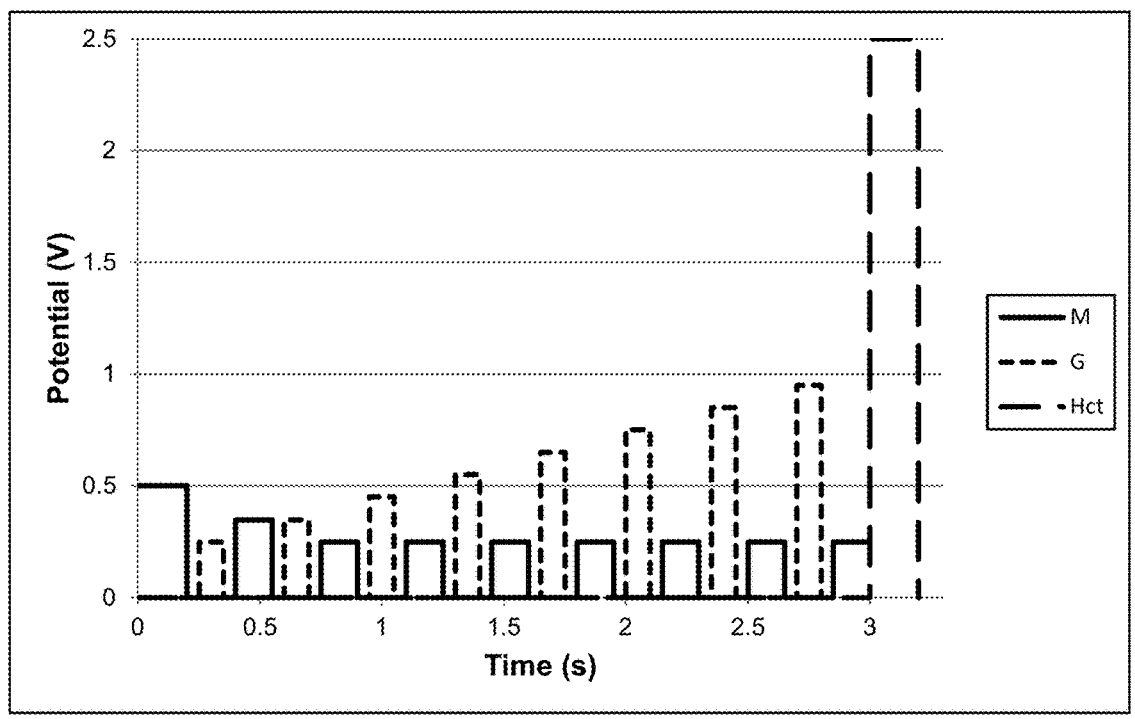
FIG. 3 is a graph illustrating an alternative application of intertwined input signals for a biosensor system, in accord with additional aspects of the present disclosure.

FIG. 3 is a graph illustrating an alternative application of intertwined input signals for an electrochemical biosensor system, such as the system 100 of FIG. 1, in accord with additional aspects of the present disclosure. FIG. 3 includes three input signals represented by the labels M, G, and Hct. Like in FIG. 2A, the first input signal M of FIG. 3 includes pulses of constant potential applied across the working electrode 114 and the counter electrode 116, and the second input signal G of FIG. 3 also includes pulses of constant voltage applied across the bare electrode 118 and the counter electrode 116, in relation to the system 100 of FIG. 1. The first input signal M of FIG. 3 includes nine pulses, which will be referred to here in the order in which they appear from left to right on the graph as $M_1$, $M_2$, $M_3$, $M_4$, $M_5$, $M_6$, $M_7$, $M_8$, and $M_9$. The potentials for the pulses of the first input signal M can be, for example, 0.5 V and 0.35 V for the first and second pulses, respectively, and 0.25 V for the remaining pulses. The second input signal G includes eight pulses, which will be referred to here in the order in which they appear from left to right on the graph as $G_1$, $G_2$, $G_3$, $G_4$, $G_5$, $G_6$, $G_7$, and $G_8$. The potentials for the pulses of the second input signal G can be, for example and from left to right, 0.25 V, 0.35 V, 0.45 V, 0.55 V, 0.65 V, 0.75 V, 0.85 V, and 0.95 V. Each of the pulses of the second input signal can have a pulse width of 0.15 V such that the potential change is about 286 mV/s starting from 0.25 V and ending at 0.95 V within about 2.45 s. At the end is the hematocrit single pulse Hct of FIG. 3.

Although only one pulse of the second input signal is shown as separating two adjacent pulses of the first input signal, in some aspects, the second input signal can have multiple pulses between adjacent pulses of the first input signal. For example, separating each pulse of the first input signal can be two pulses, three pulses, four pulses, five pulses, or more pulses of the second input signal. Further, after every pulse of the first input signal can be the same number of pulses of the second input signal, different numbers of pulses of the second input signal, or a combination of the same and different numbers of pulses of the second input signal.

Where multiple pulses of the second input signal separate two adjacent pulses of the first input signal, the multiple pulses of the second input signal are each separated by relaxations of the second input signal such that, for example, N pulses of the second input signal that separate two adjacent pulses of the first input signal include N−1 relaxations of the second input signal. The multiple pulses and at least one relaxation of the second input signal between the two pulses of the first input signal can be considered as a single duty cycle of the second input signal, or each pair of pulse and relaxation can be considered a single duty cycle of the second input signal such that multiple duty cycles of the second input signal can separate the two pulses of the first input signal.

The input signals of FIG. 2A are applied to the sample within about 3.2 s. Where there are more pulses for the first and/or second input signals than in FIG. 2A, the first and second input signals can be applied to the sample over the same amount of time, as illustrated in FIG. 3, or a different amount of time. In some aspects, a greater number of pulses for the first and/or second input signals can be applied within a shorter amount of time, or a longer amount of time, than the amount of time shown in FIGS. 2A and 3. Similarly, where there are fewer pulses for the first and/or second input signals than in FIG. 2A, the first and second input signals can be applied to the sample over the same amount of time or a different amount of time. In some aspects, a fewer number of pulses for the first and/or second input signals can be applied within a shorter amount of time, or a longer amount of time, than the amount of time shown in FIGS. 2A and 3. Based on there being intertwined first and second input signals, the total amount of time of application of the first and second input signals can be reduced, as compared to conventional biosensor systems, while still maintaining the same or a higher level of accuracy and precision.

As tangentially described above in relation to FIG. 3, in some aspects, the potentials of the pulses of the first and/or second input signals can vary from the potentials of the pulses illustrated in FIG. 2A. Each pulse of the first input signal can be different or the same intensity or amplitude as one or more other pulses of the first input signal. Similarly, each pulse of the second input signal can be different or the same intensity or amplitude as one or more other pulses of the second input signal. The potential of the first input signal is configured to sample the redox potential of the analyte in combination with the one or more reagents. Accordingly, for detecting the concentration of glucose in a WB sample, as an example, the potentials of the first input signal can be predominately about 0.25 V relative to the counter electrode in the sensor (e.g., the redox potential of the mediator), with one or more initial pulses at higher or lower potentials to prepare the system for sampling.

The second input signal can be used to sample the range of redox potentials of species within the sample besides the target analyte or related measureable species. Accordingly, the potentials of the second input signal can vary based on the intended and/or expected range of the redox potentials of other species in the sample. For example, the potentials of the pulses can vary from 0.01 V to 2.5 V, with varying levels of granularity.

Figure 4:
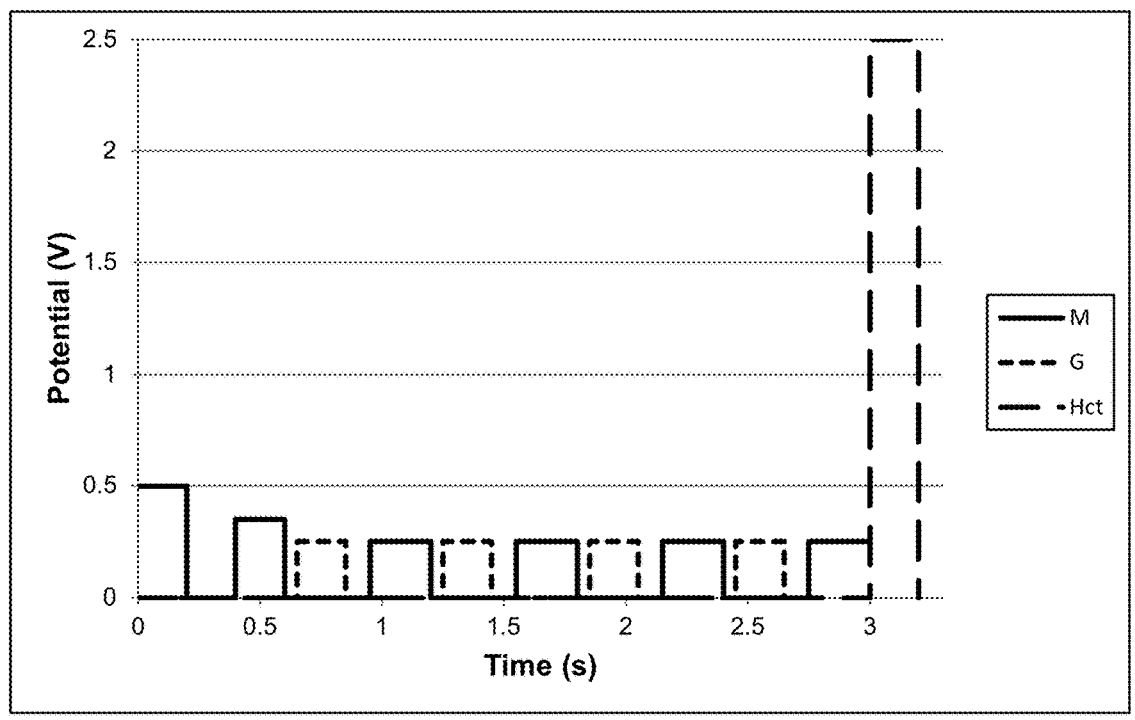
FIG. 4 is a graph illustrating an alternative application of intertwined input signals for a biosensor system, in accord with additional aspects of the present disclosure.

By way of example, FIG. 4 is a graph illustrating an alternative application of intertwined input signals for an electrochemical biosensor system, such as the system 100 of FIG. 1, in accord with additional aspects of the present disclosure. FIG. 4 includes three input signals represented by the labels M, G, and Hct. Like before, the first input signal M includes pulses of constant potential applied across the working electrode 114 and the counter electrode 116, and the second input signal G also includes pulses of constant potential applied across the bare electrode 118 and the counter electrode 116, in relation to the system 100 of FIG. 1. The first input signal is identical to the first input signal of FIG. 2A. However, each pulse of the second input signal of FIG. 4 has the same potential. At the end is the hematocrit single pulse Hct.

In some aspects, the length of time over which the first and second input signals are applied to the sample can be shortened or lengthened. The length of time can be shortened or lengthened by varying the pulse widths and/or the relaxation widths for one or more of the pulses of one or more of the first and second input signals. By way of example, the width of each relaxation of the first and second input signals can be shortened to reduce the overall time required to apply the first and second input signals to the sample. The length of time can be shortened or lengthened alternatively or additionally by varying the number of pulses of the first and/or second input signals.

Figure 5:
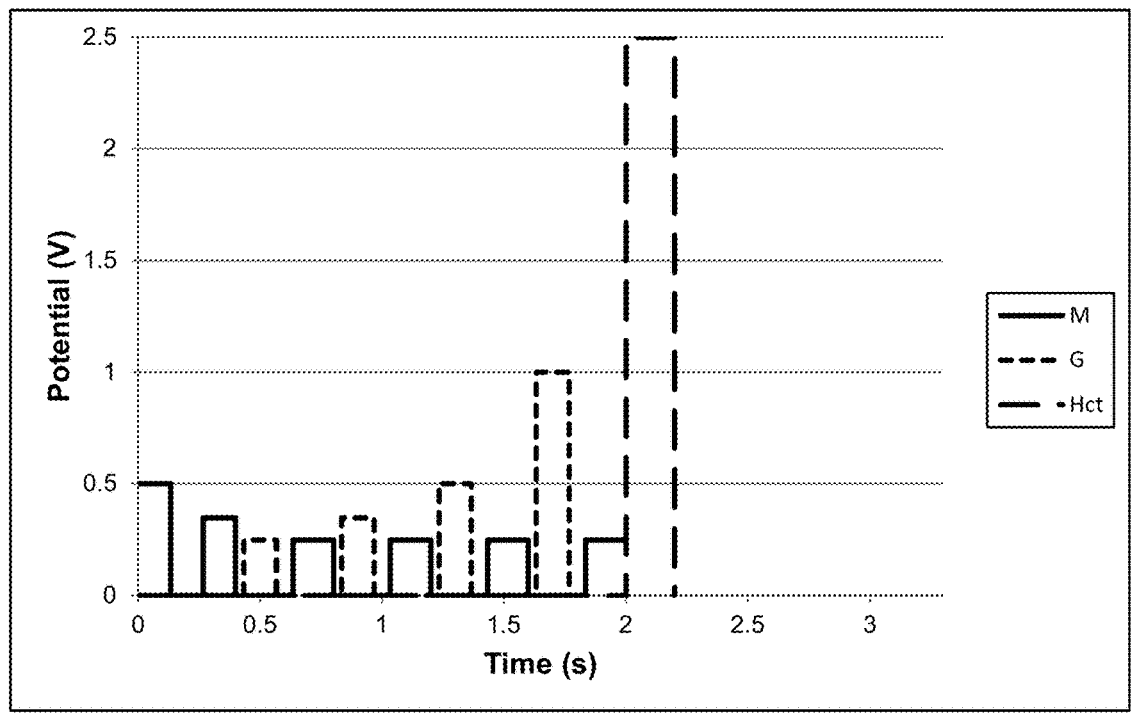
FIG. 5 is a graph illustrating an alternative application of intertwined input signals for a biosensor system, in accord with additional aspects of the present disclosure.

By way of example, FIG. 5 is a graph illustrating an alternative application of intertwined input signals for an electrochemical biosensor system, such as the system 100 of FIG. 1, in accord with additional aspects of the present disclosure. FIG. 5 includes three input signals represented by the labels M, G, and Hct, where, like before, the first input signal M includes pulses of constant potential applied across the working electrode 114 and the counter electrode 116 in relation to the system 100 of FIG. 1. The first and second input signals are identical to the first and second input signals of FIG. 2A. However, the first and second input signals are applied to the sample over a shorter period of time. As opposed to the 3.2 s of FIG. 2A, the first and second input signals of FIG. 5 are applied within 2.2 s, which includes the Hct pulse.

Based on the intertwining of the first and second input signals, the amount of time required for applying the intertwined input signals to the sample can be reduced as compared to conventional biosensor systems that do not include intertwined input signals. However, the reduction in time does not suffer from a commensurate reduction in accuracy and/or precision. Rather, information measured and/or collected in response to the intertwined second input signal, alone or in combination with information measured and/or collected in response to the first input signal, allows for faster analysis times with similar or even improved accuracy and precision.

Figure 6A:
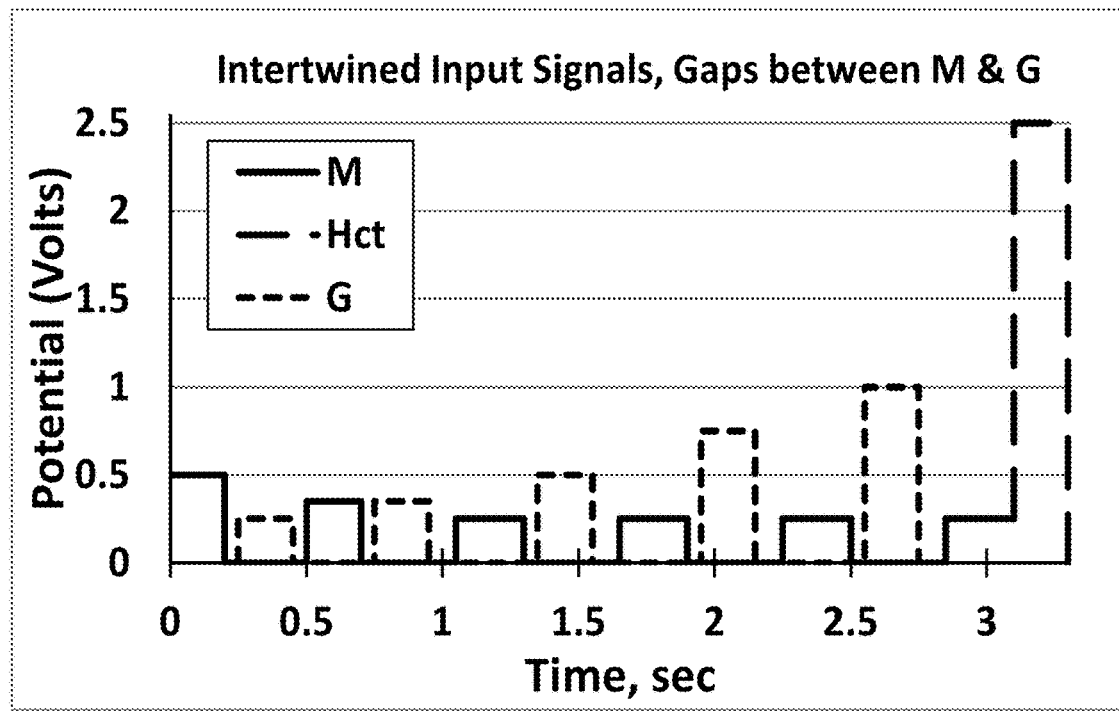
FIG. 6A is a graph illustrating an alternative application of intertwined input signals for a biosensor system, in accord with additional aspects of the present disclosure.

FIG. 6A is a graph illustrating an alternative application of intertwined input signals for an electrochemical biosensor system, such as the system 100 of FIG. 1, in accord with additional aspects of the present disclosure. FIG. 6A includes three input signals represented by the labels M, G, and Hct. Like in FIG. 2A, the first input signal M includes pulses of constant potential applied across the working electrode 114 and the counter electrode 116, and the second input signal G also includes pulses of constant potential applied across the bare electrode 118 and the counter electrode 116, in relation to the system 100 of FIG. 1.

As shown, the first input signal M includes six pulses, which will be referred to here in the order in which they appear from left to right on the graph as $M_1$, $M_2$, $M_3$, $M_4$, $M_5$, and $M_6$. The pulse $M_1$ has a potential of 0.5 V, the pulse $M_2$ has a potential of 0.35 V, and the remaining pulses $M_3$ to $M_6$ have potentials of 0.25 V. Because the pulses of the first input signal M are applied via the working electrode 114 with the one or more reagents, the pulses of the first input signal M probe the target analyte in the sample, either directly or indirectly through a mediator or other measureable species.

As shown, the second input signal G includes five pulses, which will be referred to here in the order in which they appear from left to right on the graph as $G_1$, $G_2$, $G_3$, $G_4$, and $G_5$. The pulse $G_1$ has a potential of 0.25 V, the pulse $G_2$ has a potential of 0.35 V, the pulse $G_3$ has a potential of 0.5 V, the pulse $G_4$ has a potential of 0.75 V, and the pulse $G_5$ has a potential of 1.0 V. Because the bare electrode 118 does not include one or more reagents that are responsive to the target analyte within the sample, the pulses of the second input signal G applied via the bare electrode 118 do not probe the target analyte that is targeted by the working electrode 114 in the sample. Instead, the pulses of the second input signal G applied via the bare electrode 118 probe the other species in the sample across the electrochemical detection window, including potential interference species in the sample as described in further detail below.

The third input signal Hct is a single pulse for determining the hematocrit level of the sample, in the case of a WB sample. As described in relation to the biosensor system 100 of FIG. 1, the single pulse of the third input signal Hct is a constant voltage of 2.5 V applied across the bare electrode 118 and the combination of the counter electrode 116 and the working electrode 114. Alternatively, the single pulse of the third input signal Hct can instead be applied across the bare electrode 118 and the counter electrode 116, with the working electrode 114 in an open state. Although described as three separate input signals, the second input signal and the third input signal can instead be considered a single input signal, such as the second input signal including the pulses $G_1$-$G_5$ and the pulse Hct for determining the hematocrit level.

After each pulse of the working electrode 114 during the first input signal is a relaxation of the working electrode 114 until the next pulse of the working electrode 114 of the first input signal. Similarly, after each pulse of the bare electrode 118 during the second input signal is a relaxation of the bare electrode 118. As shown, after each pulse of the working electrode 114 and the bare electrode 118 is a relaxation of the system 100, until the final pulse of the working electrode $M_6$. The relaxations of the system 100 are shown because portions of the relaxations of both the working electrode 114 (first input signal) and the bare electrode 118 (second input signal) overlap. That is, each gap between the pulses of the working electrode 114 and the pulses of the bare electrode 118 is a relaxation of the system 100.

Because the intertwined input signals shown in FIG. 6A include relaxations of the system 100, if a period or a duty cycle of the intertwined input signals is defined as beginning at the beginning of a pulse of the working electrode 114 and ending at the beginning of the next pulse of the working electrode 114, each period or duty cycle includes two system relaxations. Other aspects of the present disclosure, however, include intertwined input signals that do not require relaxations of the system.

Figure 6B:
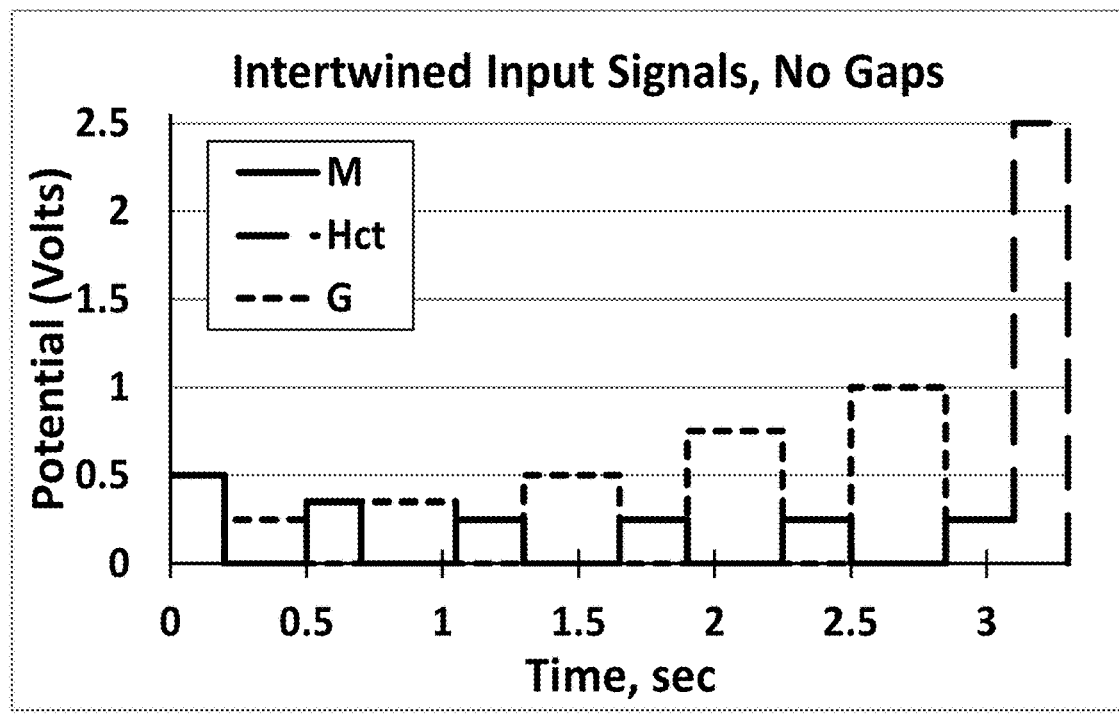
FIG. 6B is a graph illustrating an alternative application of intertwined input signals for a biosensor system, without system relaxations, in accord with additional aspects of the present disclosure.

FIG. 6B is a graph illustrating an alternative application of intertwined input signals for an electrochemical biosensor system, such as the system 100 of FIG. 1, in which there are no relaxations of the system 100, in accord with additional aspects of the present disclosure. The intertwined inputs signals are identical to the signals shown in FIG. 6A, except that the pulse widths of the pulses of the bare electrode 118 are lengthened so that there are no system relaxations after each pulse of the working electrode 114 and after each pulse of the bare electrode 118. However, the intertwined input signals of FIG. 6B still include the relaxations of the working electrode 114 after each pulse of the working electrode 114 and up to the next pulse of the working electrode 114, and the relaxations of the bare electrode 118 after each pulse of the bare electrode 118 and up to the next pulse of the bare electrode 118.

Although the pulse widths of the pulses of the bare electrode 118 can be lengthened to achieve no relaxations of the system, alternatively, the pulse widths of the pulses of the working electrode 114 can be lengthened, or the pulse widths of the pulses of both the working electrode 114 and the bare electrode 118 can be lengthened to achieve no relaxations of the system.

Again, the intertwined input signals shown in FIG. 6A include two relaxations of the system 100 for each period or duty cycle of the intertwined input signals defined as beginning at the beginning of a pulse of the working electrode 114 and ending at the beginning of the next pulse of the working electrode 114. In some aspects, the intertwined input signals can include a single relaxation of the system 100 for each period or duty cycle.

Figure 6C:
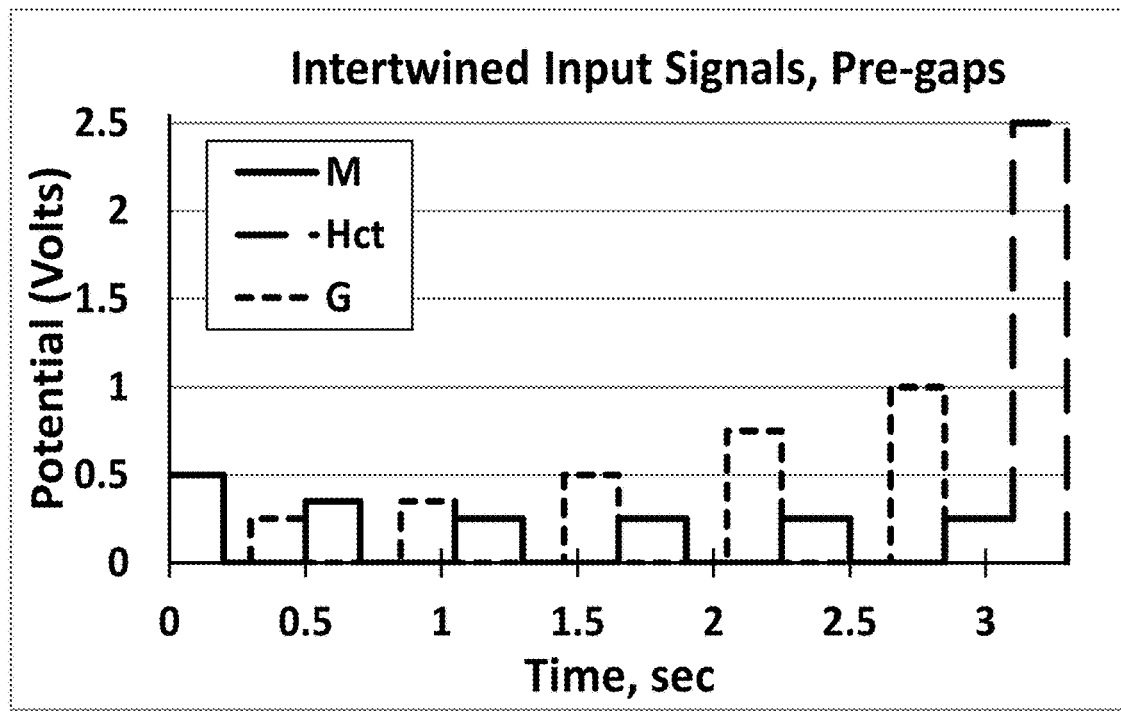
FIG. 6C is a graph illustrating an alternative application of intertwined input signals for a biosensor system, with a system relaxation after a working electrode pulse, in accord with additional aspects of the present disclosure.

FIG. 6C is a graph illustrating an alternative application of intertwined input signals for an electrochemical biosensor system, such as the system 100 of FIG. 1, in which there is only one system relaxation for each period or duty cycle, in accord with additional aspects of the present disclosure. The intertwined inputs signals are identical to the signals shown in FIG. 6A, except that the pulses of the bare electrode 118 are shifted to occur immediately before the next pulse of the working electrode 114 such that there is no system relaxation between the pulse of the bare electrode 118 and the next pulse of the working electrode 114. However, there is a system relaxation between a previous pulse of the working electrode 114 and the next pulse of the bare electrode 118 that separates adjacent pulses of the working electrode 114. The intertwined input signals of FIG. 6C still include the relaxations of the working electrode 114 after each pulse of the working electrode 114 and up to the next pulse of the working electrode 114, and the relaxations of the bare electrode 118 after each pulse of the bare electrode 118 and up to the next pulse of the bare electrode 118.

Figure 6D:
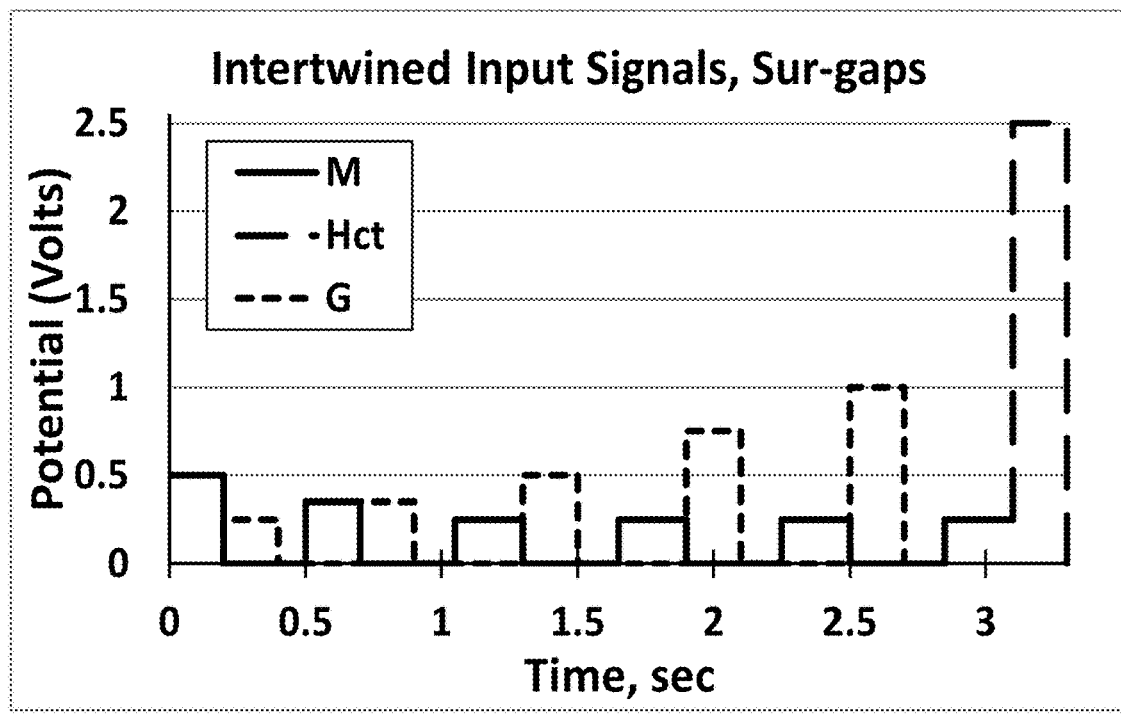
FIG. 6D is a graph illustrating an alternative application of intertwined input signals for a biosensor system, with a system relaxation after a bare electrode pulse, in accord with additional aspects of the present disclosure.

Instead of occurring immediately after the pulses of the working electrode 114, the system relaxations can occur after the pulse of the bare electrode 118. FIG. 6D is a graph illustrating an alternative application of intertwined input signals for an electrochemical biosensor system, such as the system 100 of FIG. 1, in which there is only one system relaxation for each period or duty cycle, in accord with additional aspects of the present disclosure. The intertwined input signals are identical to the signals shown in FIG. 6C, except that the pulses of the bare electrode 118 are shifted to occur immediately after a pulse of the working electrode 114 such that there is no system relaxation between the pulse of the working electrode 114 and the next pulse of the bare electrode 118. However, there is a system relaxation between a previous pulse of the bare electrode 118 and the next pulse of the working electrode 114 that separates adjacent pulses of the bare electrode 118. The intertwined input signals of FIG. 6D still include the relaxations of the working electrode 114 after each pulse of the working electrode 114 and up to the next pulse of the working electrode 114, and the relaxations of the bare electrode 118 after each pulse of the bare electrode 118 and up to the next pulse of the bare electrode 118.

Referring back to FIG. 2A, electrical measurements are taken in response to the first and second input signals, or portions of the first and second input signals. The measurements of the sample constitute one or more output signals measured by the measurement device 102. Specifically, in response to the first input signal, a first output signal or working output signal is measured. In response to the second input signal, a second output signal or bare output signal is measured. Based on the intertwined first and second input signals, the resulting first and second output signals also are intertwined.

Figure 7:
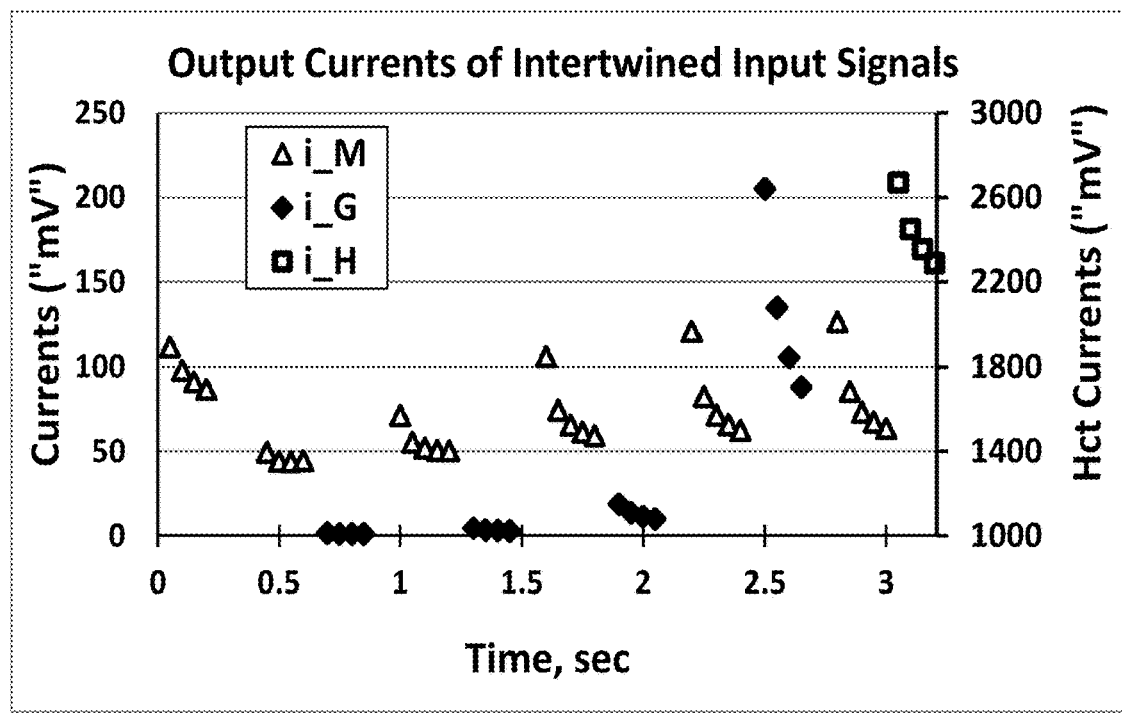
FIG. 7 is a graph illustrating intertwined first and second output signals measured in response to the intertwined first and second input signals of FIG. 2A, in accord with aspects of the present disclosure.

FIG. 7 is a graph illustrating intertwined first and second output signals measured in response to the intertwined first and second input signals of FIG. 2A, in accord with aspects of the present disclosure. Based on the first and second input signals being constant voltages applied across the respective electrode pairs, the first and second output signals represent amperometric measurements of the resultant output currents of the sample responsive to the first and second input signals.

Any number of current measurements or values can be measured in response to each one of the pulses of the first and second input signals. For convenience of explanation, and as shown in FIG. 7, the specific number of currents described below was measured in response to the pulses of the first and second input signals.

With respect the first output signal, four output currents were measured in response to the first two M pulses $M_1$ and $M_2$, and five output currents were measured in response to the last four M pulses $M_3$-$M_6$. These output currents are designated according to the scheme $i_{MN,L}$, where i represents a current, M represents that the current is responsive to the first input signal, N represents the pulse number of the input signal, and L represents the current or measurement number for that particular pulse number. Thus, for example, $i_{M1,1}$ represents the first current for the first pulse of the first input signal, and $i_{M6,5}$ represents the fifth current for the sixth pulse of the first input signal.

With respect to the second output signal, four currents were measured in response to the first four G pulses $G_1$-$G_4$. These currents are designated according to the scheme $i_{GN,L}$, where i represents a current, G represents that the current is responsive to the second input signal, N represents the pulse number of the input signal, and L represents the current or measurement number for that particular pulse number. Thus, for example, $i_{G2,2}$ represents the second current for the second pulse of the second input signal, and $i_{G3,4}$ represents the fourth current for the third pulse of the second input signal.

With respect to the hematocrit portion of the second input signal (or the third input signal), four current values were measured in response to the single pulse Hct. These currents are designated according to the scheme $i_{Hct,L}$, where i represents a current, Hct represents that the current is related to the hematocrit value, and L represents the current or measurement number for the hematocrit pulse.

Because the bare electrode 118 does not have a reagent that facilitates an oxidation or reduction of the target analyte whose concentration is sought to be measured, the current measurements were relatively constant in response to the second input signal, as shown in FIG. 7. Instead, the current measurements were indicative mostly of species in the sample that are unrelated to the oxidization of the analyte. Further, by applying voltage pulses to the sample at varying potentials for the second input signal, oxidizable species at various potentials were sampled. Thus, the voltage pulses of the bare electrode 118 during the second input signal sensed a different analyte target of the sample in a WB sample than the analyte target sensed by the working electrode 114 during the first input signal, or probe the WB environment profile through varying potential pulses. Subtle differences from different blood types of individuals can still exist and be expressed throughout the current responses at different combinations of pulse potentials, for instance, the ratios of ending currents among different second input signal pulses.

Information from the second output signal provides for increased accuracy over conventional biosensor systems at the same or shorter test times. For instance, the error parameters generated based on the second output signal, both alone and in combination with information from the first output signal, complement the error parameters generated based on the first output signal for error compensation that accounts for interference species oxidized by the working electrode 114 but unrelated to the concentration of the analyte. Without the second input signal applied between the bare electrode 118 and the counter electrode 116, interference species oxidized by the working electrode 114 during the first input signal cannot be isolated or separated out in the conventional biosensor systems from the oxidation of the analyte.

Moreover, applying an intertwined second input signal with a first input signal to a sample is contrary to conventional approaches in the electrochemical arts as applied to analyte concentration determination. Conventional approaches have previously attempted to distinguish the effects of other species in the sample, other than the target analyte, mediator, or related measureable species, by altering the required potential of the working electrode to levels that would be unaffected by such other species. Thus, following the thrust of conventional approaches, one might assume that pulsing the sample with a bare electrode at potentials spanning the electrochemical detection window would have relatively little or no effect or influence on the target analyte concentration determination when the redox potential of the target analyte, mediator, or related measureable species is at a potential other than these additional potentials. This appearance of no effect is further evidenced by the relatively constant responses of the sample to the varying pulses of the second input signal, as shown by the second output signal in FIG. 7. However, for the reasons discussed herein, a directed analysis of the second output signal, alone and/or in combination with the first output signal, actually reveals useful information that allows for a more accurate and/or precise determination of the target analyte concentration, particularly for shorter assay time periods. As further discussed below, the shorter assay times that are permitted based on intertwined first and second input signals also allows for greater linearity in the sample, allowing for concentration determinations that can exceed well beyond upper limits of conventional biosensor systems, such as above 600 mg/dL for glucose biosensor systems.

As described above, based on the current measurements of the first and second output signals, error parameters can be generated. The error parameters correlate error in measuring the concentration of the target analyte to known factors that cause deviations from the actual concentration of the target analyte, such as interference species within the sample. The error parameters can be various types of parameters depending on how the corresponding biosensor system is configured, which generates the error from different error sources. For example, in some aspects, one or more currents of the second output signal can be error parameters. Additionally, or in the alternative, the error parameters can be based on ratios of the currents of the first output signal, the second output signal, and/or the first output signal relative to the second output signal. Error parameters based on the first or second output signal can be based on intra-pulse ratios or inter-pulse ratios.

Intra-pulse ratios are ratios based on current measurements in response to the same pulse. For example, intra-pulse ratios based on current measurements of the first output signal are designated according to the scheme $R_N = i_{MN,nth}/i_{MN,1st}$, where $R_N$ represents an intra-pulse ratio for pulse N of the first output signal, nth represents the last current for the pulse N, and 1st represents the first current for the pulse N. Referring back to FIG. 7, as an example, the first output signal would include six intra-pulse ratios of $R_1 = i_{M1,4}/i_{M1,1}$, $R_2 = i_{M2,4}/i_{M2,1}$, $R_3 = i_{M3,5}/i_{M3,1}$, $R_4 = i_{M4,5}/i_{M4,1}$, $R_5 = i_{M5,5}/i_{M5,1}$, and $R_6 = i_{M6,5}/i_{M6,1}$ for the six pulses of the first input signal.

Intra-pulse ratios based on current measurements of the second output signal are designated according to the scheme $RG_N = i_{GN,nth}/i_{GN,1st}$, where $RG_N$ represents an intra-pulse ratio for pulse N of the second output signal, and the remaining variables represent the similar values listed above for the intra-pulse ratio of the first output signal. Referring again to FIG. 7, the second output signal would include four intra-pulse ratios of $RG_1 = i_{G1,4}/i_{G1,1}$, $RG_2 = i_{G2,4}/i_{G2,1}$, $RG_3 = i_{G3,4}/i_{G3,1}$, and $RG_4 = i_{G4,4}/i_{G4,1}$ for the four pulses of the second output signal.

Inter-pulse ratios are ratios based on current measurements in response to the same signal but different pulses within the signal. For example, inter-pulse ratios based on current measurements of the first output signal are designated according to the scheme $R_{NO} = i_{MN,nth}/i_{MO,nth}$, where $R_{NO}$ represents the inter-pulse ratio for pulse N relative to pulse O of the first output signal, and nth is the last current for both pulse N and pulse O. Referring to FIG. 7, the first output signal would include inter-pulse ratios of $R_{21} = i_{M2,4}/i_{M1,4}$, $R_{31} = i_{M3,5}/i_{M1,4}$, $R_{32} = i_{M3,5}/i_{M2,4}$, $R_{41} = i_{M4,5}/i_{M1,4}$, $R_{42} = i_{M4,5}/i_{M2,4}$, $R_{43} = i_{M4,5}/i_{M3,5}$, $R_{51} = i_{M5,5}/i_{M1,4}$, $R_{52} = i_{M5,5}/i_{M2,4}$, $R_{53} = i_{M5,5}/i_{M3,5}$, $R_{54} = i_{M5,5}/i_{M4,5}$, $R_{61} = i_{M6,5}/i_{M1,4}$, $R_{62} = i_{M6,5}/i_{M2,4}$, $R_{63} = i_{M6,5}/i_{M3,5}$, $R_{64} = i_{M6,5}/i_{M4,5}$, and $R_{65} = i_{M6,5}/i_{M5,5}$. Other inter-pulse ratio types can include the ratio of the first current of a pulse to the ending current of another pulse, and the ratio of the ending current of a pulse to the first current of another pulse, or the like. Examples of these inter-pulse ratio types are $R'_{21} = i_{M2,1}/i_{M1,4}$, and $R''_{21} = i_{M2,4}/i_{M1,1}$.

Inter-pulse ratios based on current measurements of the second output signal are designated according to the scheme $RG_{NO}=i_{GN,nth}/i_{GO,nth}$, where $RG_{NO}$ represents the inter-pulse ratio for pulse N relative to pulse O of the second output signal, and the remaining variables represent the values listed above for the inter-pulse ratio of the first output signal. Referring to FIG. 7, the second output signal would include the inter-pulse ratios of $RG_{21}=i_{G2,4}/i_{G1,4}$, $RG_{31}=i_{G3,5}/i_{G1,4}$, $RG_{32}=i_{G3,5}/i_{G2,4}$, $RG_{41}=i_{G4,5}/i_{G1,4}$, $RG_{42}=i_{G4,5}/i_{G2,4}$, $RG_{43}=i_{G4,5}/i_{G3,5}$, $RG_{51}=i_{G5,5}/i_{G1,4}$, $RG_{52}=i_{G5,5}/i_{G2,4}$, $RG_{53}=i_{G5,5}/i_{G3,5}$, $RG_{54}=i_{G5,5}/i_{G4,5}$, $RG_{61}=i_{G6,5}/i_{G1,4}$, $RG_{62}=i_{G6,5}/i_{G2,4}$, $RG_{63}=i_{G6,5}/i_{G3,5}$, $RG_{64}=i_{G6,5}/i_{G4,5}$, and $RG_{65}=i_{G6,5}/i_{G5,5}$.

Ratios based on the first and second output signals are considered intertwined pulse ratios. Intertwined pulse ratios based on current measurements of the first output signal and the second output signal are designated according to the scheme $M_N G_O = i_{MN,nth}/i_{GN,nth}$, where $M_N$ is pulse N of the first output signal, $G_N$ is pulse O of the second output signal, and nth represents the last current measurement for the pulse N or O. Thus, for example, the intertwined pulses would include $M_1G_1=i_{M1,4}/i_{G1,4}$, $M_1G_2=i_{M1,4}/i_{G2,4}$, $M_1G_3=i_{M1,4}/i_{G3,4}$, $M_1G_4=i_{M1,4}/i_{G4,4}$, $M_2G_1=i_{M2,4}/i_{G1,4}$, $M_2G_2=i_{M2,4}/i_{G2,4}$, $M_2G_3=i_{M2,4}/i_{G3,4}$, $M_2G_4=i_{M2,4}/i_{G4,4}$, $M_3G_1=i_{M3,5}/i_{G1,4}$, $M_3G_2=i_{M3,5}/i_{G2,4}$, $M_3G_3=i_{M3,5}/i_{G3,4}$, $M_3G_4=i_{M3,5}/i_{G4,4}$, $M_4G_1=i_{M4,5}/i_{G2,4}$, $M_4G_2=i_{M4,5}/i_{G2,4}$, $M_4G_3=i_{M4,5}/i_{G3,4}$, $M_4G_4=i_{M4,5}/i_{G4,4}$, $M_5G_1=i_{M5,5}/i_{G1,4}$, $M_5G_2=i_{M5,5}/i_{G2,4}$, $M_5G_3=i_{M5,5}/i_{G3,4}$, $M_5G_4=i_{M5,5}/i_{G4,4}$, $M_6G_1=i_{M6,5}/i_{G1,4}$, $M_6G_2=i_{M6,5}/i_{G2,4}$, $M_6G_3=i_{M6,5}/i_{G3,4}$, and $M_6G_4=i_{M6,5}/i_{G4,4}$.

One or more of the intra-pulse and inter-pulse ratios for the second output signal and the intertwined pulse ratios for the first and second output signals can be used in compensation equations that adjust the correlation between the output signals and the concentration of the analyte to provide a more accurate and precise determination of the concentration of the analyte. The various calculated ratios based on the second output signal, or the first and second output signals, can be entered into multi-variable regression to generate the one or more compensation equations that account for error that is not accounted for by error parameters from the first output signal alone.

FIGS. 2A and 7 show only one of many contemplated example plots of the first and second input signals and the corresponding first and second output signals. The characteristics of the first and second input signals and resulting first and second output signals can be varied according to any of the above-described variations. Additional examples of the first and second input signals, and the corresponding first and second output signals, are shown and described below.

Specifically, FIGS. 8A-8D are graphs illustrating various arrangements of intertwined first and second input signals for an electrochemical biosensor system, such as the system 100 of FIG. 1, in accord with additional aspects of the present disclosure. FIGS. 8A-8D all show three input signals represented by the labels M, G, and Hct. The first input signals M include pulses of constant potential applied across the working electrode 114 and the counter electrode 116, the second input signals G include pulses of constant potential across the bare electrode 118 and the counter electrode 116, and the third input signals are single hematocrit pulses, as described above.

Figure 8A:
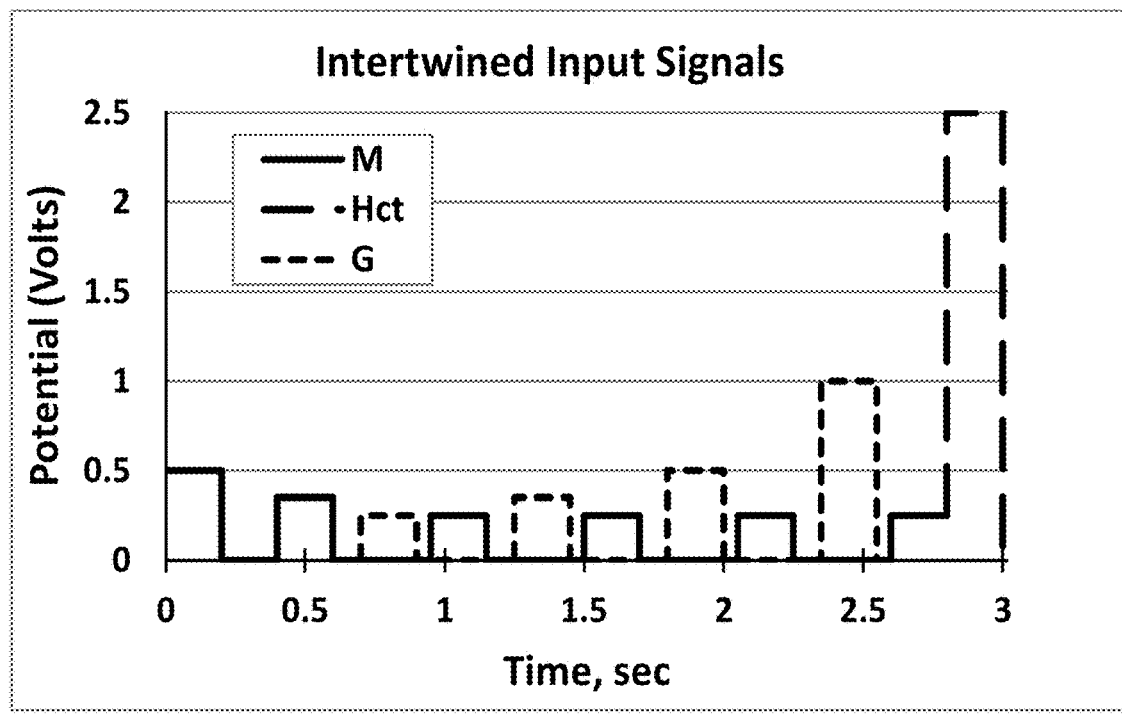
FIG. 8A is a graph illustrating an application of alternative intertwined first and second input signals for a biosensor system, in accord with additional aspects of the present disclosure.
Figure 8B:
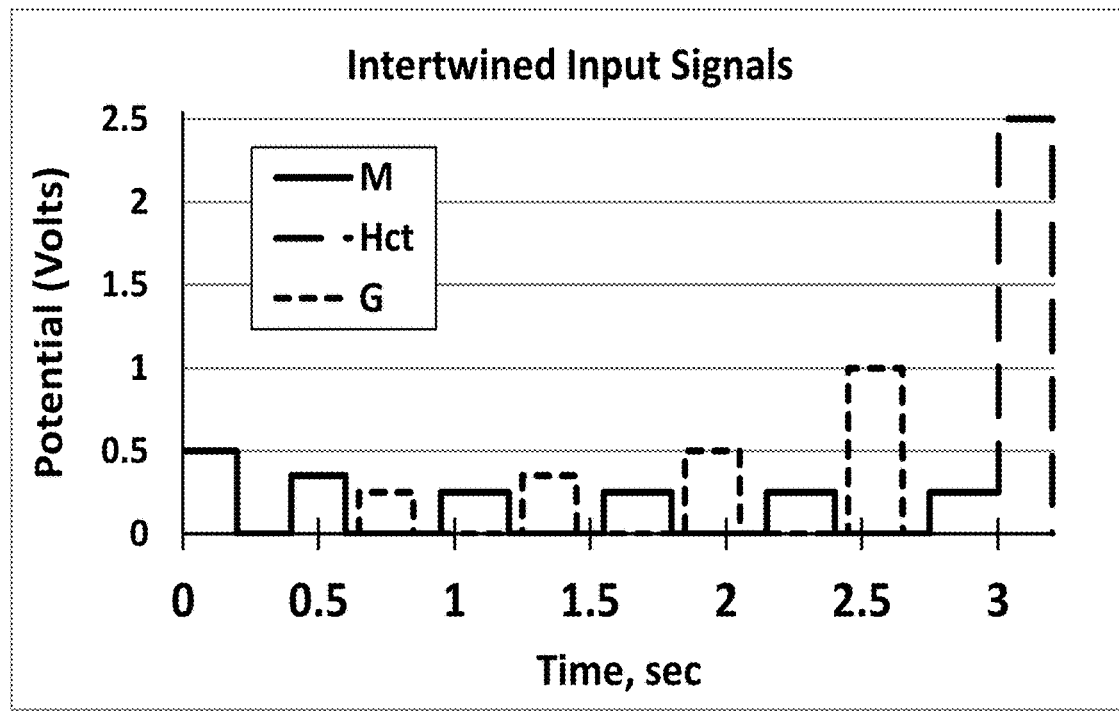
FIG. 8B is a graph illustrating an application of alternative intertwined first and second input signals for a biosensor system, in accord with additional aspects of the present disclosure.
Figure 8C:
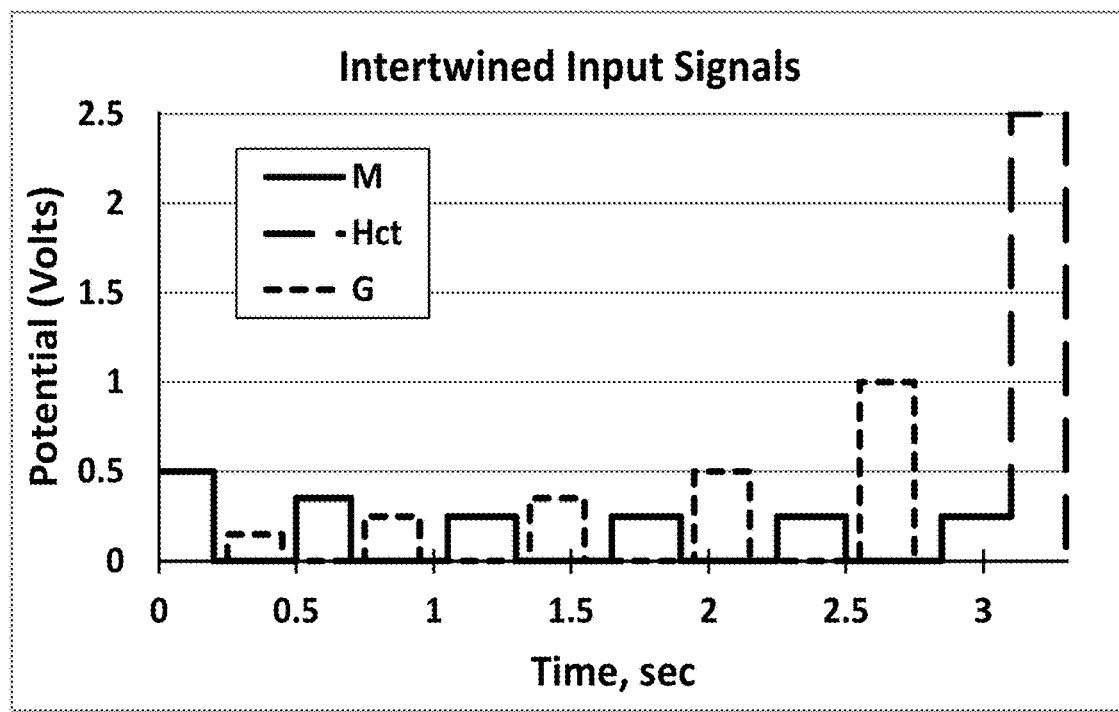
FIG. 8C is a graph illustrating an application of alternative intertwined first and second input signals for a biosensor system, in accord with additional aspects of the present disclosure.
Figure 8D:
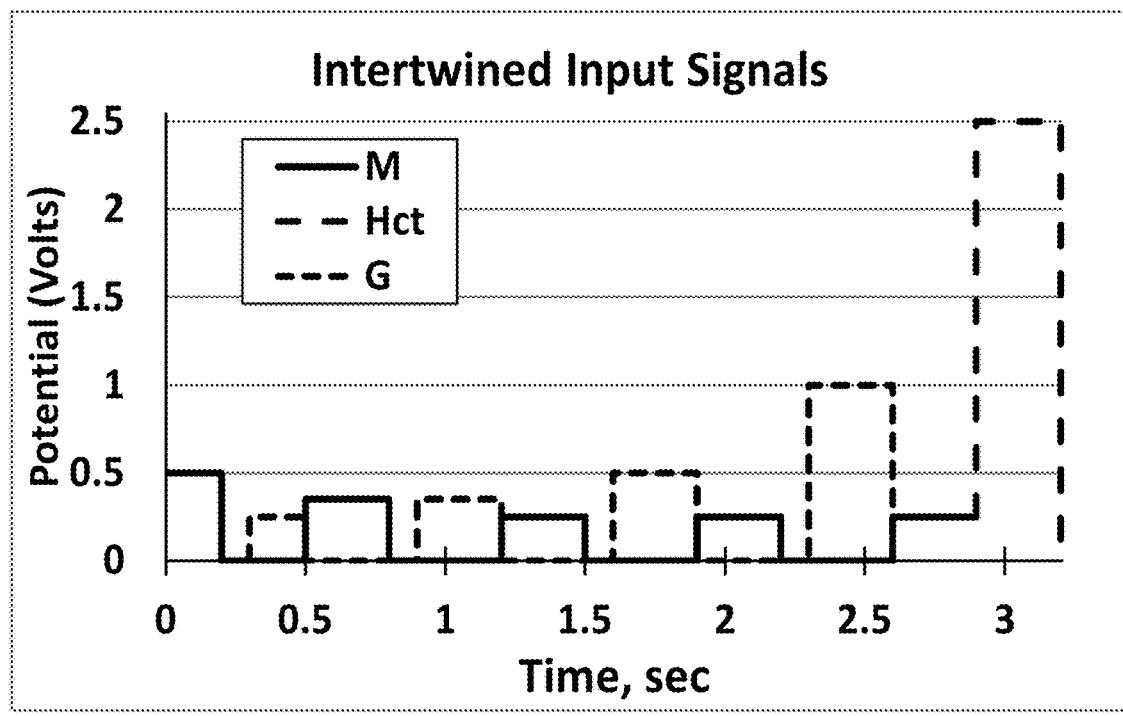
FIG. 8D is a graph illustrating an application of alternative intertwined first and second input signals for a biosensor system, in accord with additional aspects of the present disclosure.
Figure 9A:
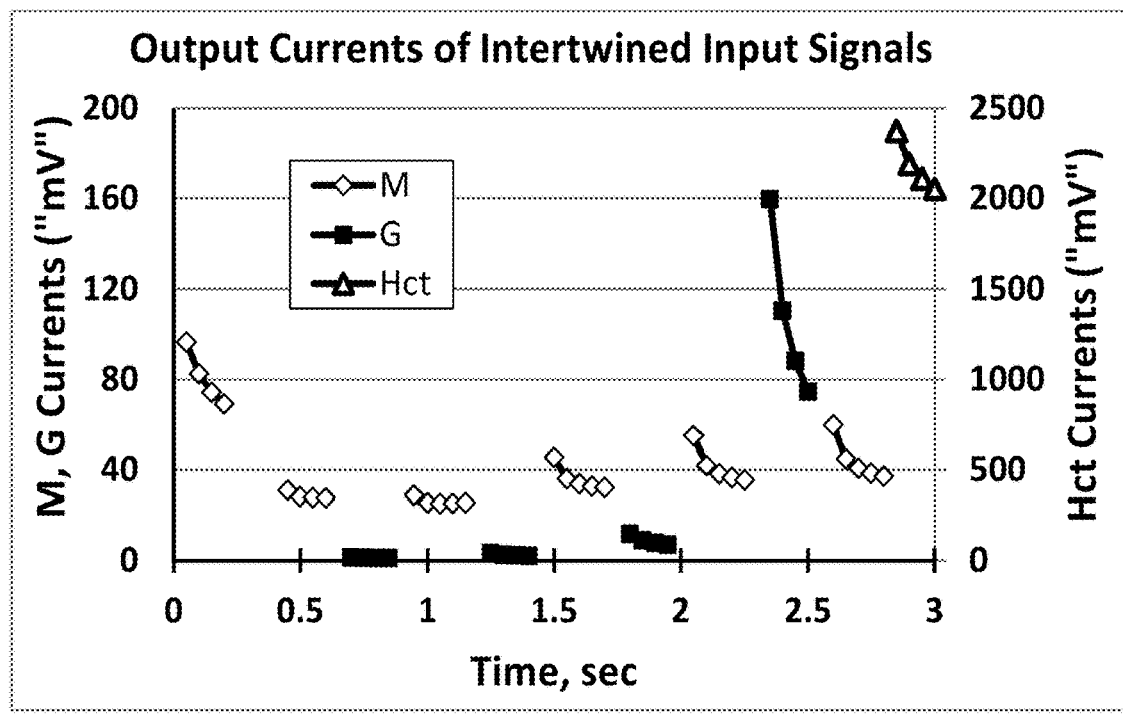
FIG. 9A is a graph illustrating output signals resulting from the intertwined first and second input signals of FIG. 8A, in accord with additional aspects of the present disclosure.
Figure 9B:
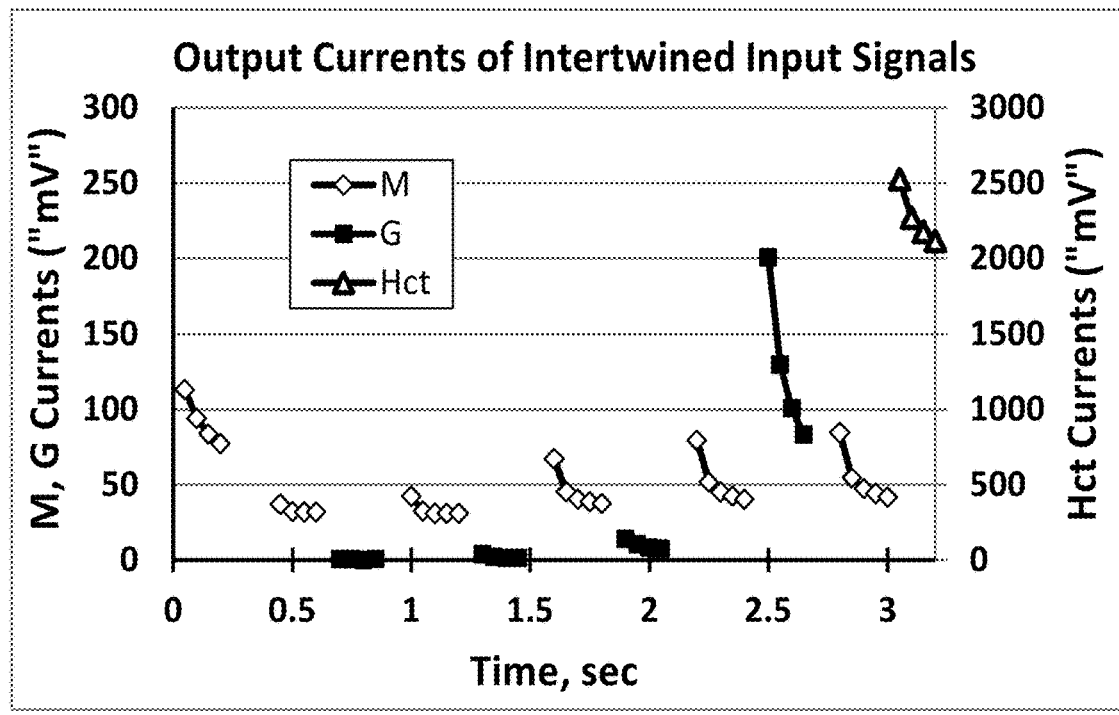
FIG. 9B is a graph illustrating output signals resulting from the intertwined first and second input signals of FIG. 8B, in accord with additional aspects of the present disclosure.
Figure 9C:
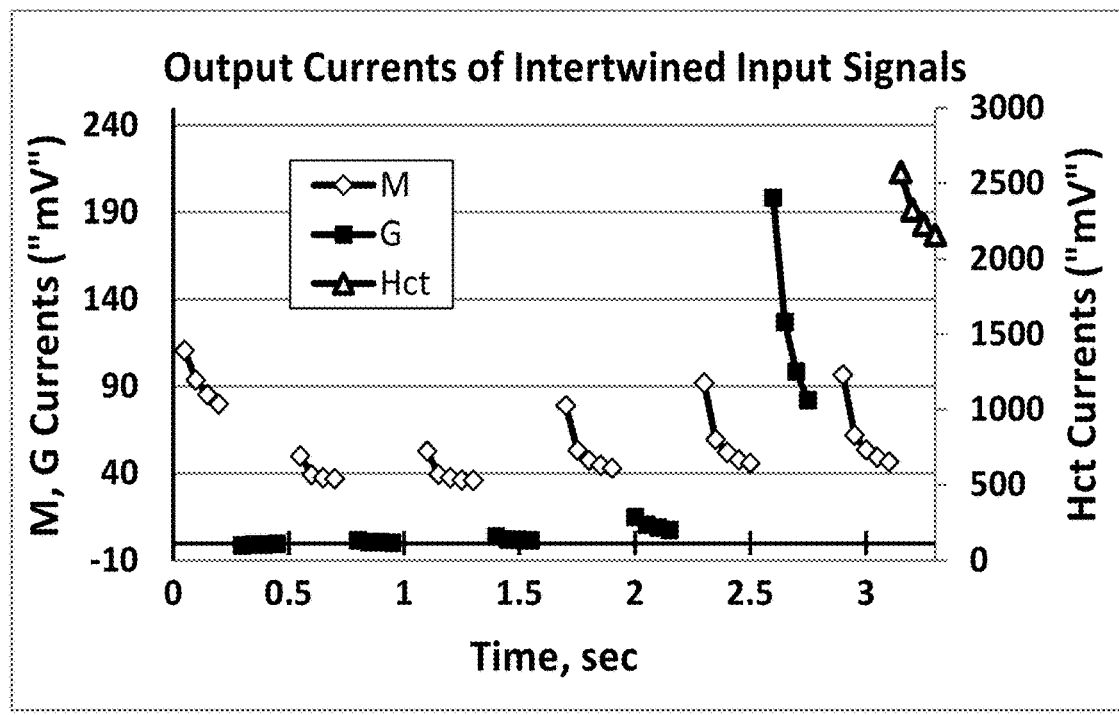
FIG. 9C is a graph illustrating output signals resulting from the intertwined first and second input signals of FIG. 8C, in accord with additional aspects of the present disclosure.
Figure 9D:
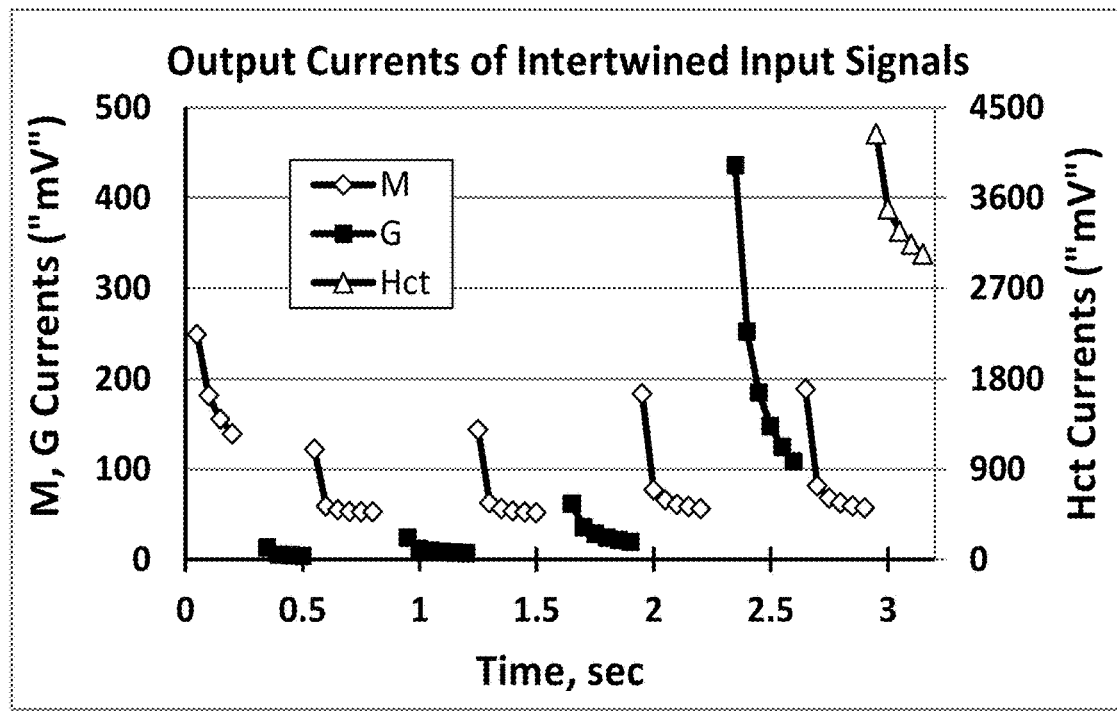
FIG. 9D is a graph illustrating output signals resulting from the intertwined first and second input signals of FIG. 8D, in accord with additional aspects of the present disclosure.

In FIG. 8A, the first input signal M has six pulses, the second input signal G has four pulses, and the third input signal has the single Hct pulse. The intertwined input signals of FIG. 8A are applied within 3 s. In FIG. 8B, the first input signal M has six pulses, the second input signal G has four pulses, and the third input signal has the single Hct pulse. The intertwined input signals of FIG. 8B are applied within 3.2 s. In FIG. 8C, the first input signal M has six pulses, the second input signal G has five pulses, and the third input signal has the single Hct pulse. The intertwined input signals of FIG. 8C are applied within 3.3 s. In FIG. 8D, the first input signal M has five pulses, the second input signal G has four pulses, and the third input signal has the single Hct pulse. The intertwined input signals of FIG. 8D are applied within 3.2 s.

The first input signals generally include potentials of 0.5 V and 0.35 V for the first and second pulses (from left to right) followed by subsequent pulses of 0.25 V. The second input signals generally include pulses of 0.25 V, 0.35 V, 0.5 V, and 1.0 V (from left to right). The ending pulse of the third input signal is about 2.5 V.

FIGS. 9A-9D are graphs illustrating output signals that resulted from the intertwined first and second input signals, as well as the third input signals, of FIGS. 8A-8D, in accord with additional aspects of the present disclosure. Specifically, FIGS. 9A-9D show the first, second, and third output signals from the input signals of FIGS. 8A-8D, respectively, when applied to a WB sample having 59 mg/dL glucose at 43% Hct and room temperature. The first output signal in response to the first input signal is represented by M, the second output signal in response to the second input signal is represented by G, and the third output signal in response to the third input signal is represented by Hct. But for the negative currents of the second output signal G in FIG. 9C in response to the first pulse at 0.15 V of the second input signal of FIG. 8C, current measurements in response to the pulses of the first and second input signals at 0.25 V and above were all positive, indicating the electrochemical environment of the WB samples.

FIGS. 10A-10D show reference correlations for different pulses of the first input signals in FIGS. 8A-8D, respectively, in accord with aspects of the present disclosure. As shown for FIGS. 10A and 10B, where the first input signals include six pulses, the last three pulses within time periods as short as 1.7 s demonstrate substantially identical linear responses. The last four pulses within time periods as short as 1.3 sec in FIG. 10C demonstrate substantially identical linear responses. Finally, FIG. 10D demonstrates that the responses from the last two pulses of five are identical with the responses from earlier pulses being lower than the last two. These correlations demonstrate that assay times of less than 2.0 s are feasible.

Figure 10A:
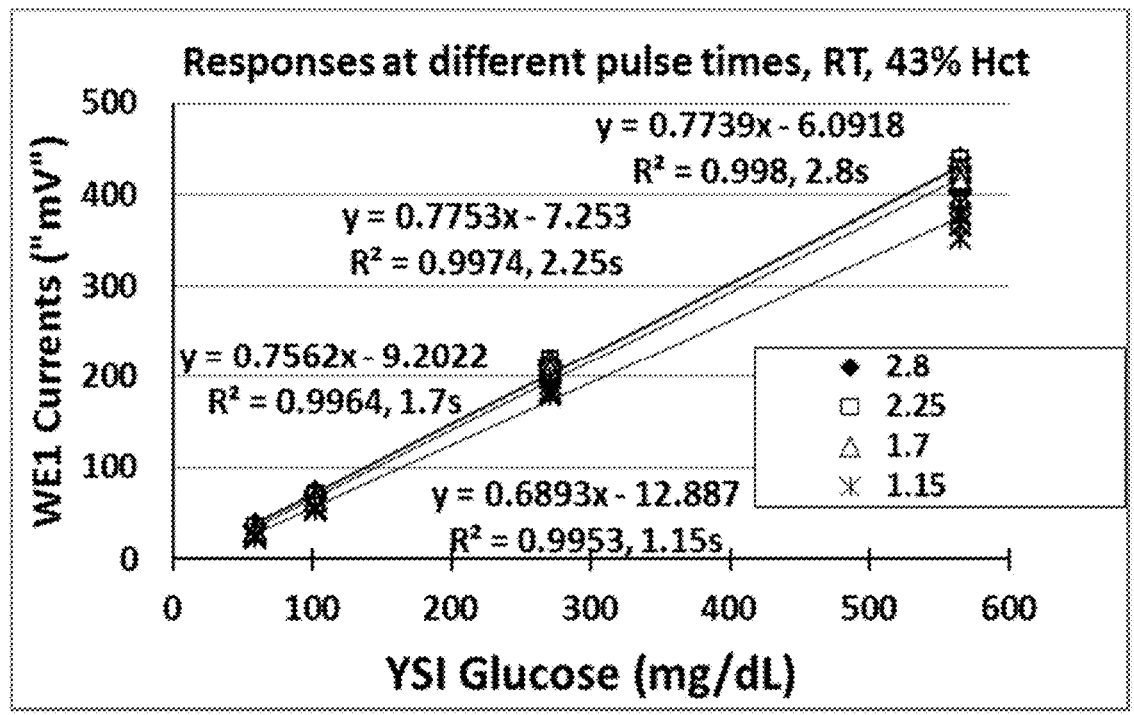
FIG. 10A shows reference correlations for different pulses of the first input signal in FIG. 8A, in accord with aspects of the present disclosure.
Figure 10B:
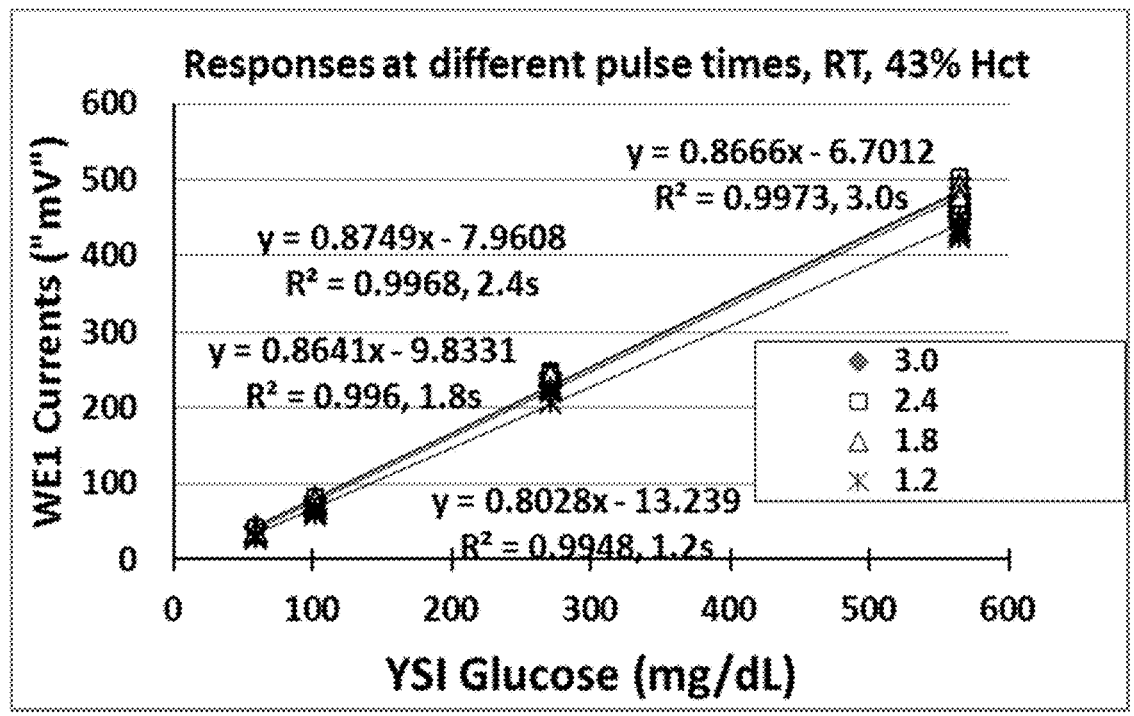
FIG. 10B shows reference correlations for different pulses of the first input signal in FIG. 8B, in accord with aspects of the present disclosure.
Figure 10C:
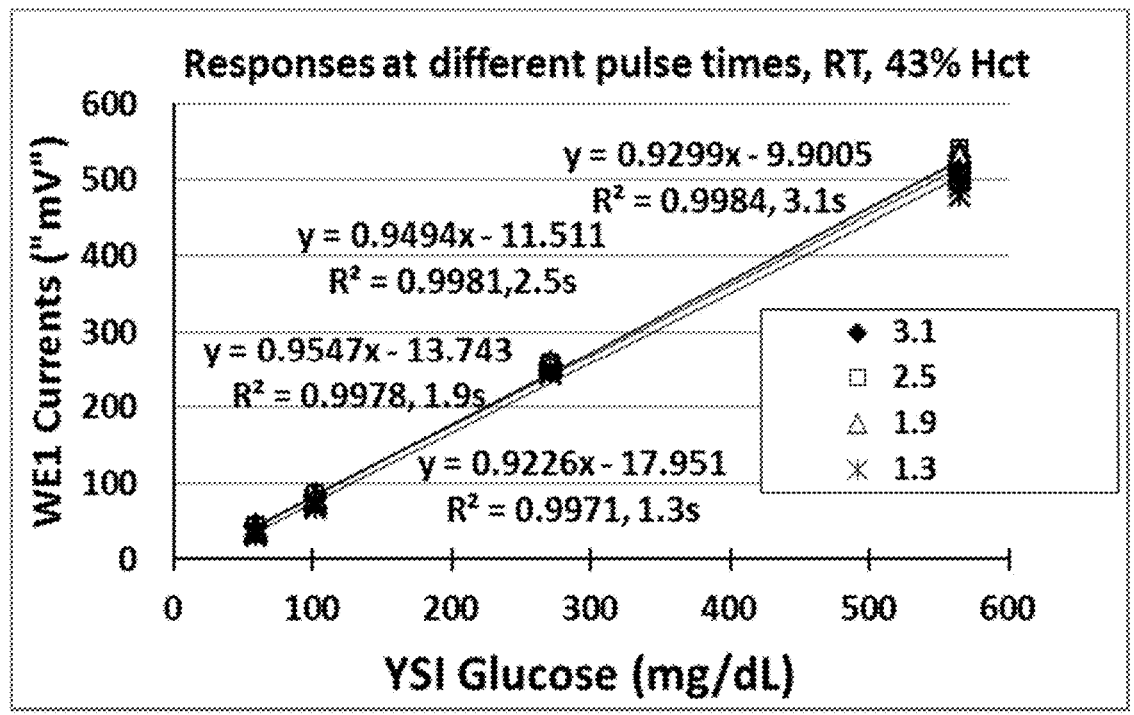
FIG. 10C shows reference correlations for different pulses of the first input signal in FIG. 8C, in accord with aspects of the present disclosure.
Figure 10D:
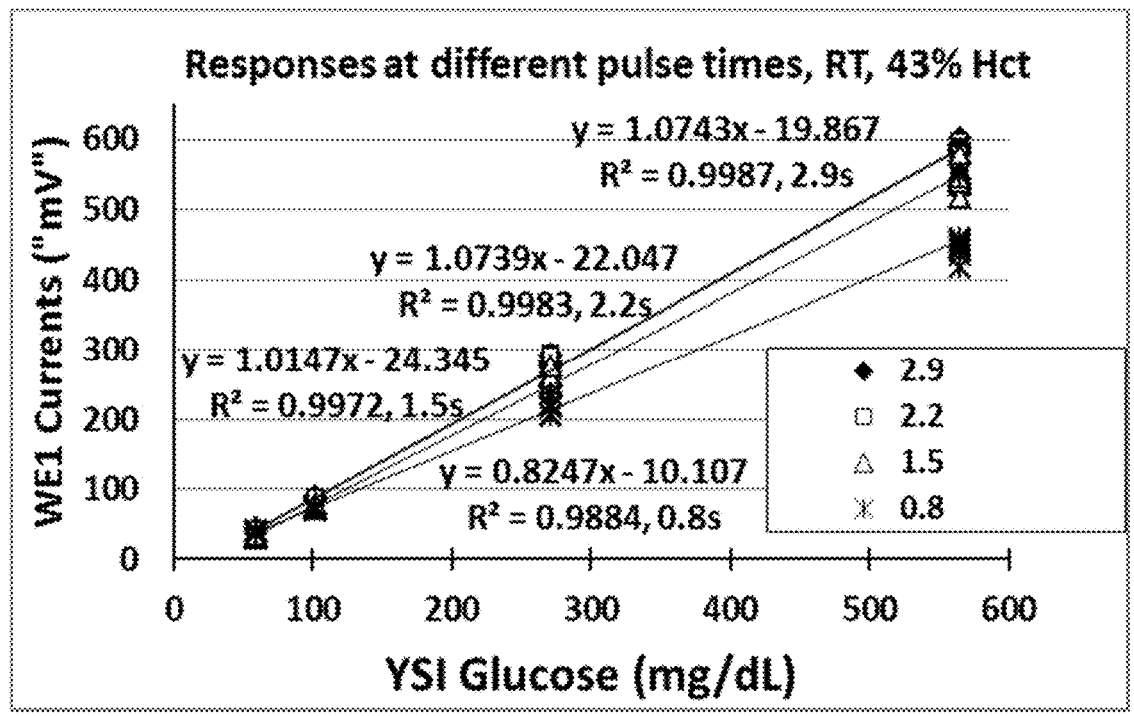
FIG. 10D shows reference correlations for different pulses of the first input signal in FIG. 8D, in accord with aspects of the present disclosure.
Figure 10E:
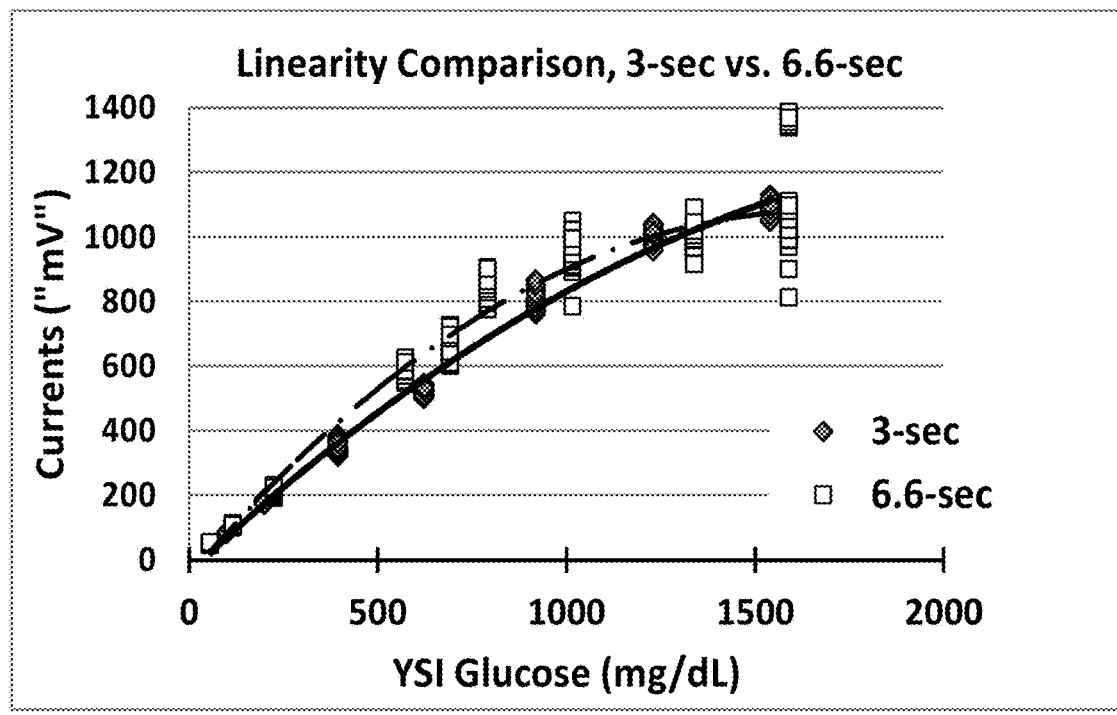
FIG. 10E shows a comparison of the raw signals correlated with reference glucose concentrations for a 3 second potential sequence and a 6.6 second potential sequence, in accord with aspects of the present disclosure.

FIG. 10E shows a comparison of the raw signals correlation with the reference glucose concentrations for 3 s and 6.6 s potential sequences. Both the 3 s and 6.6 s potential sequences had six main pulses at the first electrode with their end points at 3 s and 6.6 s, respectively. It can be seen from FIG. 10E that, while the raw signals from the 6.6 s correlation curves off starting at 700 mg/dL and continues to level off at higher glucose concentrations, the raw signals from the 3 s correlation is linear up to 900 mg/dL and only slightly curves off at higher glucose concentration.

The correlation plots of FIGS. 10A-10E demonstrate that the signals taken from the time at 2.0 s or less are linear with concentration and can be used to indicate the analyte concentration. For better use of G signals, a still more compact pulse sequence having three or more pulses can be implemented. Otherwise, in the case of the present sequences in FIG. 8A-8D, the G signals are used in combination with any of the earlier M indicating signals, with the time ending at about 3 s.

With assay times of less than 2.0 s feasible at similar or improved accuracy and precision, higher linearity can be achieved. With higher linearity, higher concentrations of analyte can be determined based on the consumption of the reagents used in determining the concentration of the analyte occurring over shorter periods of time. Thus, more of the reagents remain for determining the higher concentrations. In the case of glucose, glucose levels as high as 900, 1000, 1100, or 1200 mg/dL can be determined based on biosensor systems of the present disclosure, specifically biosensor systems that implement intertwined first and second input signals.

The conventional wisdom for biosensors is to have overloaded reagent capacity to support the chemical and electrochemical reactions under the normal operation (glucose range, temperature, and hematocrit range, etc.). As the assay time gets significantly shorter, for instance, reduced by 50%, the excess capacity of the reagent is available to support the chemical reaction with higher analyte concentrations. In addition, the conventional wisdom is to allow the chemical and/or electrochemical reactions to reach a stable condition to end the biosensor assay process. While the reagent formulation continues to play an important role in the biosensing process for blood glucose monitoring devices and medical device systems, the recent advancements in signal excitation/generation coupled with sophisticated error compensation methods/algorithms allows for biosensors to make a sampling of the system's signals in a much shorter time than ever before, instead of waiting for the reaction to complete. The present invention further discloses the method of generating signals from the second electrode to augment the error compensation, allowing for determining higher analyte concentrations with equivalent or better accuracy.

All of the first and second input signals described above include excitations or pulses of constant potential applied to the sample via the working electrode 114 and the counter electrode 116, or via the bare electrode 118 and the counter electrode 116. These excitations or pulses are described as amperometric excitations or pulses. However, the excitations or pulses of the first and/or second input signals can be pulses other than constant potential, such as voltammetric excitations or pulses. In some aspects, one or more pulses of the first and/or second input signals can instead be a linear scan pulse, a cyclic voltammetric pulse, an acyclic voltammetric pulse, and the like.

A "cyclic" pulse or excitation refers to a voltammetric excitation combining a linear forward scan and a linear reverse scan, where the scan range includes the oxidation and reduction peaks of a redox couple. For example, varying the potential in a cyclic manner from −0.5 V to +0.5 V and back to −0.5 V is an example of a cyclic scan for the ferricyanide/ferrocyanide redox couple as used in a glucose biosensor system, where both the oxidation and reduction peaks are included in the scan range. Both the forward and reverse scans can be approximated by a series of incremental changes in potential. Thus, applying a change of potential approximating a cyclic change can be considered a cyclic scan.

An "acyclic" pulse or excitation refers to an aspect of a voltammetric excitation including more of one forward or reverse current peak than the other current peak. For example, a scan including forward and reverse linear scans where the forward scan is started at a different voltage than where the reverse scan stops, such as from −0.5 V to +0.5 V and back to +0.25 V, is an example of an acyclic scan. In another example, an acyclic scan can start and end at substantially the same voltage when the scan is started at most +20, +10, or +5 mV away from the formal potential Eo' of a redox couple. In another aspect, an acyclic scan or pulse refers to a voltammetric excitation including forward and reverse linear scans that substantially exclude the oxidation and reduction output current peaks of a redox couple. For example, the excitation can begin, reverse, and end within the diffusion limited condition (DLC) region of a redox couple, thus excluding the oxidation and reduction output current peaks of the couple. Both the forward and reverse scans can be approximated by a series of incremental changes in potential. Thus, applying a change of potential approximating an acyclic change can be considered an acyclic scan.

Figure 11A:
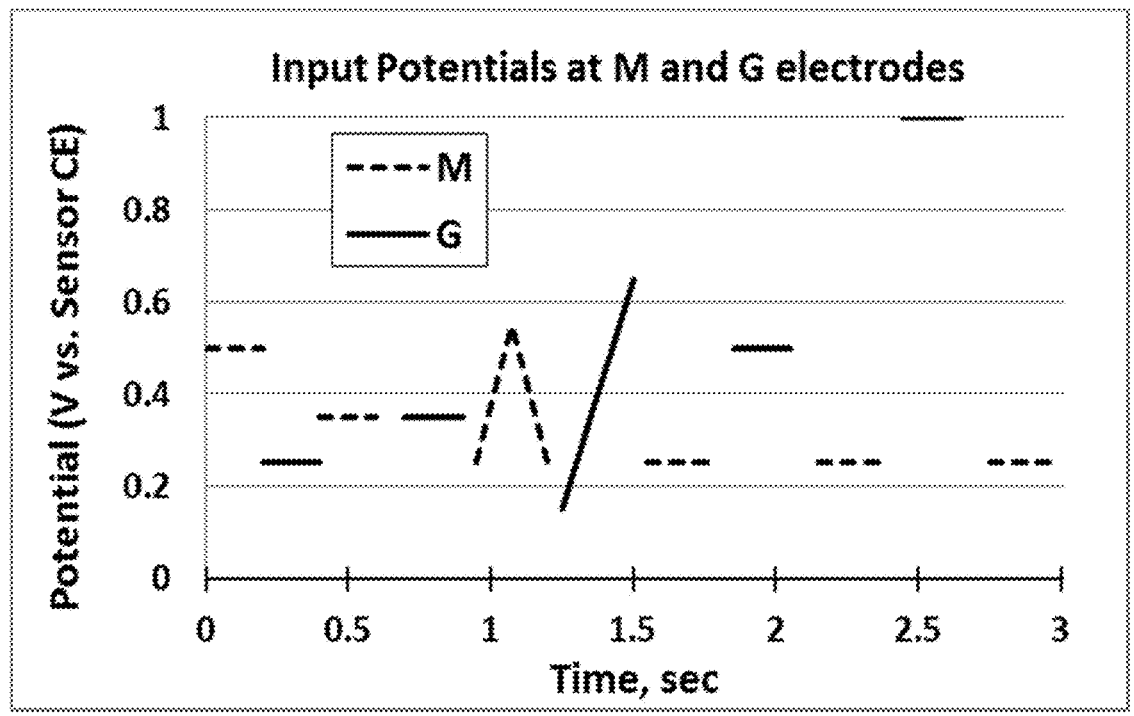
FIG. 11A is a graph illustrating an application of intertwined first and input signals for a biosensor system with pulses that are not all at a constant potential, in accord with additional aspects of the present disclosure.

FIG. 11A is a graph illustrating intertwined input signals for an electrochemical biosensor system, such as the system 100 of FIG. 1, with amperometric and voltammetric pulses, in accord with additional aspects of the present disclosure. More specifically, FIG. 11A shows two input signals, represented by the labels M and G. The first input signal M includes pulses of constant potential applied across the working electrode 114 and the counter electrode 116 in relation to the system 100 of FIG. 1, except that one pulse is an acyclic voltammetric pulse. In total, the first input signal M includes six pulses, which will be referred to here in the order in which they appear from left to right on the graph as $M_1$, $M_2$, $M_3$, $M_4$, $M_5$, and $M_6$. As shown, the pulse $M_1$ has a potential of 0.5 V, the pulse $M_2$ has a potential of 0.35 V, and pulses $M_4$-$M_6$ have potentials of 0.25 V. The pulse $M_3$ is an acyclic voltammetric pulse with a scan rate of 2.4 V/s beginning at 0.25 V, increasing linearly to about 0.55 V, and dropping back down linearly to about 0.25 V.

The second input signal G also includes pulses of constant voltage, but the pulses are applied across the bare electrode 118 and the counter electrode 116, except that one pulse is a linear scan pulse. In total, the second input signal G includes five pulses, $G_1$, $G_2$, $G_3$, $G_4$, and $G_5$. As shown, the pulse $G_1$ has a potential of 0.25 V, the pulse $G_2$ has a potential of 0.35 V, the pulse $G_4$ has a potential of 0.5 V, and the pulse $G_5$ has a potential of 1.0 V. The pulse $G_3$ is a linear scan pulse with a scan rate of about 2 V/s beginning at about 0.15 V and increasing linearly to about 0.65 V.

Figure 11B:
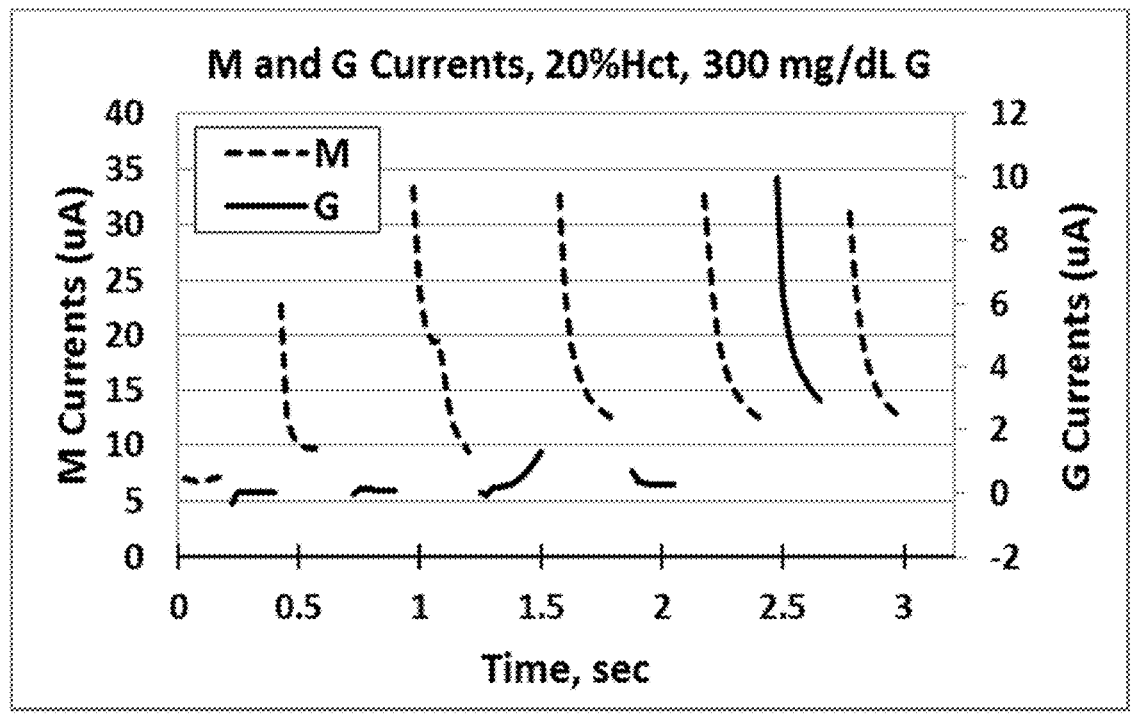
FIG. 11B is a graph illustrating intertwined first and second output signals in response to the intertwined first and second input signals of FIG. 11A, respectively, in accord with aspects of the present disclosure.

FIG. 11B is a graph illustrating intertwined first and second output signals in response to the intertwined first and second input signals of FIG. 11A, in accord with aspects of the present disclosure. The graph is in response to the first and second input signals being applied to a WB sample of 300 mg/dL of glucose at 20% Hct and room temperature. Each trace in response to each pulse of the first and second input signals can be one or more output currents, such as one current, two currents, three currents, four currents, five currents, six currents, seven currents, eight currents, nine currents, ten currents, and the like.

Figure 11C:
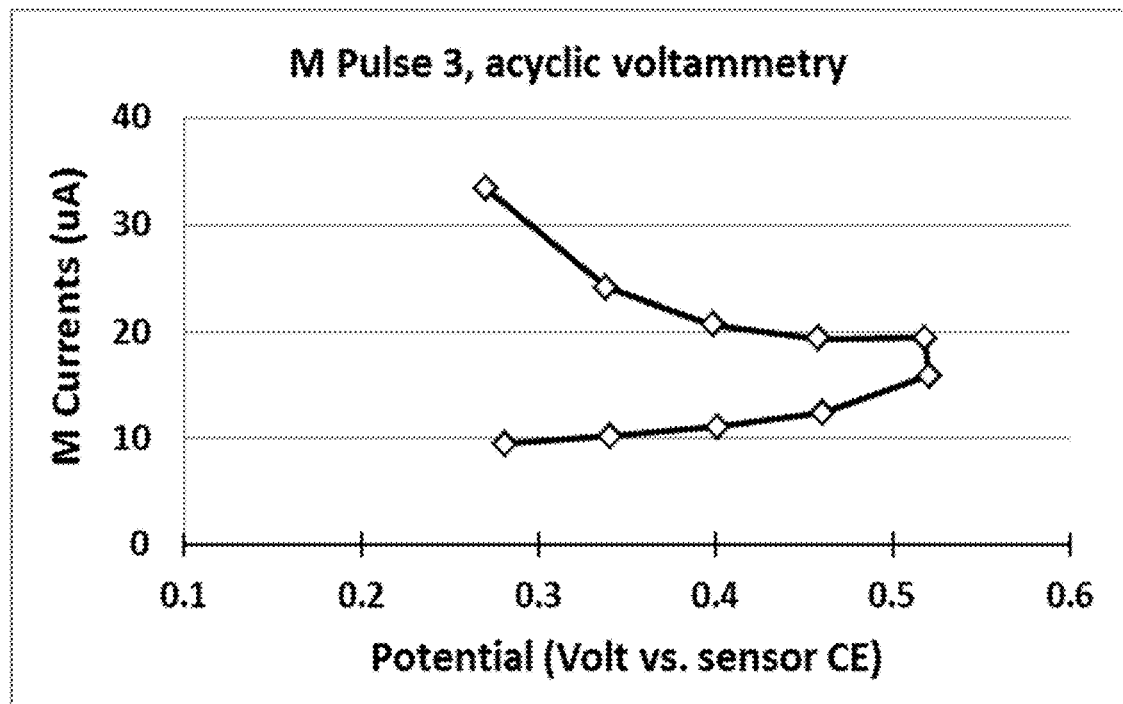
FIG. 11C is a graph illustrating the currents measured in response to the acyclic voltammetric pulse $M_3$ of the first input signal of FIG. 11A in the form of a voltammogram, in accord with aspects of the present disclosure.

FIG. 11C is a graph illustrating the output currents in response to the acyclic voltammetric pulse $M_3$ of the first input signal, plotted as voltammogram, in accord with aspects of the present disclosure. The electronic sampling rate used in acquiring the data shown in FIG. 11C is 40 data points per second. As shown, ten currents were measured as the voltage applied across the working electrode 114 and the counter electrode 116 was varied between 0.25 V to 0.55 V and back to 0.25 V.

Figure 11D:
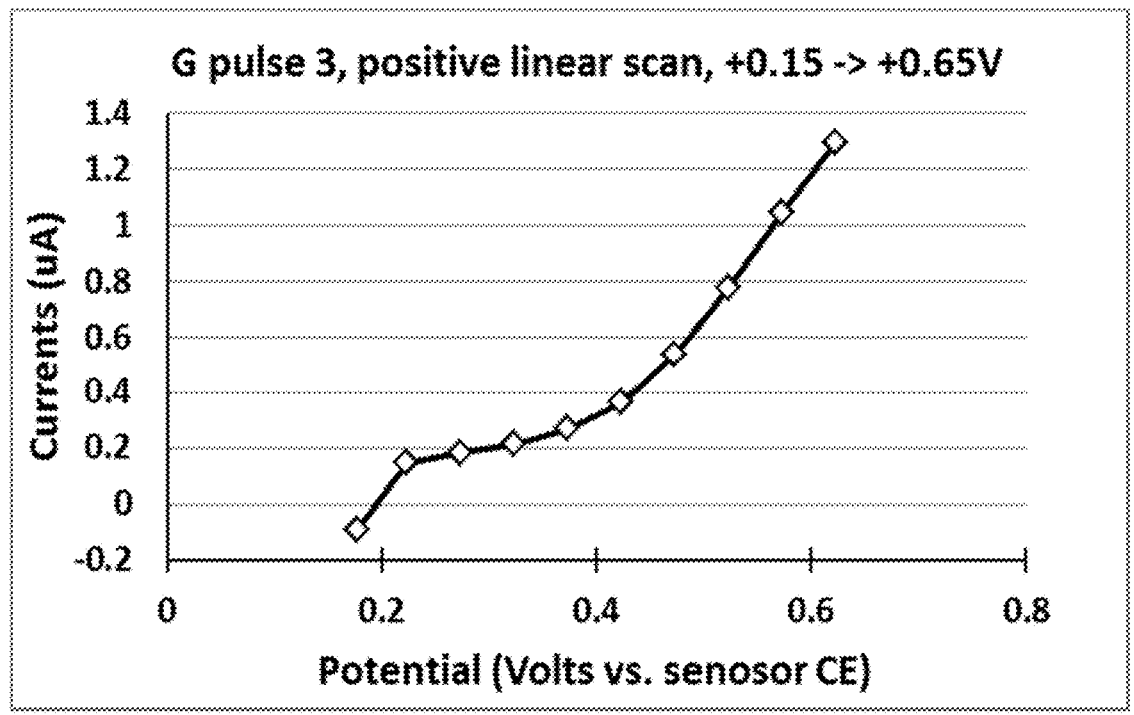
FIG. 11D is a graph illustrating the currents measured in response to the linear scan pulse $G_3$ of the second input signal of FIG. 11B in the form of a voltammogram, in accord with aspects of the present disclosure.

FIG. 11D is a graph illustrating the currents in response to the linear scan pulse $G_3$ of the second input signal, plotted as voltammogram, in accord with aspects of the present disclosure. The electronic sampling rate used in acquiring the data shown in FIG. 11D is 40 data points per second. As shown, 10 currents were measured as the voltage applied across the bare electrode 118 and the counter electrode 116 was linearly scanned between 0.15 V and 0.65 V.

Figure 12A:
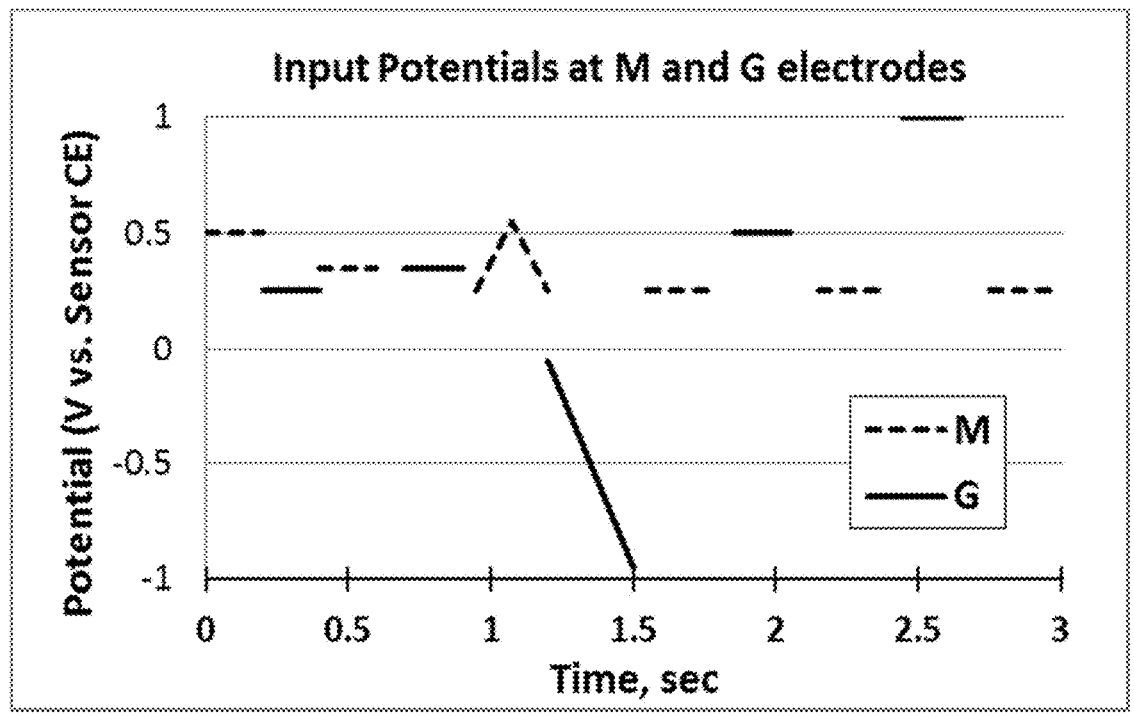
FIG. 12A is a graph illustrating an application of intertwined first and second input signals for a biosensor system with pulses that are not all at a constant potential, in accord with additional aspects of the present disclosure.

FIG. 12A is another graph illustrating intertwined input signals for an electrochemical biosensor system, such as the system 100 of FIG. 1, with amperometric and voltammetric pulses, in accord with additional aspects of the present disclosure. More specifically, FIG. 12A shows two input signals, represented by the labels M and G. The first input signal M is identical to the first input signal M of FIG. 11A. The second input signal G is identical to the second input signal G of FIG. 11A except that the linear scan pulse $G_3$ has a scan rate of 3.0 V/s that begins at about −0.05 V and ends at about −0.95 V.

Figure 12B:
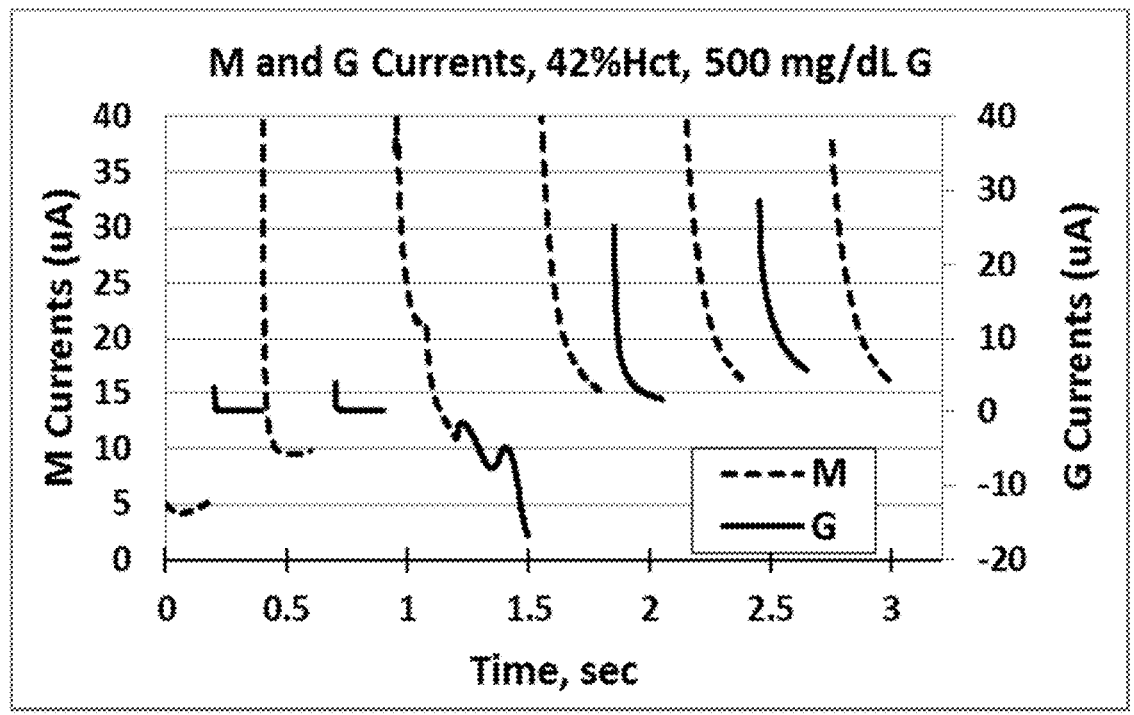
FIG. 12B is a graph illustrating intertwined first and second output signals in response to the intertwined first and second input signals of FIG. 12A, in accord with aspects of the present disclosure.

FIG. 12B is a graph illustrating intertwined first and second output signals in response to the intertwined first and second input signals of FIG. 12A, in accord with aspects of the present disclosure. The graph is in response to the first and second input signals being applied to a WB sample of 500 mg/dL of glucose at 42% Hct and room temperature. Each trace in response to each pulse of the first and second input signals can be one or more output currents, such as one current, two currents, three currents, four currents, five currents, six currents, seven currents, eight currents, nine currents, ten currents, and the like.

Figure 12C:
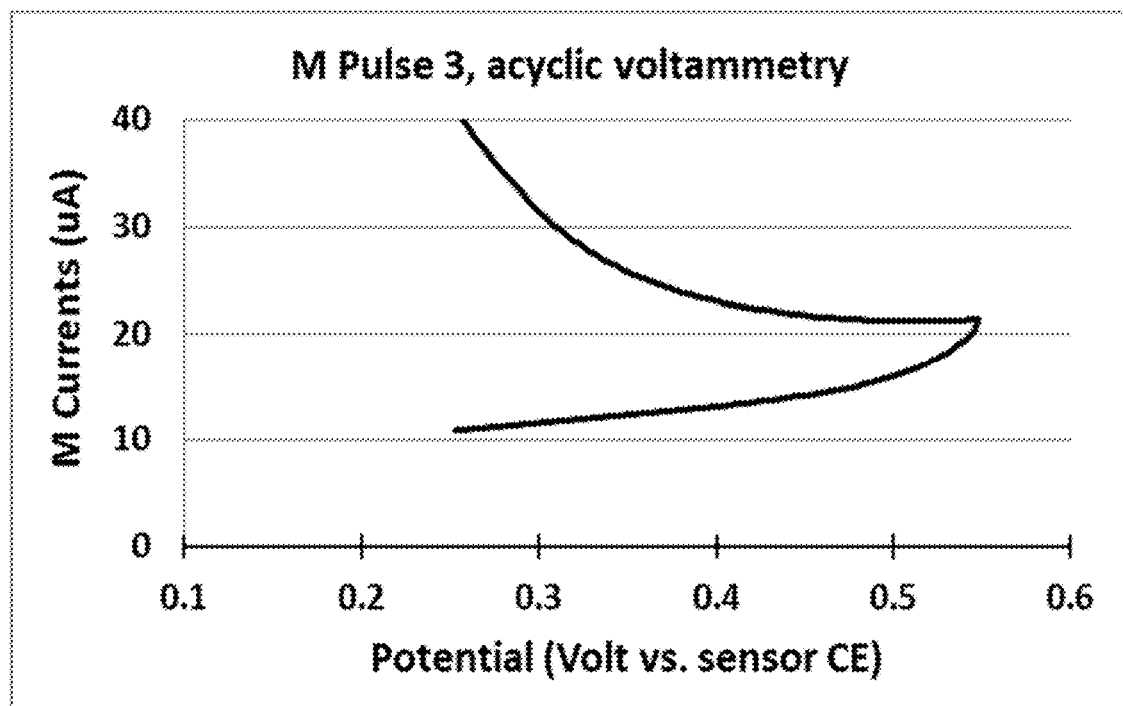
FIG. 12C is a graph illustrating the currents measured in response to the acyclic voltammetric pulse $M_3$ of the first input signal of FIG. 12A, in accord with aspects of the present disclosure.

FIG. 12C is a graph illustrating the currents in response to the acyclic voltammetric pulse $M_3$ of the first input signal of FIG. 12A in the form of a voltammogram, in accord with aspects of the present disclosure. The data sampling rate used in acquiring the data shown in FIG. 12C was 500 data points per second. According to this data sampling rate, many more data points were acquired at the same time period, providing a nearly continuous output current trace. However, the trace is a solid line indicating that any number of currents can be taken in response to the pulse $M_3$ of the first input signal in FIG. 12A as the voltage was applied across the working electrode 114 and the counter electrode 116 between 0.25 V to 0.55 V and back to 0.25 V.

Figure 12D:
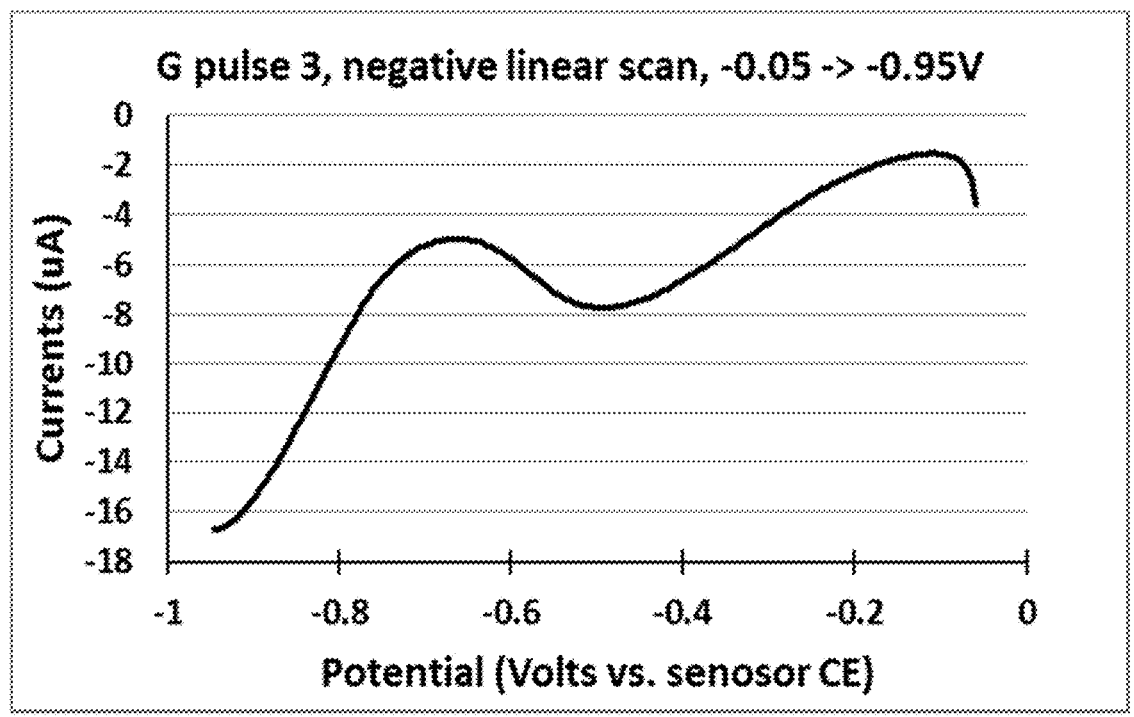
FIG. 12D is a graph illustrating the currents measured in response to the linear scan pulse $G_3$ of the second input signal of FIG. 12A in the form of a voltammogram, in accord with aspects of the present disclosure.

FIG. 12D is a graph illustrating the currents in response to the linear scan pulse $G_3$ of the second input signal of FIG. 12A in the form of a voltammogram, in accord with aspects of the present disclosure. Similar to FIG. 12C, the data sampling rate used in acquiring the data shown in FIG. 12D was 500 data points per second. According to this data sampling rate, many more data points were acquired at the same time period, providing a nearly continuous output current trace. However, the trace is a solid line indicating that any number of currents can be taken in response to the pulse $G_3$ of the second input signal in FIG. 12A as the voltage applied across the bare electrode 118 and the counter electrode 116 was linearly scanned between −0.05 V and −0.95 V.

Based on the first and second intertwined output signals, one or more error parameters as described above can be generated (e.g., calculated, computed, etc.) and used in error compensation equations for determining the concentration of an analyte in a sample. The error parameters based on the second output signal, although responsive to species in the sample besides the target analyte, provide additional information regarding the electrochemical window of the sample that allows for more accurate, precise, and faster determinations of the analyte concentrations than conventional methods. Moreover, despite the second input signal probing redox potentials that are lower or higher than the redox potentials associated with the analyte, mediator, or other measurable species associated with the analyte, the corresponding second output signal still provides information that aids in the analyte concentration determination.

Figure 13:
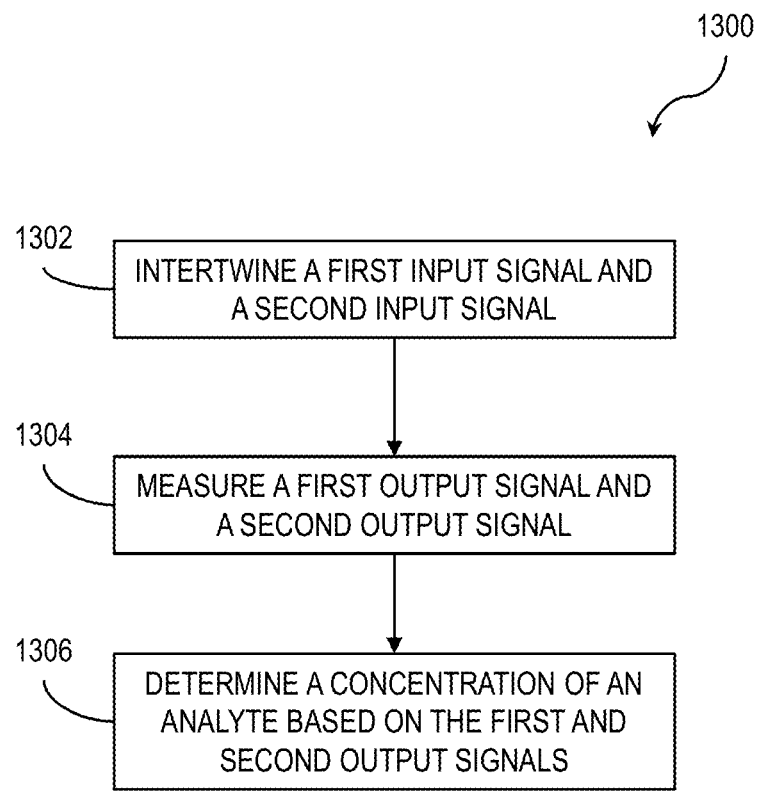
FIG. 13 is a flowchart of a process for determining a concentration of an analyte based on intertwined input signals, in accord with aspects of the present disclosure.

FIG. 13 is a flowchart of a process 1300 for determining a concentration of an analyte based on intertwined input signals, in accord with aspects of the present disclosure. The process 1300 can be performed by a biosensor system, such as the biosensor system 100 discussed above. In specific aspects, the biosensor system performing the process 1300 can be a device for determining the concentration of glucose in a blood sample, such as a WB sample, and the target analyte that is the focus of the analysis can be glucose.

At step 1302, first and second intertwined input signals are applied to a sample according to the above concepts. The first input signal is applied to the sample via a first electrode having a reagent, and the second input signal is applied to the sample via a second electrode lacking a reagent. In some aspects, the second electrode lacks any reagent that facilitates oxidation of the target analyte. However, in some aspects, the second electrode can include one or more reagents that do not facilitate oxidation of the analyte, but may facilitate oxidation of other species within the sample. In the case of glucose as the analyte in the sample, the reagent of the first electrode can include an oxidoreductase. Specifically, the reagent can be a glucose oxidase enzyme, a glucose dehydrogenase enzyme, or a combination thereof. The sample can be a WB sample that contains the glucose. Alternatively, the sample can be a derivative of a WB sample.

The application of the intertwined first and second input signals includes applying to the sample, via the first electrode, the first input signal having at least two excitations or pulses and at least one relaxation of the first electrode, and applying to the sample, via the second electrode, the second input signal having at least one excitation or pulse and at least one relaxation of the second electrode. The at least two excitations (or pulses) of the first input signal can be any type of excitation as discussed above, such as a constant voltage pulse, a linear scan pulse, a cyclic voltammetric pulse, an acyclic voltammetric pulse, and the like, and/or combinations thereof. The at least one excitation of the second input signal can be any type of excitation as discussed above, such as a constant voltage pulse, a linear scan pulse, a cyclic voltammetric pulse, an acyclic voltammetric pulse, and the like, and/or combinations thereof. The first and second input signals are applied intertwined such that the excitations of the first input signal are nonconcurrent with and separated from each other by the excitation(s) of the second input signal. The first and second electrode can be in electrically open states during the relaxations of each respective electrode. Alternatively, a minimal potential can be applied across the first or second electrode during a relaxation of the particular electrode so as to not be in an open state but otherwise not affect, or predicatively affect, the other of the first or second electrode during excitations of the sample.

As described as at least two excitations and at least one excitation of the first input signal and the second input signal, respectively, in some aspects, the first input signal and the second input signal can have more excitations. For example, the first input signal can have three, four, five, six, seven, eight, nine, ten, or more excitations or pulses applied to the sample during a determination of the concentration of the analyte within the sample. Similarly, the second input signal can have two, three, four, five, six, seven, eight, nine, ten, or more excitations or pulses applied to the sample during a determination of the concentration of the analyte within the sample, and the number of excitations can be the same or different than the number of excitations of the first input signal.

All of the excitations of the first input signal can be of the same intensity or amplitude, such as the same voltage or range of voltages. In some aspects, all of the excitations of the first input signal can be of the same intensity after an initial number of excitations that prepare the sample for analysis. For example, a first excitation of the first input signal can be a constant 0.5 V excitation, a second excitation of the first input signal can be a constant 0.35 V excitation, and the remaining excitations of the first input signal can be constant 0.25 V excitations. However, the excitations can be various other types and intensities of excitations, as further described above.

All of the excitations of the second input signal can be of the same intensity, of an increasing intensity, of a decreasing intensity, or of a decreasing and increasing intensity. By way of example, a first excitation of the second input signal can be a constant 0.25 V excitation, or a voltage equivalent to the pulse voltages of the later working electrode pulses for analyte detection. A second excitation of the second input signal can be a constant 0.35 V excitation, or a voltage in the order of 50-200 mV higher than the first pulse. A third excitation of the second input signal can be a constant 0.5 V excitation, or a voltage in the order of 200-400 mV higher than the first pulse. A fourth excitation of the second input signal can be a constant 1.0 V excitation, or a voltage in the order of 500-1000 mV higher than the first pulse, or a voltage even further away from the first pulse such as 1000-1800 mV. According to the above-described voltages, the second electrode pulses probe the near and far fields of the redox potential windows for the presence of interference species and/or endogenous species in the sample and sample profiling. These interference species and/or endogenous species may have direct or indirect effects on the output signals of the working electrode pulses. The output signals of the bare electrode pulses augment the error compensations through error parameters and error detections. However, the excitations can be various other types and intensities of excitations, as further described above.

The widths or durations of the excitations and pulses of the first and second input signals can be constant, or can vary, both with respect to other excitations within the same input signal and with respect to other excitations within the other input signal. Further, in some aspects, more than one excitation of the second input signal can occur between two adjacent excitations of the first input signal.

In some aspects, an additional or third input signal can be applied to the sample, either as a separate input signal or as part of the second input signal. The additional input signal can be a large amplitude excitation pulse to the second electrode having no added reagent for sensing the WB hematocrit level. In addition, other characteristics of the first and second input signals can vary as described above.

At step 1304, a first output signal responsive to the first input signal and a second output signal responsive to the second input signal are measured at different times or as the respective first and second input signal are applied. The first and second output signals are responses to the first and second input signals, respectively. The first and second output signals include measurements of the currents responsive to the excitations of the first and second input signals, respectively. In particular, the first output signal is directly responsive to the concentration of the analyte in the sample based on the first electrode by which the first input signal is applied to the sample having the one or more reagents. Accordingly, the first output signal is responsive to a redox reaction of the analyte, either directly or indirectly, such as through a mediator or other type of measureable species related to the analyte concentration. In contrast, the second output signal is not responsive to the concentration of the same analyte in the sample targeted by the first electrode and the first input signal, based on the second or bare electrode by which the second input signal is applied to the sample not having the one or more reagents of the first or working electrode.

For each excitation of the first and second input signals, one or more currents can be measured in generating the first and second output signals. For example, one, two, three, four, five, six, seven, eight, nine, ten, or more output currents can be measured in response to each of the excitations of the first and second input signals. The number of output currents measured can be the same or different for each excitation of the first and second input signals.

In response to the third input signal for the hematocrit, one or more currents can be measured. These currents can be considered a third output signal or part of the second output signal.

At step 1306, the concentration of the analyte is determined based on at least the first output signal and the second output signal. The first and second output signals are analyzed with respect to the target analyte concentration in relation to the reference correlation and the error parameters in relation to error compensations and/or error detection for determining the concentration of the analyte. One or more error parameters are generated based on the first output signal, the second output signal, the second output signal compared to the first output signal, or a combination thereof. The error parameters can include ratios of the currents of the first output signal, the second output signal, or the first output signal compared to the second output signal. The one or more error parameters can include intra-pulse ratios that are based on currents related to a single pulse of the first or second output signal, inter-pulse ratios that are based on currents related two different pulses of the first or second output signal, or intertwined ratios that are based on currents related to two pulses, one pulse being from the first output signal and one pulse being from the second output signal.

In some aspects, one or more error parameters can be based on currents measured in response to the third output signal related to the hematocrit level. These error parameters can be based on ratios that include the currents from the additional output signal for the hematocrit level, either alone or in combination with one or more currents from the first and/or second output signal.

In some aspects for determining the concentration of the analyte in the sample, a reference correlation for the analyte with the first output signal from the first electrode having the reagent can be established. A $\Delta S$ value can be determined from one or more pre-determined compensation functions stored in the memory of the biosensor system and generated as a result of factory calibration and regression of compensation functions. The error parameters calculated from the first and/or second output signals can be entered into the pre-determined compensation functions. The error parameters contribute to determine an accurate analyte concentration by compensating for biosensor system error resulted from one or more error contributors by adjusting the reference correlation through the slope deviation $\Delta S$ value, or a combination thereof. Based on having the error parameters generated for the second output signal, the second output signal relative to the first output signal, such as in the case of intertwined error parameters, or a combination thereof, the benefits according to the present disclosure can be achieved as compared to conventional biosensor systems that do not include intertwined first and second input signals.

Output signals from the second electrode provide additional error parameters to be entered into the compensation equations. These error parameters may not be specific about the individual species, but can represent categorically the types of interference species that can be present during the analyte determination process from the WB samples. Because the WB samples vary from different end users with different levels of interference species, the first electrode alone having the target reagent for the analyte cannot provide the interference information independent of the target analyte. Thus, the error associated with interference species cannot be addressed by the first electrode output signals, and the second electrode having no added reagent, or having no reagent for the targeted analyte, will provide the interference information. Among other benefits of the second electrode with the second output signals, some of the benefits include assay times shorter than that of conventional biosensor systems with the same or even improved accuracy. For example, in some aspects, the benefits include assay times of about 3.5 s with a 5%, 10%, 20%, 30%, or 40% improvement in accuracy as compared to conventional biosensor systems that do not include intertwined first and second input signals as described herein. In some aspects, the benefits include assay times of about 3.2 s with a 5%, 10%, 20%, 30%, or 40% improvement in accuracy as compared to conventional biosensor systems that do not include intertwined first and second input signals as described herein. In some aspects, the benefits include assay times of about 3.0 s with a 5%, 10%, 20%, 30%, or 40% improvement in accuracy as compared to conventional biosensor systems that do not include intertwined first and second input signals as described herein. In some aspects, the benefits include assay times of 2.2 s with a 5%, 10%, 20%, 30%, or 40% improvement in accuracy as compared to conventional biosensor systems that do not include intertwined first and second input signals as described herein. In some aspects, the benefits include a %-bias of the determined analyte concentration being ±10%, ±5%, ±4%, ±3%, ±2%, ±1%, or even better, for the same or shorter assay times, such as 3.5 s, 3.2 s, 3.0 s, 2.8 s, 2.6 s, 2.4 s, 2.2 s assay times, or even less.

Table 2 below provides exemplary results respective to a particular donor study with compensation equations having the G-terms (or terms generated based on a second working electrode) and having no G-terms. Two exemplary complex function equations with and without the G-terms input into the regressions are shown below (derived from lab data with variations in reference glucose, temperatures, and hematocrit levels). These two compensation functions were applied to raw donor study data. Compensation takes the form of $G_{comp}=(I-Int_{cal})/(S_{cal}*(1+\Delta S/S))$. Bias/%-bias values were calculated by $(G_{comp}-YSI)$ for YSI<100 mg/dL and by $100\%*(G_{comp}-YSI)/YSI$ for YSI≥100 mg/dL. Further, compensation is achieved by adjusting the slope of the reference correlation by the predictor function (complex index function) $\Delta S/S=f(Rx, \ldots)$, which is the calculated normalized slope deviation $\Delta S/S$ from the prediction function as a result of multi-variable regression. The mean and standard deviation (SD) values were calculated from the sum of 600 data points (duplicate data of each sample) in an internal donor study of self-testing from six lots.

It can be seen from Table 2 that, for compensation results, the SD value with the G-terms in the compensation function is about 0.2 SD units smaller, or the system error is reduced with more power than that without the G-terms input into the compensation function. This translates into more than 10% improvement for the ±5% accuracy (68.6% within ±5% for G-terms versus 60.5% within ±5% for no G-terms). For the accuracy of ±10% level, there is an improvement of two percentage points with the G-terms for the compensation function with the G-terms (95.4% within ±10% for G-terms versus 93.4% within ±10% for no G-terms). These results highlight the importance of the G pulse signals in the continuous drive to better accuracy for BGM systems.

TABLE 2

Comparison of compensation results with and without terms generated based on the second electrode (G-terms).

| | Compensation Results | | | | |
|---|---|---|---|---|---|
| | Mean | SD | ±5% | ±10% | ±12.5% |
| With G-terms | −0.53 | 4.76 | 68.6 | 95.4 | 97.5 |
| No G-terms | −1.59 | 4.95 | 60.5 | 93.4 | 97.5 |

The exemplary equation for the compensation complex index function with G-terms was:

$$\Delta S/S = -1.2778073 + 0.0665729*T - 3.532e-4*G*T*H - 2.555e-4*G*T + 0.0338002*G*H + 0.492732*R_2 - 0.1877257*R_7 + 0.1574192*RG_3 + 0.0459172*R_{42} - 0.3831424*R_{65} + 0.0109147*RG_{43} - 0.0032894*RHG_4 - 4.144e-4*M_6G_2 + 0.107479*M_6G_4 - 0.0014855*G*R_5 - 0.0439957*G*RG_{43} + 0.0534208*G*M_3G_4 - 0.0734538*H*R_3 + 0.2158373*H*R_6 + 0.3208298*H*R_{32} - 0.1284548*H*R_{62} + 0.1042826*H*R_{63} - 0.0099486*H*RG_{43} + 0.0066875*H*M_5G_3 - 0.0044375*H*M_6G_3 - 0.0280382*T*R_2 + 0.0208591*T*R_3 + 0.0299228*T*R_5 - 0.0834963*T*R_6 - 0.0085322*T*R_{42} - 1.7689934*T*RG_{32} + 0.2168343*T*RG_{42} + 4.6293673*T*M_3G_4 - 10.50741*T*M_5G_4 - 0.1451554*G*T*R_5 + 0.211731*G*T*R_6 + 0.1942922*G*T*RG_4 + 0.038012*G*T*RG_4 + 0.1131831*G*T*R_{63} + 0.0010882*G*T*RG_{32} - 3.79e-5*G*T*M_2G_3 + 0.0041538*G*T*M_5G_4 - 0.0013806*G*H*R_4 + 0.0014286*G*H*R_6 - 9.826e-4*G*H*R_{43} - 0.0018126*G*H*R_{64} - 0.0079612*G*H*M_4G_4 + 2.341e-4*G*T*H*R_7 + 1.894e-4*G*T*H*RHG_4,$$

and the exemplary equation for the compensation complex function without G-terms was:

$$\Delta S/S = -0.5188525 - 0.0665706*T + 0.0246863*G*H + 0.4643401*R_2 - 0.3418844*R_6 - 0.8772739*R_{21} + 0.1577033*R_{61} + 0.3132972*R_{64} - 1.0421636*R_{65} + 0.0033468*G*R_2 + 0.0018*G*R_3 - 0.003074*G*R_6 - 0.1405099*H*R_3 + 0.7219722*H*R_6 + 0.3740353*H*R_{21} + 0.4479624*H*R_{32} - 0.7599627*H*R_{54} - 0.1496064*H*R_{61} - 0.1444729*H*R_{62} + 0.3544145*H*R_{63} - 0.0318846*T*R_2 + 0.0220872*T*R_3 + 0.0320866*T*R_5 - 0.0930098*T*R_6 - 0.0166616*T*R_{21} + 0.0244054*T*R_{31} + 0.0436963*T*R_{32} - 0.121012*T*R_{42} + 0.1420069*T*R_{43} + 0.0657513*T*R_{52} - 0.1230718*T*R_{63} + 0.1249769*T*R_{64} - 0.1765913*G*T*R_2 - 0.3179064*G*T*R_5 + 0.454599*G*T*R_6 + 0.1087889*G*T*R_{31} - 0.0798451*G*T*R_{41} - 0.0698054*G*T*R_{43} - 0.0689099*G*T*R_{62} + 0.3649943*G*T*R_{63} - 0.2709868*G*T*R_{64} + 6.892e-4*G*H*R_2 - 0.0012431*G*H*R_3 - 6.448e-4*G*H*R_{21} - 6.364e-4*G*H*R_{32} + 3.002e-4*G*H*R_{61} - 0.0012672*G*H*R_{63}$$

where $G=G_{raw}=(I-Int)/Scal$ where I is the current, Int is omitted in the calculation; Scal is the system calibration slope; H is the ending current from the 2.5 V Hct pulse; and G, T, and H represent the raw glucose value, the temperature, and the hematocrit signal, respectively. However, the above equations are merely exemplary for the compensation complex function for purposes of comparison between G-terms being present and no G-terms being present, and the present disclosure is not intended to be limited to only these two particular equations.

In addition to providing error parameters for adjusting the compensation equations in calculating the concentration of an analyte in a sample, the second input signal, alone or in combination with the first input signal, can provide other functionality and/or information for a biosensor system, such as the biosensor system 100. The additional functionality can include identifying the sample types or differentiating other sample types from the WB sample where the majority of glucose measurements apply. In particular, the auto-detection of control solutions that are used with the biosensor systems is very important. Other additional functionality can include the measurement and/or identification of oxidizable species within the detection window in a sample that are unrelated to the target analyte, sample profiling, or combinations thereof.

Control solutions in an established biosensor system, such as CONTOUR® NEXT by Ascensia Diabetes Care of Parsippany, N.J., are important by providing instant verification of the system's functionality. In the past twenty years, healthcare innovative solutions have advanced to a point where automatic recognition of the controls against the WB samples has become an integral part of the medical device system for data processing and analysis, such as data averaging.

Furthermore, in the case of a blood glucose monitor (BGM) system connecting to an insulin pump, the control reading should be securely identified so as not to be treated as a WB glucose reading, which would otherwise affect the therapeutic decision by the pump. In yet another example of the auto-detection, there is a need to detect the control solutions belonging to one system against the control solutions for another system in case the end-user uses a different control solution by mistake.

A past method to address control solutions has been to include some oxidizable species in the control at a potential higher than that for the oxidation of the biosensor system's mediator. The added species is referred as a control marker. Using the method of two potentials, one potential being a low potential for the analyte concentration determination and one potential being a high potential for detecting the added marker, the index value from the currents at these two potentials are compared with one or more thresholds for differentiating the sample type, i.e., between a control and a WB sample. However, this methodology has limitations, one of which being the need to add the control marker. Based on the concepts of the present disclosure, multiple parameters can be used for differentiating sample types and in particular for differentiating the control from WB samples based on the pulses or excitations of the second input signal.

One parameter that can be the basis for differentiating a control from a WB sample is the first output current (i.e., $i_{G1,1}$) in response to the first (excitation) pulse of the second input signal when the first pulse is at 0.25 V across the bare electrode 118 and the counter electrode 116. The currents $i_{G1,1}$ for WB samples (e.g., glucose ranging from low to high, temperatures ranging from 5-45° C., and hematocrit values ranging from 0-70%) are positive in response to the second input signal pulse at 0.25 V. In contrast, the currents $i_{G1,1}$ for controls in response to the second input signal pulse at 0.25 V are generally negative. Accordingly, a threshold near zero can be used for differentiation, or the polarity switching of the current $i_{G1,1}$ can be used to distinguish between a control and a WB sample.

Figure 14A:
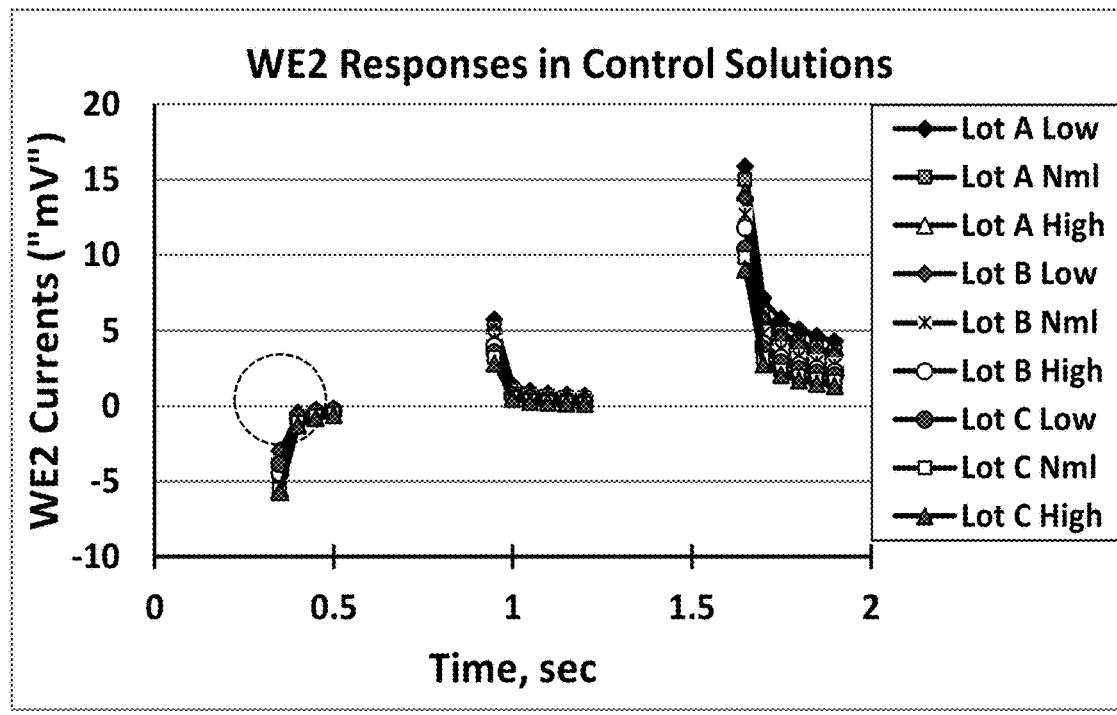
FIG. 14A is a graph illustrating the currents measured in response to the first through third pulses of the second input signal in FIG. 8D applied to various controls, in accord with aspects of the present disclosure.
Figure 14B:
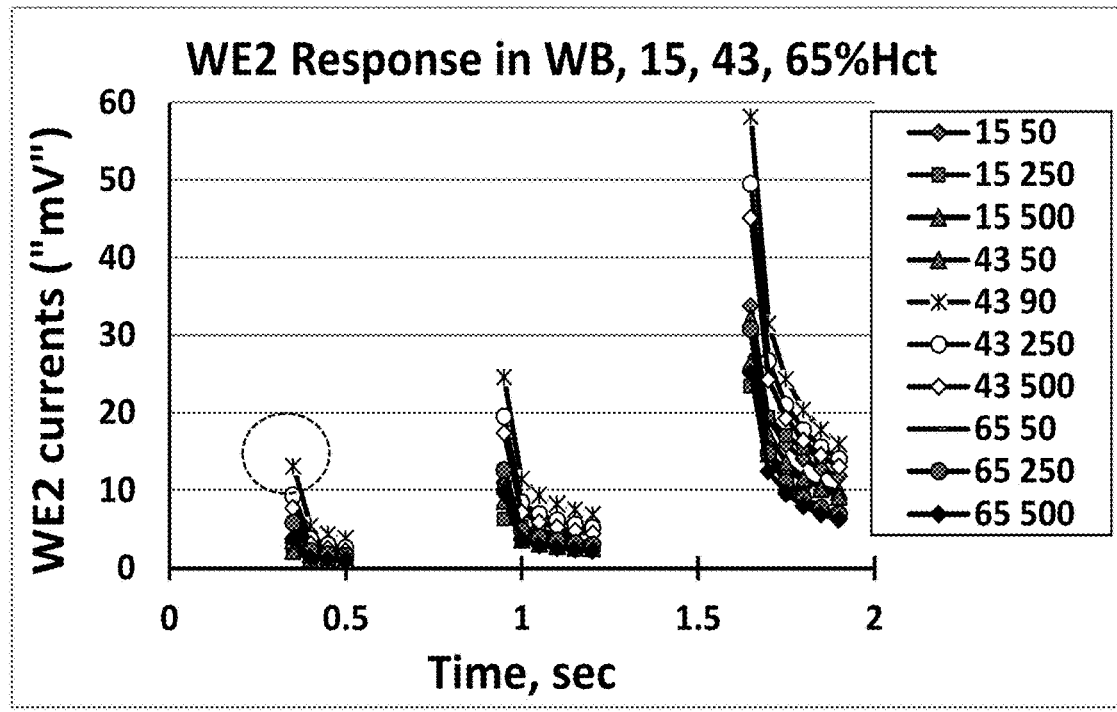
FIG. 14B is a graph illustrating the currents measured in response to the first through third pulses of the second input signal in FIG. 8D applied to various WB samples, in accord with aspects of the present disclosure.

FIG. 14A is a graph illustrating the current measurements in response to the first through third pulses of the second input signal in FIG. 8D applied to various controls, in accord with aspects of the present disclosure. The various controls have low (indicating about 45 mg/dL glucose), normal (indicating about 110 mg/dL glucose), or high (indicating about 300 mg/dL) glucose levels and are from three different lots of controls, indicated by Lot A, B, or C. FIG. 14B is a graph illustrating the currents measured in response to the first through third pulses of the second input signal in FIG. 8D applied to various WB samples, in accord with aspects of the present disclosure. The various WB samples have varying hematocrit levels of 15%, 43%, or 65% and varying glucose concentrations of 50, 90, 250, or 500 mg/dL.

Figure 14C:
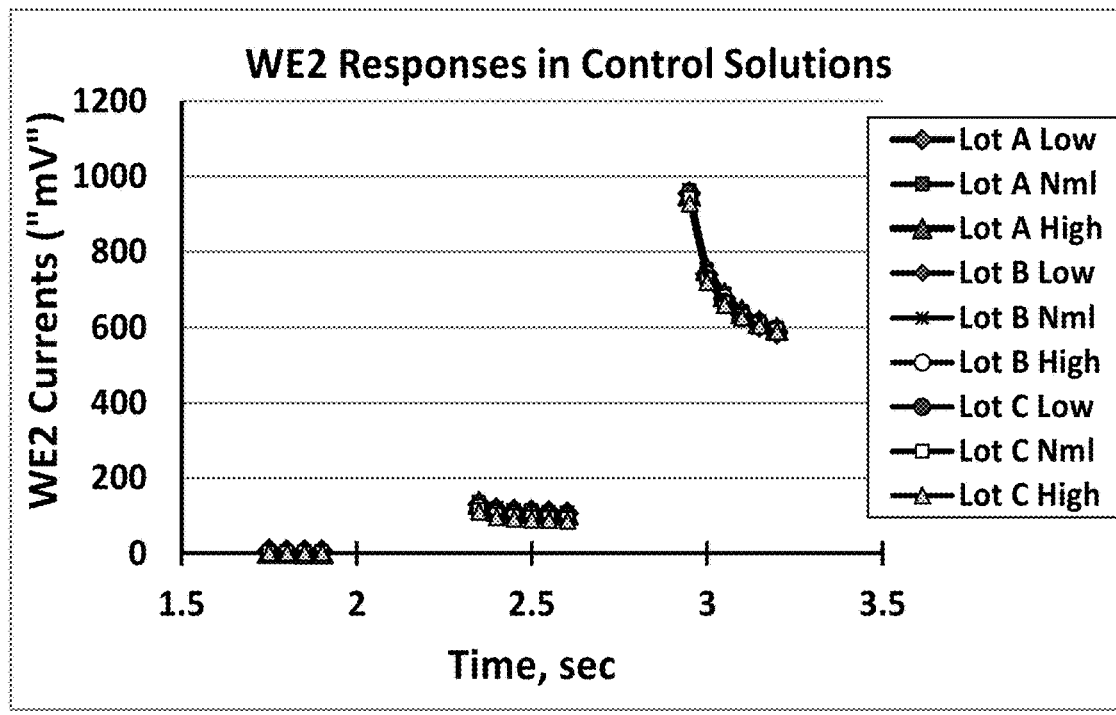
FIG. 14C is a graph illustrating the currents measured in response to the third and fourth pulses of the second input signal, in addition to the third Hct input signal, in FIG. 8D applied to various controls, in accord with aspects of the present disclosure.
Figure 14D:
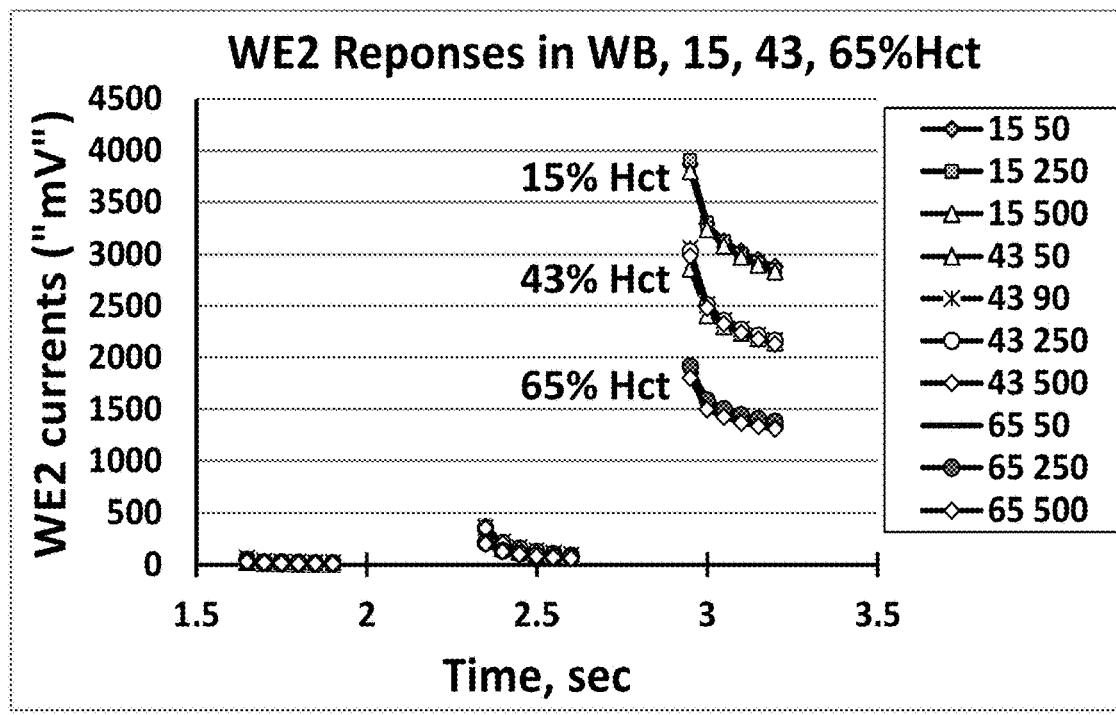
FIG. 14D is a graph illustrating the currents measured in response to the third and fourth pulses of the second input signal, in addition to the third Hct input signal, in FIG. 8D applied to various WB samples, in accord with aspects of the present disclosure.

As shown in FIG. 14A, the currents measured in response to the first pulse of the second input signal—specifically, 0.25 V applied across the bare electrode 118 and the counter electrode 116—are negative. In contrast, and as shown in FIG. 14B, the currents measured in response to the same pulse applied to the various WB samples are positive. Based on the resulting negative currents for the controls in response to the first pulse of 0.25 V of the second input signal and the resulting positive currents for the WB samples in response to the same pulse, a threshold near zero or the polarity switch of the measured currents can indicate whether the sample is a control or WB sample. FIG. 14C is a graph illustrating the current measurements in response to the third and fourth pulses of the second input signal, in addition to the third Hct input signal, in FIG. 8D applied to the controls of FIG. 14A, in accord with aspects of the present disclosure. FIG. 14D is a graph illustrating the current measurements in response to the third and fourth pulses of the second input signal, in addition to the third Hct input signal, in FIG. 8D applied to the various WB samples of FIG. 14B, in accord with aspects of the present disclosure.

At potentials lower than 0.2 V, the current $i_{G1,1}$ values from a WB sample will become negative as well. At 0.3 V, the $i_{G1,1}$ values for controls may edge up to positive. The pH of the controls from 6.5 to 7.0 will give the negative values at $i_{G1,1}$. At a much higher pH value (e.g., 7.5 and above), the $i_{G1,1}$ values of the control will become positive. The negative $i_{G1,1}$ currents may indicate that the controls are being poised slightly at a reduction potential of 0.25 V while the WB samples are poised at slightly oxidation potential of 0.25V. This behavior seemingly indicates a polarity switch from control to WB samples, but the behavior shows more of a threshold current near zero. This threshold of separating the sample types may shift depending on the operation conditions. Other threshold current values may be possible depending on other factors, such as the operation potential, the control pH, and the buffer concentration. For instance, the operation potential at 0.25 V is relative to the MLB mediator's redox potential at the counter electrode. If ferricyanide is the mediator, which has a redox potential about 150-200 mV higher than MLB, the operation potential needs to be at about 0.05-0.1 V to maintain the threshold near zero.

In addition or in the alternative to the polarity of the currents indicating whether the sample is a control or a biological sample, decay characteristics of the currents in response to one or more pulses of the second input signal, alone or in combination with the first input signal, can be used to distinguish a control from a biological sample.

Figure 15:
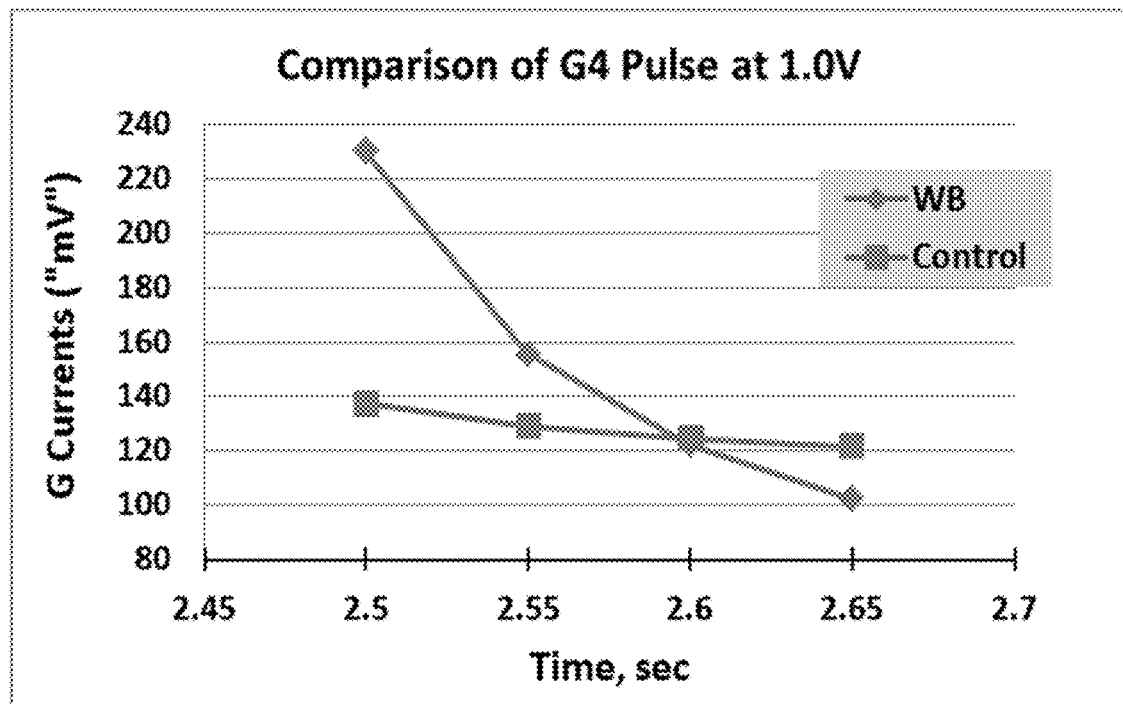
FIG. 15 is a graph illustrating an approximation of the decay of the currents of the second input signal as a function of time relative to the time during which the pulse of the second input signal was applied to the sample, in accord with aspects of the present disclosure.

FIG. 15 shows a comparison of the decay from the second input pulse at 1.0 V in a WB sample and in a control solution based on the bis-tris. It was observed that there is a steep decay in the WB sample and a shallow decay in the bis-tris buffer-based control solution. According to some aspects, the decay characteristics can be expressed by the parameter DG4 defined as follows in Equation 1.

$$DG4 = i_{G4\text{-}first}/i_{G4\text{-}ending} - 1 \tag{1}$$

Other similar parameters, such as RG4 ($=i_{G4,nth}/i_{G4,1st}$) can also be used to express the decay characteristics with similar comparison results between controls and WB samples.

Rather than relying on a user of the biosensor system to choose the single, correct control to be used with the biosensor system, the system 100 can distinguish between multiple different controls and operate accordingly. Under the scenario of a user mistakenly using a control that is not preferred for a specific biosensor system, the system can still determine that the control is not the preferred control and modify its functionality and/or operation appropriately based on the detected specific type of control. In some aspects, the biosensor system can provide a control reading based on other calibration constants if the biosensor system is equipped with the other constants. Alternatively, the biosensor system can indicate that the control being used is not the preferred control and provide an indication to the user to use the preferred control.

According to the foregoing, differentiation among three or more sample types, such as between two or more predetermined types of controls, is possible. Unlike conventional methods that rely on the direct oxidation of an added control marker at a high voltage to generate a current for calculating a differentiating index, currents measured from pulses of the second input signal at potentials equal or close to the operation potentials of the working electrode in controls with or without an added control marker can be used. Below are additional examples of how information from the second output signal, alone or in combination from information from the first input signal, can be used to different between different controls.

The pulsing sequence shown in FIG. 8D was applied to controls based on five different buffer systems for testing the controls' responses to the second electrode input pulse at 0.25 V. The five buffer systems were 100 mM of phosphate ion at a pH of 6.5, 20 mM of Trizma® acetate at a pH of 7, 20 mM of ADA at a pH of 7, 20 mM of HEPES at a pH of 6.7, and bis-tris at a pH of 6.5. The results are shown in FIG. 16A in a plot of $i_{G1,1}$ versus DG4.

Figure 16A:
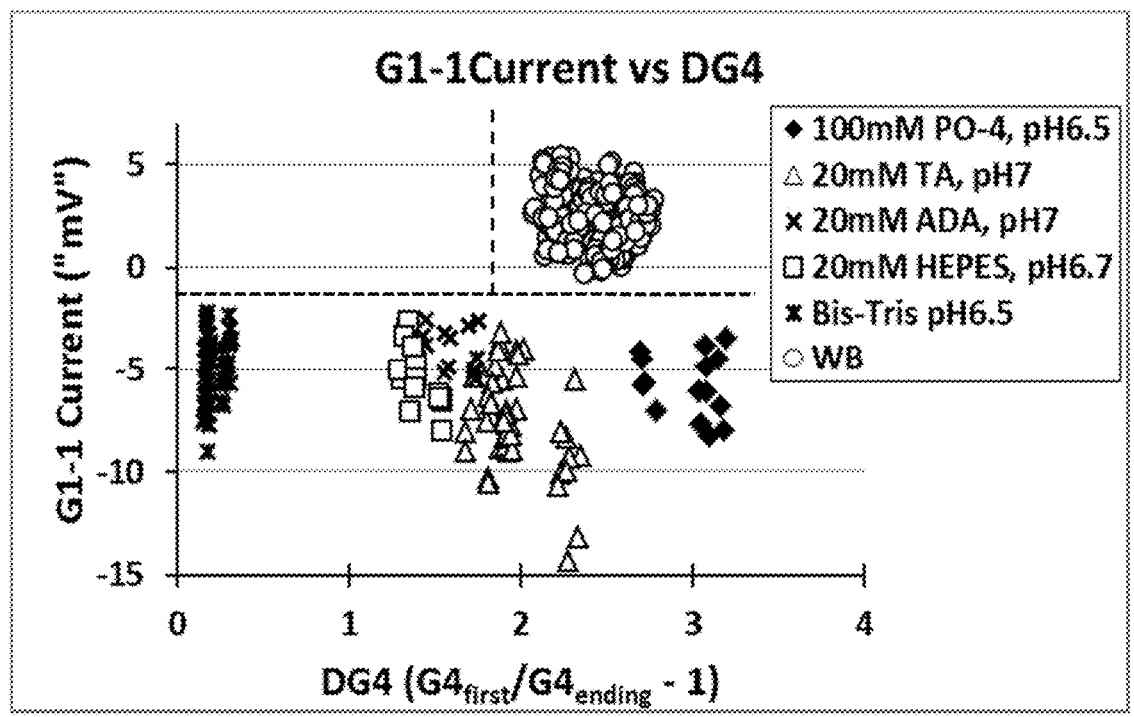
FIG. 16A is a graph illustrating currents $i_{G1,1}$ versus the parameter DG4 for WB samples and controls based on the first and second input signals from FIG. 8D, in accord with aspects of the present disclosure.

Specifically, FIG. 16A is a graph of current measurements $i_{G1,1}$ versus the parameter DG4 for the WB samples and controls based on the input signals of FIG. 8D, in accord with aspects of the present disclosure. As shown, for 270 WB samples, 98.9% of the resulting currents $i_{G1,1}$ were positive or at 0 while all of the currents $i_{G1,1}$ for the five controls were more negative than any of the values from the WB samples. The WB sample chemistry is complex but gave the dominantly positive $i_{G1,1}$ currents. In contrast, the controls were consistent with respect to their formulations and gave consistently negative $i_{G1,1}$ currents. Thus, the five buffer systems gave slightly negative currents at 0.25 V versus the sensor mediator redox potential at the counter electrode. While the DG4 values for the five buffer systems varied from 0.2 to 3.5, the $i_{G1,1}$ currents were all negative. Thus, the characteristic behavior of WB's slightly oxidative currents and control's slightly reductive currents formed a boundary to differentiate the WB samples from the aqueous solutions, where more than one aqueous solution behaved opposite to the WB. Accordingly, a comparison of the currents of $i_{G1,1}$ versus the parameter DG4, or the currents of $i_{G1,1}$ by themselves, can be used to distinguish between WB samples and controls. A threshold value can be set at slightly negative to separate the control solutions from the WB samples.

The fact that the boundary happens to be at approximately zero reflects a slight oxidative moiety for the WB samples and a slight reductive moiety for the controls under the conditions of the biosensor system construction and formulation (e.g., specific reagents for the working electrode 114), as well as the operation potential at 0.25 V between the bare electrode and the counter electrode. This characteristic difference in principle represents a polarity switch of the current $i_{G1,1}$ with respect to a threshold near zero and provides the differentiation between WB samples and controls based on the first current of the second output signal in response to the 0.25 V pulse of the second input signal. At 0.2 V or below, the WB sample currents $i_{G1,1}$ were shifted to negative. At 0.3 V, the controls' currents $i_{G1,1}$ were shifted to positive. For biosensor systems having different reagents, such as different mediators, such as ferricyanide, the dividing boundary or the polarity switch may occur at other operation potentials between the bare electrode and the counter electrode because of the potential shift of the other mediator.

Figure 16B:
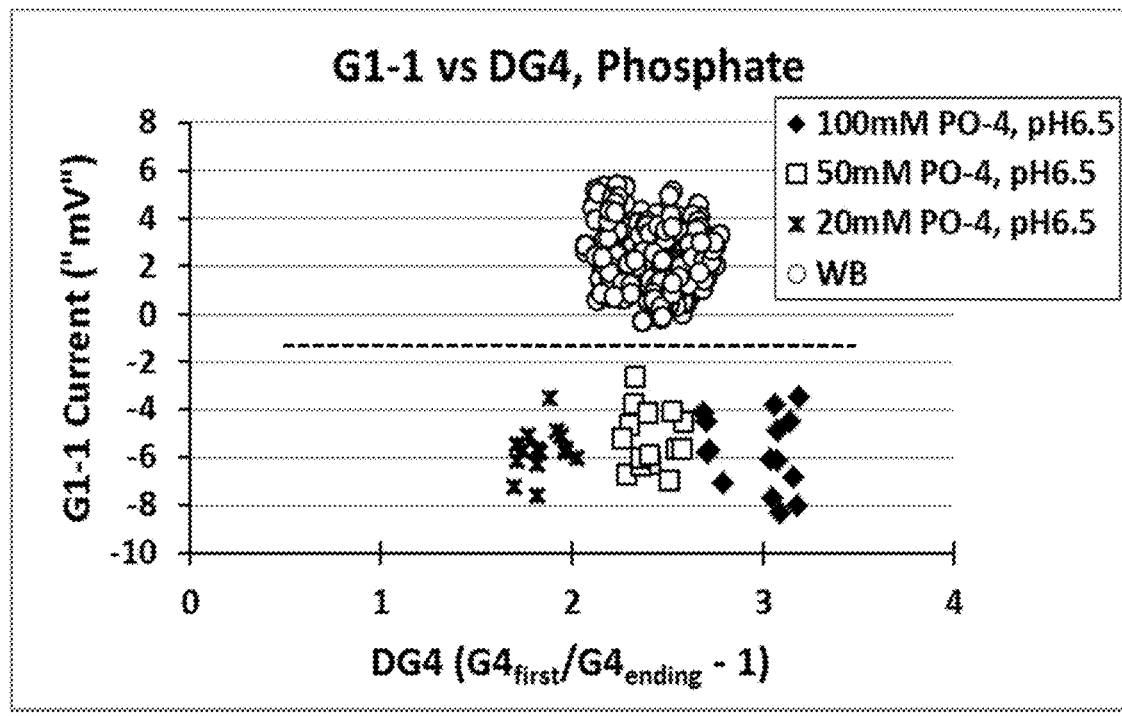
FIG. 16B is a graph illustrating currents $i_{G1,1}$ versus the parameter DG4 for the WB samples and controls based on the input signals of FIG. 8D, in accord with aspects of the present disclosure.

FIG. 16B further showed the $i_{G1,1}$ currents from the phosphate-based control solutions with three different buffer concentrations of 20, 50 and 100 mM at a pH of 6.5. While the DG4 values varied with the buffer concentrations, the $i_{G1,1}$ currents were all below the threshold dotted line, which separates the control solution values from those of the WB currents.

Figure 16C:
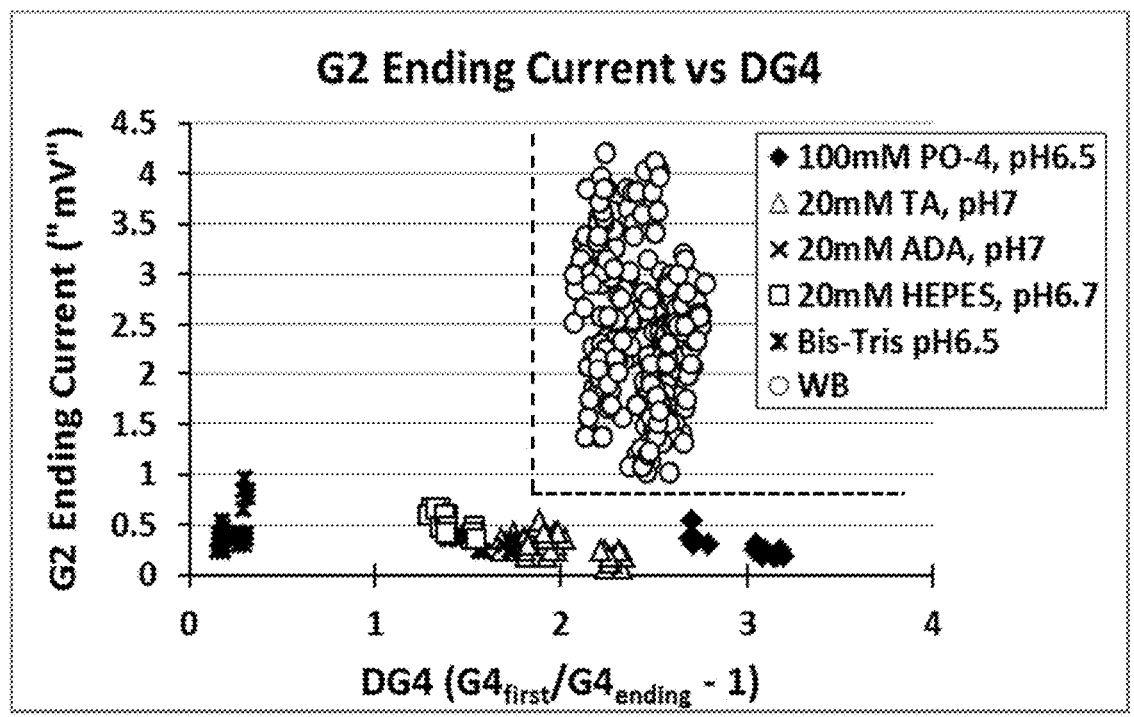
FIG. 16C is a graph illustrating currents $i_{G1,1}$ versus the parameter DG4 for three phosphate ion controls at the buffer concentrations of 20, 50, and 100 mM, in accord with aspects of the present disclosure.

In addition to the $i_{G1,1}$ currents as one of the indicators, the ending current of bare electrode pulse can also be used to differentiate controls from WB samples. This is shown in the plot of $i_{G2,nth}$ versus DG4 in FIG. 16C, where the WB samples data points are clustered in the upper right region of the plot. That is, the data points for the WB samples are clustered in the region greater than or equal to 1 ("mV") and greater than 2 of the parameter DG4. For the bis-tris control, the WB samples and the controls can be well differentiated based on the indicator of DG4, and to a lesser extent for the HEPES control system. This may be readily implemented in a system by thresholds based on the vertical boundary and the horizontal boundary.

Figure 16D:
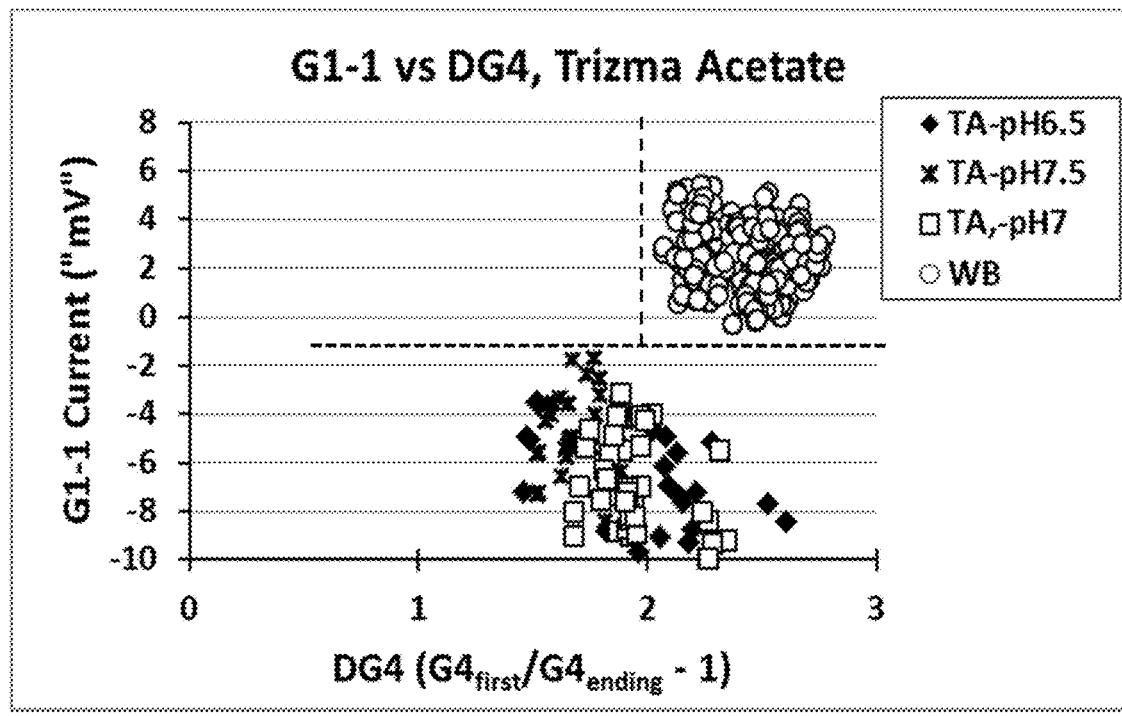
FIG. 16D is a graph illustrating currents $i_{G1,1}$ versus the parameter DG4 for a Trizma® acetate control, made by Sigma Chemical Company of St. Louis Mo., at pHs of 6.5, 7, and 7.5 for each of the three buffer concentrations of 20, 50 and 100 mM, in accord with aspects of the present disclosure.

FIG. 16D is a graph showing currents $i_{G1,1}$ versus the parameter DG4 for the Trizma® acetate buffer based control at combinations of three pHs of 6.5, 7, and 7.5 and three buffer concentrations of 20, 50 and 100 mM, in accord with aspects of the present disclosure. Specifically, FIG. 16D shows the combined effect of buffer concentration and the pH on the currents $i_{G1,1}$ for the Trizma® acetate control. There is a trend of low pH giving more negative currents $i_{G1,1}$, thus enhancing the negative polarity. The combination of the current $i_{G1,1}$ and the parameter DG4 also applies to the ADA buffer system for differentiating WB samples and controls.

Figure 16E:
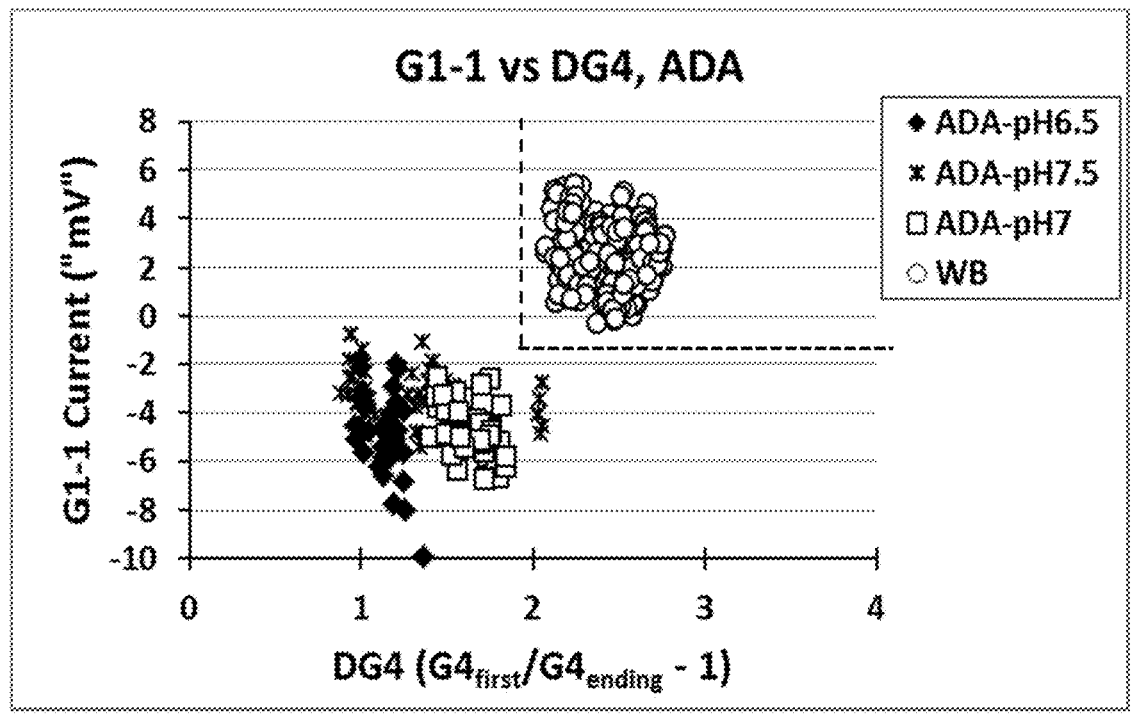
FIG. 16E is a graph illustrating currents $i_{G1,1}$ versus the parameter DG4 for an N-(2-acetamido)iminodiacetic acid (ADA) control at pHs of 6.5, 7, and 7.5 for each of the three buffer concentrations of 20, 50, and 100 mM, in accord with aspects of the present disclosure.

FIG. 16E is a graph showing currents $i_{G1,1}$ versus the parameter DG4 for the ADA control at combinations of three pHs of 6.5, 7, and 7.5 and three buffer concentrations of 20, 50, and 100 mM, in accord with aspects of the present disclosure. The combination of $i_{G1,1}$ and DG4 also applies to the ADA control for differentiating WB samples and controls.

Figure 16F:
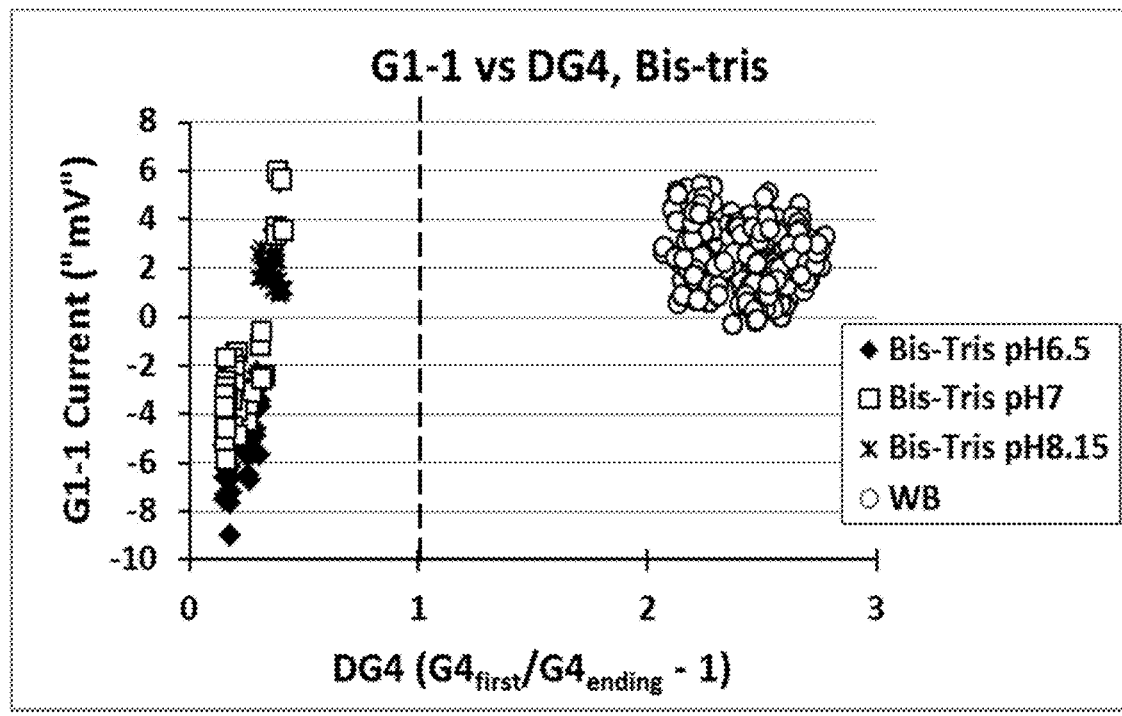
FIG. 16F is a graph illustrating currents $i_{G1,1}$ versus the parameter DG4 for bis-tris controls at combinations of three pHs of 6.5, 7, and 7.5 for each of the three buffer concentrations 20, 50, and 100 mM, in accord with aspects of the present disclosure.

FIG. 16F is a graph showing currents $i_{G1,1}$ versus the parameter DG4 for the bis-tris controls at combinations of three pHs of 6.5, 7, and 7.5, and three buffer concentrations 20, 50, and 100 mM, in accord with aspects of the present disclosure. The $i_{G1,1}$ currents tended to cross the boundary with higher pH values of the control solution, but there was a wide margin in the DG4 axis for differentiating the controls against the WB samples. In FIG. 16F, the pH of the bis-tris control affected the current $i_{G1,1}$ polarity significantly that at or slightly above a pH of 7, some of the currents $i_{G1,1}$ went above 0. At a pH of 8.15, all of the currents $i_{G1,1}$ were positive. However, the differentiation between a WB sample and a bis-tris control is predominantly determined by the parameter DG4, as shown by the wide margin in FIG. 16F. This trend is independent of the bis-tris concentrations (e.g., 20, 50, and 100 mM bis-tris).

Different parameters can be better suited for controls based on different buffers. Other parameters that can be calculated from the second output signal include $RG_{31}$, $RG_{32}$, $RG_{41}$, $RG_{42}$, and $RG_{43}$, as defined above. A selection of the optimal control formulation (e.g., pH and/or buffer concentration) and operation potential at the second input signal pulses can enhance a particular parameter for one control system. According to some aspects, there can be more than one indicator for differentiating WB samples and controls.

The dashed and/or dotted lines in FIGS. 16A-16F can represent thresholds programmed into a biosensor system that can be used in comparisons to currents and/or parameters based on the current for distinguishing the sample between a control and a non-control, and/or distinguishing between different controls.

After the sample type has been determined to be a control, it can be differentiated further as one particular type of control from another. The input signals of FIG. 8B were applied to various samples, including lab WB samples and donor WB samples, in addition to two controls. The lab WB samples included 3000 different samples that covered glucose concentrations of 60, 330, and 550 mg/dL at 5, 10, 15, 23, 33, 40, and 45° C., and 0, 20, 42, 55, and 70% Hct values. The donor WB samples included 3652 different samples covering a range of glucose concentrations and Hct values. The first control included a solution from the CONTOUR® CLASSIC glucose meter by Ascensia Diabetes Care of Parsippany, N.J., and the second control included a solution from the CONTOUR® NEXT glucose meter by Ascensia Diabetes Care of Parsippany, N.J.

Figure 17A:
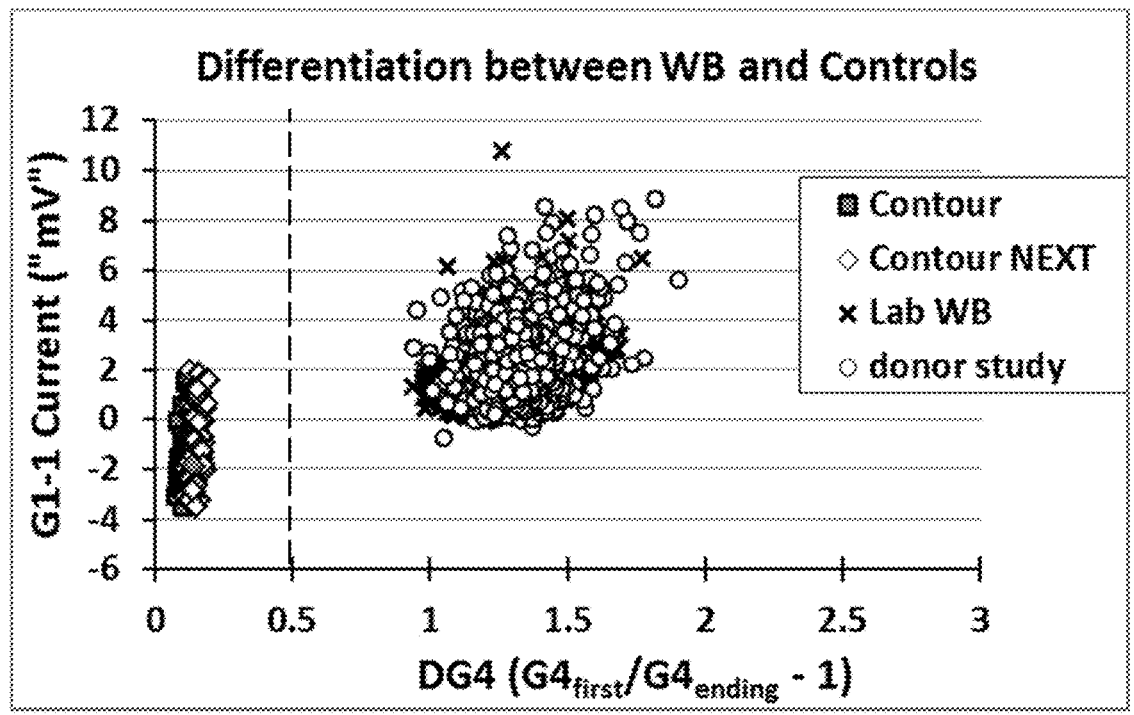
FIG. 17A is a graph illustrating currents $i_{G1,1}$ versus the parameter DG4 for the WB samples and controls based on the input signals of FIG. 8B, in accord with aspects of the present disclosure.

FIG. 17A shows a plot of $i_{G1,1}$ versus DG4 ($i_{G4\text{-}first}/i_{G4\text{-}ending}-1$) for the CONTOUR® CLASSIC and CONTOUR® NEXT control solutions by Ascensia Diabetes Care of Parsippany, N.J., along with the WB sample data from lab studies (across temperatures, glucose concentrations, and hematocrit levels) and from donor studies. The DG4 indicator provided a wide margin to separate the control data points from the WB data points. As shown, for the lab WB samples, 100% of the currents $i_{G1,1}$ were positive or at 0. For the donor WB samples, 99.86% of the currents $i_{G1,1}$ were positive or at 0. Thus, the WB samples gave positive currents $i_{G1,1}$ in response to the 0.25 V. In contrast, more than 85% of the currents $i_{G1,1}$ currents were negative for the controls.

In FIG. 17A, the predominant parameter for separating the WB samples and the controls was the parameter DG4. There was a wide margin in the parameter DG4 axis between the data for the controls and the WB samples. Optionally, the $RHG_4$ parameter ($i_{H\text{-}ending}/i_{G4\text{-}ending}$) can also be used.

Figure 17B:
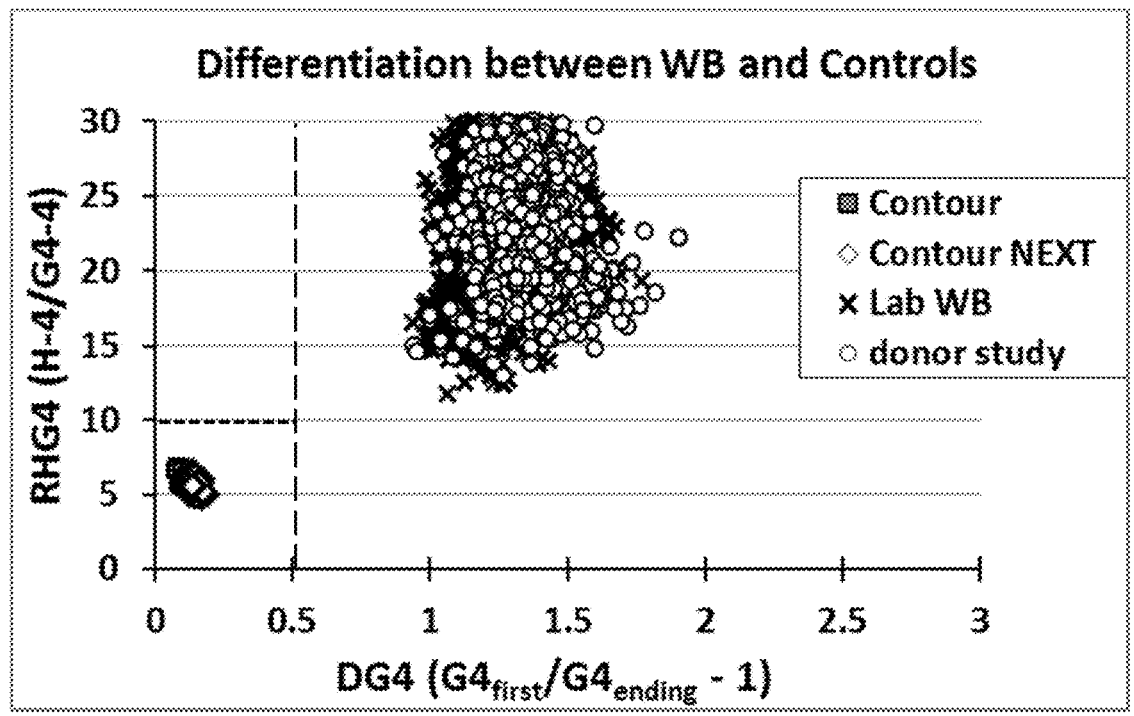
FIG. 17B is a graph illustrating a differentiation between WB samples and controls based on the parameters $RHG_4$ and DG4, in accord with aspects of the present disclosure.

Better separation can be provided in another two-way plot of $RHG_4$ versus DG4, as shown in FIG. 17B. The control data points are shown in the lower left corner of the plot clearly separated by two boundaries. For the parameter RHG4, there was an inverse correlation between RHG4 and % Hct of the WB sample. Thus, the separation margin was between the highest hematocrit level at 70% and the controls.

After distinguishing between WB samples and controls based on the parameters RHG4 and DG4, an additional comparison can occur based on the same parameters or one or more additional parameters. The additional comparison can distinguish between multiple different controls.

Figure 17C:
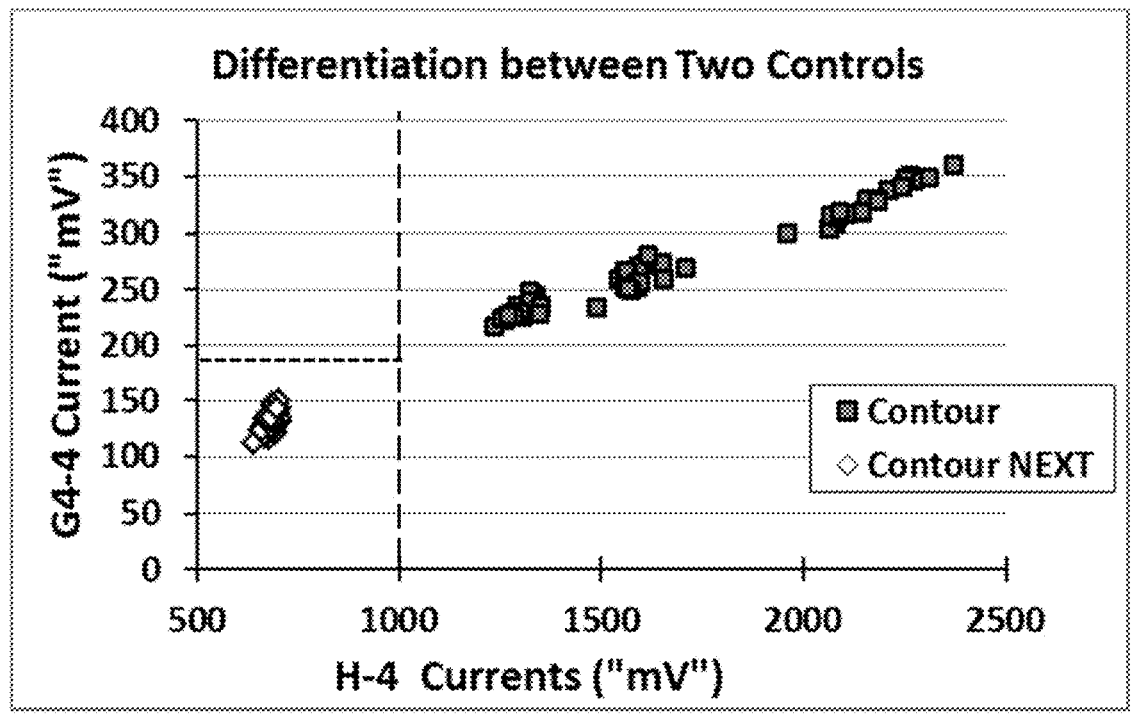
FIG. 17C is a graph illustrating the differentiation between two controls based on two currents $i_{G4,4}$ and $i_{H,4}$, in accord with aspects of the present disclosure.

For example, once the sample type has been determined to be the control, the control can be further separated from multiple different controls, as shown in FIG. 17C applied to the two exemplary controls CONTOUR® CLASSIC and CONTOUR® NEXT. The two-way plot of $i_{G4,4}$ versus $i_{H,4}$ currents (the ending current of the 1.0 V $G_4$ pulse against the ending current of the 2.5 V hematocrit pulse) results in the CONTOUR® NEXT controls at the low left corner. The comparison shown in FIG. 17C can occur in response or subsequent to the comparison shown in FIG. 17B. For example, after determining that the sample is a control based on the comparison in FIG. 17B, a biosensor system can perform the comparison shown in FIG. 17C to determine the specific type of control.

The dashed and/or dotted lines in FIGS. 17A-17C can represent thresholds programmed into a biosensor system that are used in comparisons to currents and/or parameters based on the currents for distinguishing the sample between a control and a non-control, and/or distinguishing between different controls.

Based on the parameters discussed above, a biosensor system can determine the parameters for distinguishing a sample between, for example, a control and a WB sample, and also between multiple different specific controls. Based on distinguishing the sample as a control or a WB sample, or as a specific control among a plurality of different specific controls, a biosensor system can then alter its functionality and/or operation based on the determined sample type.

Figure 18:
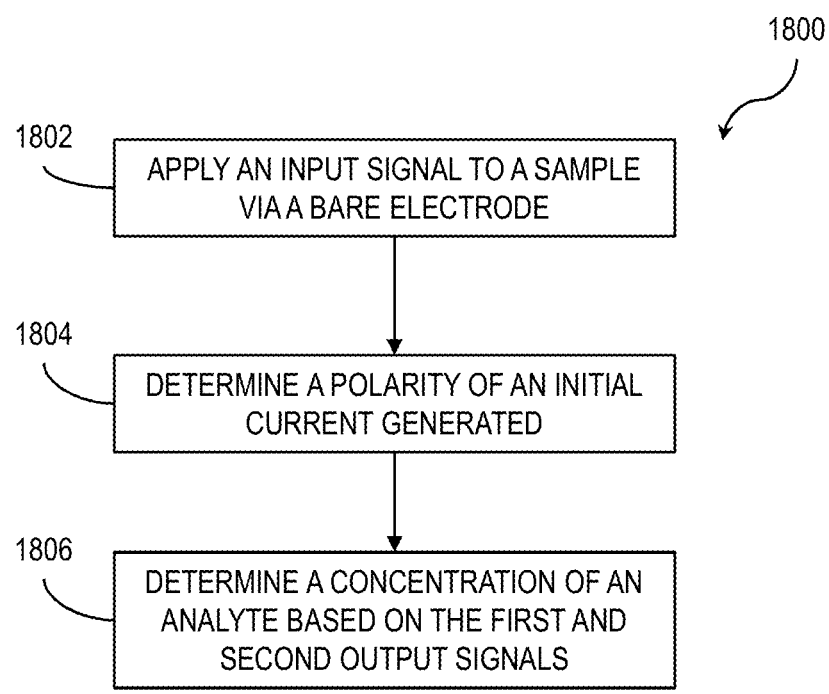
FIG. 18 is a flowchart of a process for analyzing a solution with a blood glucose monitoring device, in accord with aspects of the present disclosure.

FIG. 18 is a flowchart of a process 1800 for analyzing a solution with a blood glucose monitoring device, in accord with aspects of the present disclosure. The process 1800 can be performed by a biosensor system, such as the biosensor system 100 discussed above. Specifically, the biosensor system performing the process 1800 can be a device for determining the concentration of glucose in a blood sample, such as a WB sample.

At step 1802, an input signal is applied to the solution via a bare electrode of the blood glucose monitoring device. The bare electrode is any bare electrode as described herein, such as the bare electrode 118 of the biosensor system 100. The input signal includes at least one constant voltage pulse. In some aspects, the constant voltage pulse is a potential of 0.25 V. The sample can be a blood sample, such as a WB sample.

Although the input signal can include one constant voltage pulse, in some aspects, the input signal can further include a plurality of voltage pulses. The plurality of voltage pulses can be applied across the bare electrode and a counter electrode. Among the plurality of voltage pulses is the constant voltage pulse described above in the preceding paragraph.

At step 1804, a comparison is made between a current related to the output current generated in response to the 0.25 V voltage. The output current that is measured is the current responsive to the applied constant voltage pulse in step 1802.

In some aspects, a polarity of an output current generated in response to the 0.25 V voltage pulse is determined. The polarity of the output current is determined by measuring an output current in the sample that is generated based on the applied constant voltage pulse in step 1802. The polarity of the output current is then determined, such as being a positive or a negative current. In this aspect, the threshold can relate to the polarity, i.e., whether the polarity is positive or negative. In some aspects, the polarity is of the initial current that is measured in response to the constant voltage pulse. Thus, if a plurality of currents is measured in response to the constant voltage pulse, the polarity of the first or initial current is determined at step 1804. The constant voltage pulse is at 0.25 V.

At step 1806, the solution is identified as a control or a blood sample based, at least in part, on the comparison to the threshold. For example, if below the threshold, the solution is identified as a control. If above the threshold, the solution is identified as a WB sample. However, the relationship can be the opposite, such as below representing the WB sample. In the case of the threshold relating to polarity, if the polarity is negative, the solution is identified as a control. If the polarity is positive, the solution is identified as a blood sample, such as a WB sample.

In response to the determination of the sample as being a control or a WB sample, the biosensor system can perform additional functionality and/or operations automatically, such as without additional user input to the biosensor system that would otherwise be required to initiate the additional functionality and/or operations. Such additional functionality and/or operations can include, for example, performing and/or running one or more operations that determine whether the biosensor system is functioning correctly in response to determining that the sample is a control. Such operations can include, for example, determining a concentration of a species in the control and comparing the concentration to a pre-set, standard concentration for the control to determine whether the biosensor system is operating within set tolerances. Such additional functionality and/or operations can include, for example, performing and/or running one or more operations that determine the concentration of an analyte in the sample, such as glucose, in response to determining that the sample is a WB sample. Accordingly, the ability of a biosensor system to determine the sample as being a control or a WB sample allows for the automatic initiation of additional functionality and/or operations without user intervention, which can simplify use of the biosensor system and/or reduce potential for errors, such as human error in using the biosensor system.

For aspects in which the input signal includes a plurality of voltage pulses, the solution can be identified as a predetermined control among a plurality of predetermined controls based, at least in part, on the plurality of voltage pulses, in response to or after identifying the solution as the control.

The solution can be identified as one predetermined control among the plurality of predetermined controls based, at least in part, on an initial voltage pulse and a final voltage pulse of the input signal, or between two intermediary pulses, depending on the potentials of the pulses and the sample. One or the first of the voltage pulses can be a potential of 0.25 V applied across the bare electrode and the counter electrode, and another one or the final voltage pulse can be a potential of 1.0 V applied across the bare electrode and the counter electrode.

In some aspects, a first plurality of currents is measured in response to the initial or one voltage pulse and a second plurality of currents is measured in response to the final or another voltage pulse. The solution is then identified as the predetermined control based on an initial current of the first plurality of currents and a final current of the second plurality of currents. Alternatively, the identification of the solution as the control or the blood sample can be based, at least in part, on an initial current of the first plurality of currents in response to the initial voltage pulse, an initial current of the second plurality of currents in response to the final voltage pulse, and a final current of the second plurality of currents in response to the final voltage pulse. In some aspects, the identification of the solution as the control or the blood sample is based, at least in part, on a ratio of (i) the initial current of the second plurality of currents in response to the final voltage pulse and (ii) the final current of the second plurality of currents in response to the final voltage pulse, compared to the initial current of the first plurality of currents in response to the initial voltage pulse.

Figure 19:
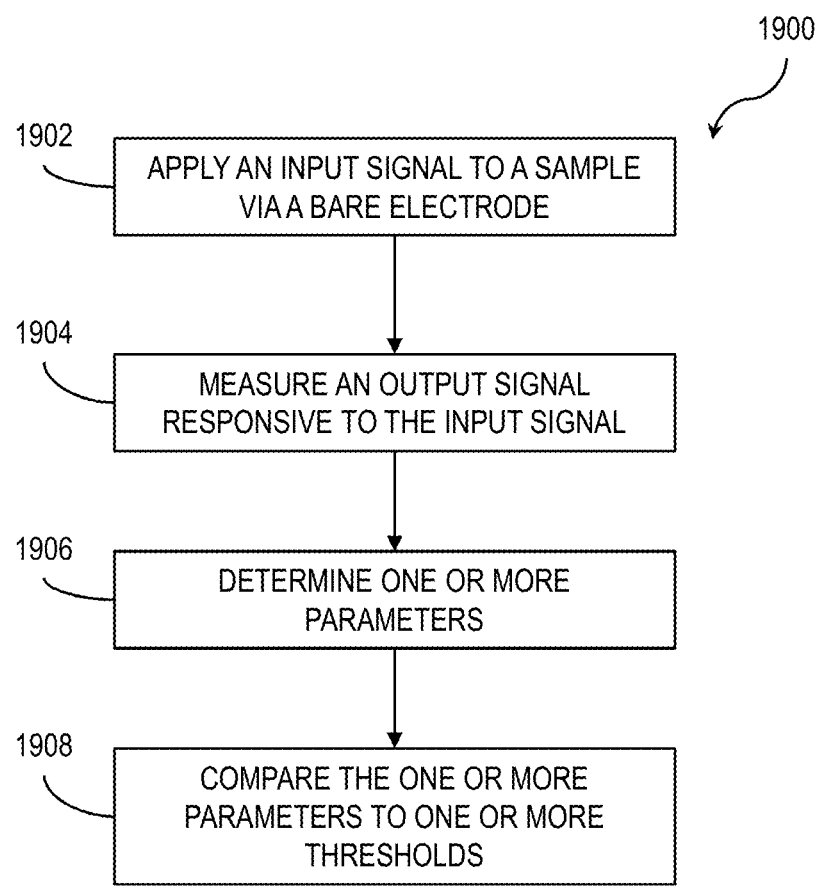
FIG. 19 is a flowchart of a process for determining a type of a sample, in accord with aspects of the present disclosure.

FIG. 19 is a flowchart of a process 1900 for determining a type of a sample, in accord with aspects of the present disclosure. The process 1900 can be performed by a biosensor system, such as the biosensor system 100 discussed above. Specifically, the biosensor system performing the process 1900 can be a device for determining the concentration of glucose in a blood sample, such as a WB sample.

At step 1902, an input signal is applied to the sample via a bare electrode. The bare electrode is configured as described above with respect to the bare electrode 118. The input signal can be applied between the bare electrode and a counter electrode. The counter electrode is configured as described above with respect to the counter electrode 116. The input signal has at least two excitations and a relaxation.

Although described as one input signal being applied to the sample, in some aspects, another input signal can be applied to the sample intertwined with the input signal. The intertwining is as described above. Specifically, the intertwining can include applying to the sample the other input signal via a first electrode having a reagent, the other input signal having at least two excitations and a relaxation, and the at least two excitations of the other input signal being nonconcurrent with the at least two excitations of the input signal.

At step 1904, an output signal is measured that is responsive to the input signal of step 1902. The output signal can be measured as described above, such as by the measurement device 102. Similar to the output signals discussed above, the output signal includes currents measured in response to the at least two excitations of the input signal. In some aspects, the currents include at least two currents. The at least two currents can be responsive to one of the at least two pulses or excitations of the input signal. Alternatively, each one of the at least two currents can be responsive to a separate pulse or excitation of the at least two pulses or excitations of the input signal. In the case of more than two excitations or pulses and/or or more than two currents, there can be a combination of multiple currents measured in response to the same excitations and multiple currents measured in response to separate excitations.

At step 1906, one or more parameters are determined based on the output signal. The one or more parameters can be determined based on the current measurements. The one or more parameters can be determined based on intra-pulse ratios, inter-pulse ratios, or combinations thereof. Alternatively, the one or more parameters can be the currents, or combinations of currents and ratios. The one or more parameters are selected based on the parameters being able to distinguish between the type of the sample and, in some aspects, between sub-types or predetermined types of the same sample.

At step 1908, the one or more parameters are compared to one or more thresholds to determine the type of the sample. In some aspects, the type of sample is determined from among two types. The two types can be a control and a biological sample. The control can be for determining whether the biosensor system performing the process 1900 is functioning properly, or for calibrating the biosensor system, or both. The biological sample can be various biological samples, such as biological fluids including one or more of WB, serum, plasma, urine, saliva, an interstitial fluid, or an intracellular fluid.

In some aspects, one of the two types can include multiple sub-types. For example, the control can have various sub-types that include predetermined controls or specific types of controls. In response to a determination that the sample is a control, an additional step of comparing the one or more parameters to one or more additional thresholds can occur to determine the sub-type of the control, or specifically the predetermined control.

In some aspects, after determining the type of the sample, and specifically the predetermined control, the process 1900 can include causing, at least in part, an indication of the predetermined control. Such an indication can include displaying the specific control type on a display of the biosensor system.

Alternatively, or in addition, after determining the type of the sample, and specifically the predetermined control, the operation of the biosensor system performing the process 1900 can be modified based on the determined predetermined control. For example, if different equations or sets of equations are used to determine whether the operation and/or calibration of the biosensor system is correct, the specific equations that are used can be dependent upon the specific predetermined control that is used for the verification of the operation and/or calibration. Upon determining the predetermined control that is being analyzed by the biosensor system, the biosensor system can select the appropriate equations to use according to the determined predetermined control. Accordingly, a user of a biosensor system that is configured to perform the process 1900 can use one of a multitude of different controls with the biosensor system. The biosensor system, in response to performing the process 1900, can identify the specific control that is being used and modify its functionality and/or operation appropriately. Thus, a user is not relied upon to select the correct control for the biosensor system. In contrast, the biosensor system, through the process 1900, can accommodate multiple different controls, which can simplify use of the biosensor system and/or reduce potential errors.

In addition, or in the alternative, to distinguishing between a control and a biological sample, or between multiple different controls, analysis of the second output signal, alone or in combination with analysis of the first output signal, can allow for other functionality and/or operation within a biosensor system. Such additional analysis and the related functionality and/or operation can provide management of interference effects from one or more interference species within the biological sample.

Interference is a common subject in analyte determinations in samples by biosensor systems, especially biosensor systems used in biological samples, such as WB. Modes of interference can include (a) species oxidized at the working electrode simultaneously with the target analyte without the enzyme activated reaction and (b) species oxidized by the enzyme due to the non-specificity toward the interferent substrate. Oxidizable interference species include ASA and Dop, and to a lesser extent UA and AA. Enzyme sensitive interference species can include xylose with FAD-GDH enzyme. Modes of interference can also include species that affect the signal used to indicate hematocrit. Less obvious modes of interference can also include species that affect the electrode activity in a subtle, negative way.

Interference species can be divided into internal and external species, with internal species being those present naturally in the biological system or the human body, such as Dop and UA, and external species being those taken in by the individuals, such as ASA, AA, and xylose. In biosensor systems where only the working electrode having reagent chemistry for the target analyte is excited by applying a potential, the presence of the interference species is not detected at the working electrode. Moreover, in biosensor systems where an auxiliary electrode provides a single fixed potential, the presence of the interference species also is not detected at the auxiliary electrode.

The goal of interference management is to remove/minimize the effects from the interference species. Indeed, interference species can be encountered during the analysis of an analyte in a biological sample by a biosensor system. In such a situation, effects of the interference species can be measured as part of an output signal of the biosensor system used to determine the analyte concentration. Such interference by the interference species can go undetected, affecting the determined concentration of the analyte. Conventional approaches attempt to alleviate the effects of interference species with the introduction of new reagents on the working electrode. The new reagents, such as new mediators, can lower the operation potential for the biosensor systems, which in turn lowers the effects of most interference species in the biological samples.

Interference management provides for the biosensor system to detect interference signals and/or signals that are used to compute parameters for detecting/recognizing the interference effects. Specifically, the method of interference management involves sorting one or more signals, and/or one or more parameters related to interference effects, such that interference data and normal data are separated by defined boundaries with thresholds. More specifically, the disclosed method involves applying intertwined input signals to the biosensor systems and measuring signals responsive to the input signals. The resulting output data can be sorted and one or more signals, and/or one or more parameters, are organized/formulated to define the boundaries between normal data and interference data. When the normal data and the interference data are separated, appropriate actions can be taken to manage the outcome for the individual cases. For instance, if an individual data point is identified in the normal data region, as defined by the separation map with threshold values, normal calculation/compensation for analyte concentration can be carried out. If, however, the individual data point is identified in the region of likely overlap between no/low interference and moderate interference, special calculation/compensation for the analyte concentration can be carried out. Finally, if the individual data point is identified in the region of high interference, this data point can be rejected because of the detected high interference signals/parameters based on the separation map.

In the case of biosensor systems measuring glucose concentrations, interference species in biological samples can interfere with glucose concentration measurements in different ways. There can be interference species that are directly oxidizable at the working electrode. Such interferences species include, for example, ASA and Dop (or catechol amines). There can be interference species that are sensitive to the reagents and generate additional electrons, regardless of whether these species are oxidizable. Such interference species include, for example, xylose with respect to the enzyme FAD-GDH for glucose. This interference species can contribute to high bias. Eliminating or reducing the effects of xylose from the FAD-GDH enzyme would require a xylose insensitive enzyme, which can be cost-probative by not being backwards compatible with the existing biosensor systems, including the algorithms of the existing biosensor systems, and/or not chemically possible for all interference species.

Other interference species may not necessarily contribute positively to the working electrode output signal but may still affect the electrochemical reaction at the electrode surface, such as AA and UA for the working electrode. Other interference species may affect the output signals of the hematocrit pulse that represent the sample hematocrit level, such as cholesterol, and free hemoglobin in the WB sample which can lead to erroneous determinations of glucose concentrations through compensation with the erroneous hematocrit signals.

Because the effects of the interference signals are combined with the effects of the analyte and/or reagents at the working electrode, there is no way of eliminating or reducing the effects from the output signal of the working electrode. However, for intertwined gated input signals with a bare electrode pulsing at different potentials, intertwined with pulses from the working electrode, the resulting measured currents can be used to identify the effects of the interference species for compensation purposes. Moreover, such detection of such interference species is possible without having to rely on an interference species insensitive enzyme, such as a xylose insensitive enzyme, and likely reduces the cost of developing a new sensor.

With the bare electrode being poised at different potentials with different pulses, the resulting second output signal includes signals related to different behaviors of different interference species within the sample. The second output signal, or one or more parameters generated from the second output signal, can be analyzed alone and/or in combination with the first output signal, or one or more parameters from the first output signal, for detecting the presence of the interference species based on the different behaviors.

For example, starting at a potential equal to the operation potential of the first input signal applied by the working electrode (e.g., working electrode 114), pulses applied as the second input signal across a bare electrode (e.g., bare electrode 118) and a counter electrode (e.g., counter electrode 116) first detect any species that would also be detected in response to the first input signal of the same operation potential. The second input signal pulses then go onto progressively higher potentials to probe the near and far potential fields for other interference species that may not show any detectable signals at the operation potentials of the first input signal, but still have other positive and/or negative effects on the first output signal in response to the first input signal.

In the case of a mediator having a relatively low redox potential as one method to reduce the oxidizable interference effects, an example of this strategy is the use of the MLB mediator, where the redox potential is about 200 mV lower than that of the conventional ferricyanide mediator. As a result of using MLB as the mediator, the positive erroneous effects on the output signals from the working electrode by AA and UA are mostly avoided. Tables 3-7 below show the typical effects on the output signals from some of the interference species in the WB samples.

TABLE 3

Effects of Added Dop and ASA on Output Currents

| Glucose (mg/dL) | Added Dop (mg/dL) | Currents (mV) | %-bias to blank | Glucose, (mg/dL) | Added ASA (mg/dL) | Currents (mV) | %-bias to blank |
|---|---|---|---|---|---|---|---|
| ~80 | 0 | 66.47 | 0.00 | ~80 | 0 | 64.54 | 0.00 |
|  | 4 | 74.25 | 11.72 |  | 4 | 70.38 | 9.05 |
|  | 7 | 78.96 | 18.80 |  | 5 | 71.86 | 11.34 |
|  | 13 | 94.52 | 42.21 |  | 8 | 76.33 | 18.27 |
|  |  |  |  |  | 12 | 82.44 | 27.73 |
| ~300 | 0 | 261.38 | 0.00 | ~300 | 0 | 268.41 | 0.00 |
|  | 4 | 265.12 | 1.43 |  | 4 | 275.01 | 2.46 |
|  | 7 | 263.85 | 0.95 |  | 5 | 279.44 | 4.11 |
|  | 13 | 268.96 | 2.90 |  | 8 | 281.43 | 4.85 |
|  |  |  |  |  | 12 | 288.07 | 7.32 |

TABLE 4

Effects of Added AA and UA on Output Currents

| Glucose (mg/dL) | Added AA (mg/dL) | Currents (mV) | %-bias to blank | Glucose (mg/dL) | Added UA (mg/dL) | Currents (mV) | %-bias to blank |
|---|---|---|---|---|---|---|---|
| ~80 | 0 | 64.46 | 0.00 | ~80 | 0 | 71.78 | 0.00 |
|  | 10 | 63.68 | −1.20 |  | 10 | 68.61 | −4.42 |
|  | 20 | 62.08 | −3.69 |  | 25 | 64.02 | −10.82 |
|  | 32 | 62.55 | −2.95 |  | 40 | 61.60 | −14.19 |
| ~300 | 0 | 264.93 | 0.00 | ~300 | 0 | 270.90 | 0.00 |
|  | 10 | 261.38 | −1.34 |  | 10 | 268.91 | −0.73 |
|  | 20 | 259.23 | −2.15 |  | 25 | 266.47 | −1.63 |
|  | 32 | 261.03 | −1.47 |  | 40 | 267.91 | −1.10 |

TABLE 5

Effects of Added BRB and PAM on Output Currents

| Glucose (mg/dL) | Added BRB (mg/dL) | Currents (mV) | %-bias to blank | Glucose (mg/dL) | Added PAM (mg/dL) | Currents (mV) | %-bias to blank |
|---|---|---|---|---|---|---|---|
| ~80 | 0 | 63.37 | 0.00 | ~80 | 0 | 60.89 | 0.00 |
|  | 10 | 63.68 | 0.49 |  | 6 | 61.25 | 0.59 |
|  | 20 | 62.73 | -1.00 |  | 26 | 61.68 | 1.30 |
|  | 30 | 63.07 | -0.47 |  | 102 | 58.45 | -4.01 |
|  | 40 | 61.67 | -2.67 |  | 205 | 55.78 | -8.39 |
| ~300 | 0 | 259.27 | 0.00 | ~300 | 0 | 250.00 | 0.00 |
|  | 10 | 259.14 | -0.05 |  | 6 | 251.03 | 0.41 |
|  | 20 | 263.62 | 1.68 |  | 26 | 252.88 | 1.15 |
|  | 30 | 264.92 | 2.18 |  | 102 | 251.82 | 0.73 |
|  | 40 | 263.58 | 1.66 |  | 205 | 250.84 | 0.34 |

TABLE 6

Effects of Added XY on Output Currents (Two Studies)

| Glucose (mg/dL) | Added XY (mg/dL) | Currents (mV) | %-bias to blank | Glucose (mg/dL) | Added XY (mg/dL) | Currents (mV) | %-bias to blank |
|---|---|---|---|---|---|---|---|
| ~80 | 0 | 61.80 | 0.00 | ~50 | 0 | 36.04 | 0.00 |
|  | 50 | 92.50 | 49.67 |  | 50 | 64.94 | 80.18 |
|  | 100 | 119.53 | 93.40 |  | 200 | 149.29 | 314.21 |
|  | 200 | 174.48 | 182.32 | ~110 | 0 | 83.37 | 0.00 |
|  |  |  |  |  | 50 | 110.76 | 32.84 |
| ~300 | 0 | 262.64 | 0.00 |  | 200 | 187.45 | 124.82 |
|  | 50 | 294.03 | 11.95 | ~180 | 0 | 148.79 | 0.00 |
|  | 100 | 307.92 | 17.24 |  | 50 | 175.62 | 18.04 |
|  | 200 | 362.09 | 37.87 |  | 200 | 251.68 | 69.16 |

TABLE 7

Effects of Added Hb on Output Currents

| Glucose (mg/dL) | Added Hb (g/dL) | $i_{M6.5}$ Currents (mV) | %-bias to blank | $i_{H,4}$ Currents (mV) | %-bias to blank |
|---|---|---|---|---|---|
| 80 | 0 | 63.51 | 0.00 | 2227.07 | 0.00 |
|  | 3 | 63.95 | 0.68 | 2055.81 | -7.69 |
|  | 5 | 63.52 | 0.01 | 1906.98 | -14.37 |
|  | 12 | 63.88 | 0.58 | 1638.45 | -26.43 |
| 300 | 0 | 262.30 | 0.00 | 2201.15 | 0.00 |
|  | 3 | 264.69 | 0.91 | 2043.85 | -7.15 |
|  | 6 | 255.89 | -2.44 | 1903.95 | -13.50 |
|  | 12 | 234.10 | -10.75 | 1614.12 | -26.67 |

TABLE 8

Effects of Added Cholesterol on Output Currents

| Glucose (mg/dL) | Added CH (mg/dL) | $i_{M6.5}$ Currents (mV) | %-bias to blank | $i_{H,4}$ Currents (mV) | %-bias to blank |
|---|---|---|---|---|---|
| 80 | 0 | 63.81 | 0.00 | 2405.13 | 0.00 |
|  | 150 | 63.80 | -0.02 | 2267.65 | -5.72 |
|  | 250 | 62.59 | -1.91 | 2196.00 | -8.70 |
|  | 550 | 57.20 | -10.37 | 1933.59 | -19.61 |
| 300 | 0 | 273.23 | 0.00 | 2390.30 | 0.00 |
|  | 150 | 274.12 | 0.32 | 2278.51 | -4.68 |
|  | 250 | 267.42 | -2.13 | 2185.77 | -8.56 |
|  | 550 | 241.53 | -11.60 | 1903.99 | -20.35 |

Figure 20:
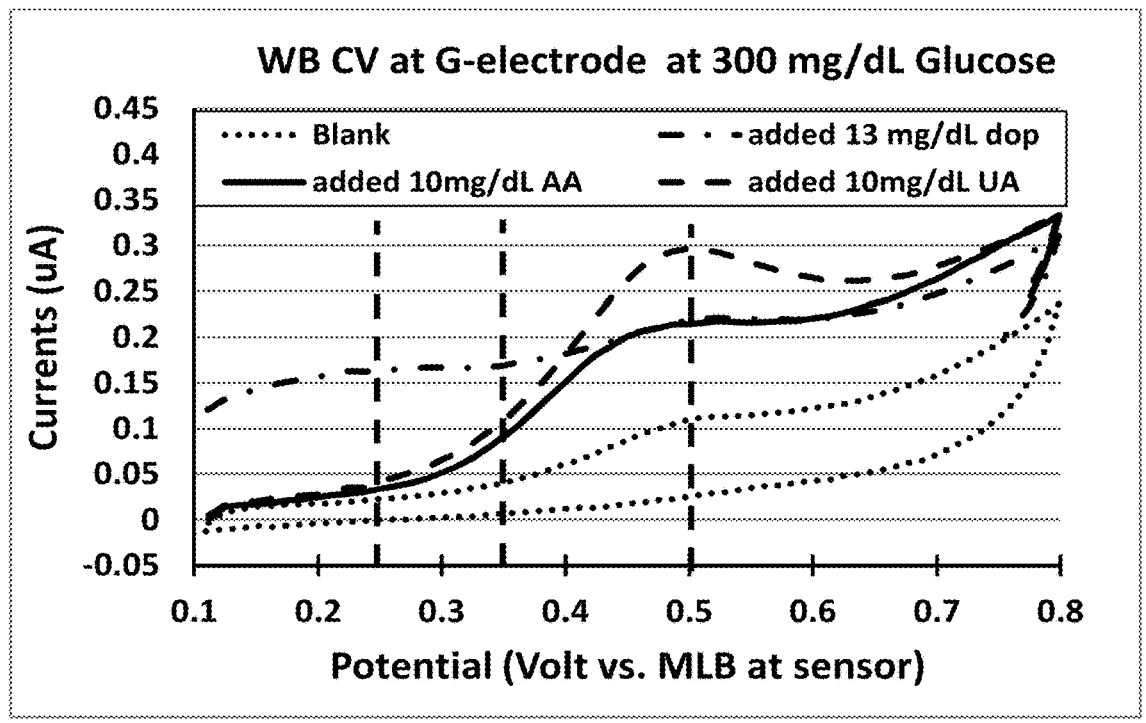
FIG. 20 is a graph illustrating voltammograms of Dop, AA, and UA added to a blank WB sample of 300 mg/dL glucose at 42% Hct, taken at the bare electrode, in accord with aspects of the present disclosure.

For comparison purposes, the voltammograms of a blank WB sample at 300 mg/dL of glucose, with separately added Dop of 13 mg/dL, added AA of 10 mg/dL, and added UA of 10 mg/dL to the WB blank are superimposed together in FIG. 20. As a reference, the main working electrode with reagent chemistry for glucose measurement is operated at 0.25 V, which is represented by the vertical line at 0.25 V in FIG. 20. The two other operation potentials at 0.35 V and 0.5 V are also represented by the vertical lines at these two positions. Since the second working electrode having no added reagent chemistry cannot oxidize the target analyte glucose, the blank voltammogram shows very low currents at the second electrode. With the addition of 13 mg/dL Dop to the blank WB sample of 300 mg/dL glucose, there is a large increase to the second electrode's output currents at 0.25 V. For AA and UA, on the other hand, there is virtually no change in current at 0.25 V in the voltammogram at the added level of 10 mg/dL of each species. The current increases are only at high potentials, such at 0.35 V and 0.5 V. Thus, Dop and ASA (not shown here) are oxidizable species that contribute positively to the output currents of the first working electrode (Table 3). From FIG. 20, AA and UA are not oxidizable at 0.25 V and, presumably, have little or no positive effect to the output currents of the first working electrode.

Referring to Table 3, the examples in this table show the positive effects from oxidizable interference species (Dop and ASA). The error (%-bias) in glucose is expected to be equivalent to that of the current error as a result. Typically, the effects of interference are more significant at low glucose concentrations (about 80-120 mg/dL). At high glucose concentrations (about 300 mg/d), the interference effects become less significant, or have no significance, as can be seen in both the ASA and Dop cases. Fortunately, the natural amount of Dop in human body is much lower than the concentrations tested (MTC/URV=0.04 mg/dL versus the lowest addition of 4 mg/dL). Note that MTC is the maximum therapeutic concentration for each potential interference species while URV is the upper reference value for the species. As a result of dopamine's MTC=0.04 mg/dL, there should be no clinical significance from Dop's interference even though Dop has the potential to give a relatively large positive %-bias at low glucose concentrations. On the other hand, ASA as an external substance may be taken in with food, such as drinking orange juice, and the instant concentration can be rather high. Other potential interference species that behave like Dop and/or ASA should have similar effects on the output currents.

Table 4 provides examples of the effects from interference species (AA and UA) that are seemingly not oxidizable at the potential equivalent to the first electrode having the reagent chemistry for the target analyte (e.g., 0.25 V). Even though voltammograms of AA and UA show very little activity at 0.25 V, the interference tests with added AA and UA do show slightly negative effects for AA and moderately negative effects for UA at the glucose level of 80 mg/dL. These subtle negative effects cannot be predicted by the simple voltammetric behavior of the individual interference species (AA and UA in FIG. 20), and a better method is needed for detection of AA and UA, instead of relying on simply avoiding the oxidation of these species.

Table 5 provides examples of the effects from the added BRB and PAM. While there is no effect from the added BRB, the added PAM had a slightly negative effect on the $i_{M6,5}$ current. The behavior of the glucose sensor with the added PAM is similar to that with UA and consideration should be given to the subtle effects from PAM.

Table 6 provides two sets of xylose interference tests. Positive biases from xylose are due to the sensitivity to xylose of the glucose dehydrogenase enzyme (FAD-GDH). The positive error from xylose is significant at low glucose concentrations, but becomes diminishing at high glucose concentrations. The use of xylose is mainly in the gastrointestinal malabsorption test, which is declining recently. Nonetheless, the xylose interference effect can be substantial if encountered.

Table 7 provides test results for the Hb interference study. While the effects on the main electrode ($i_{M6,5}$ currents) range from none at low glucose to slightly negative at high glucose, the major effect is shown on the hematocrit signal $i_{H,4}$. Where the blank sample is at 42% Hct, a negative bias of −26% of the $i_{H-4}$ currents relative to the blank sample at high added Hb level of 12 g/dL would represent a hematocrit level of 55% and, thus, would lead to over compensation based on the $i_{H,4}$ currents.

Table 8 provides test results for the cholesterol interference study. While the effects of the highest added level of cholesterol on the main electrode currents ($i_{M6,5}$) is moderately at ~−10% for both 80 and 300 mg/dL baseline glucose, the effects of the moderate additions of cholesterol (150-250 mg/dL) on the output currents for the target analyte electrode tend to be negative but are negligibly small. However, there are moderate to high negative impacts on the Hct signals (current $i_{H-4}$) with increasing additions of cholesterol to both 80 and 300 mg/dL baseline glucose. These changes in the Hct signals are enough to cause erroneous determinations of the target analyte through their inputs in the compensation equation.

Given the subtle influences of the individual species on the output currents of the first working electrode, conducting a simple subtractive compensation by inputting the currents from the second working electrode proportionally into a compensation algorithm for the output currents of the first working electrode may not be effective. Systematically, managing the interference effects of various interference species can be accomplished by sorting the data in terms of one or more signals, and/or one or parameters related to interference detection. Below is an example of sorting and separating the normal data and the interference data in terms of relevant parameters. The interference species of a more or less oxidative nature can be categorically characterized by the bare electrode pulse ratios, such as $RG_{14}$ ($i_{G1,4}/i_{G4,4}$ at 0.25 V and 1.0 V, respectively), $RG_{24}$ ($i_{G2,4}/i_{G4,4}$ at 0.35 V and 1.0 V, respectively), and $RG_{34}$ ($i_{G3,4}/i_{G4,4}$ at 0.5 V and 1.0V, respectively). These parameters are plotted in FIGS. 21A and 21B in their full range as a result of the interference tests. Since the electrochemical pulse at 1.0 V in WB samples provides relatively constant currents, taking ratios of the currents at 0.25 V, 0.35 V, and 0.5 V to the currents at 1.0 V normalizes the interference effects at different potentials for all oxidizable species. One way of showing the interference effects of various species is to plot $RG_{34}$ versus $RG_{14}$ and $RG_{24}$ versus $RG_{14}$. These plots are shown in FIGS. 21A and 21B for the interference species of Dop, ASA, AA, UA, BRB, and XY, along with the data from lab studies and donor studies.

Figure 21A:
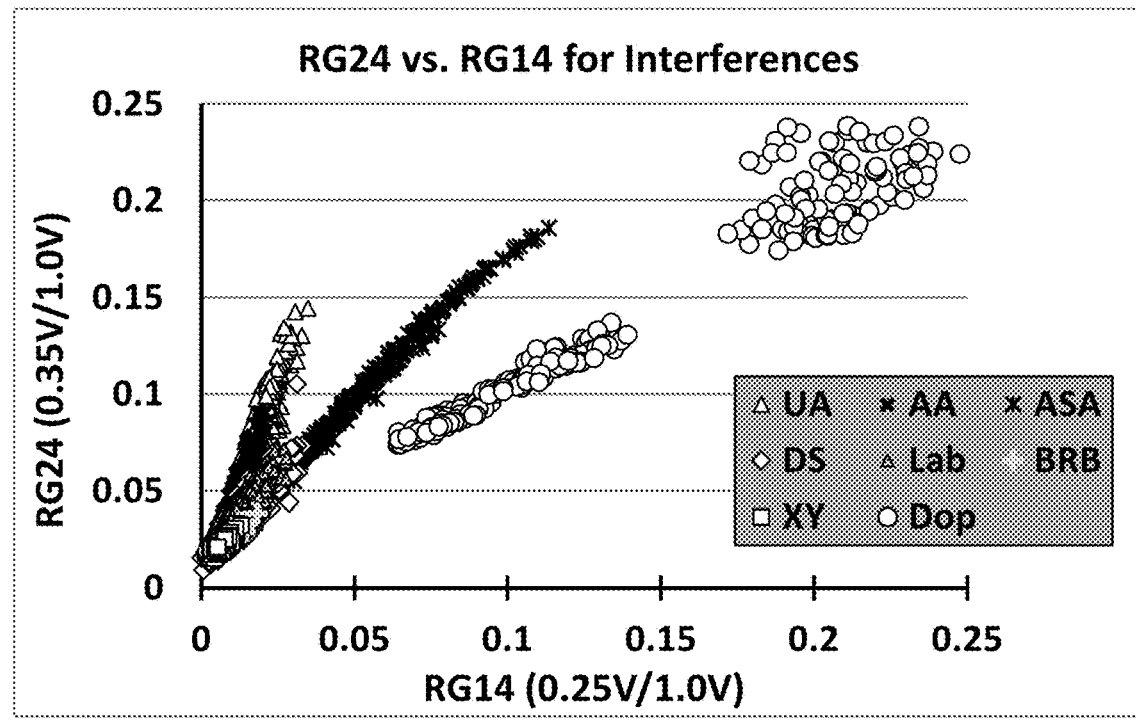
FIG. 21A shows a plot of the parameters $RG_{34}$ versus $RG_{14}$ for the entire range of $RG_{34}$ and $RG_{14}$ resulted from tests for interference species in comparison to data points from lab studies (Lab) and donor studies (DS), in accord with aspects of the present disclosure.
Figure 21B:
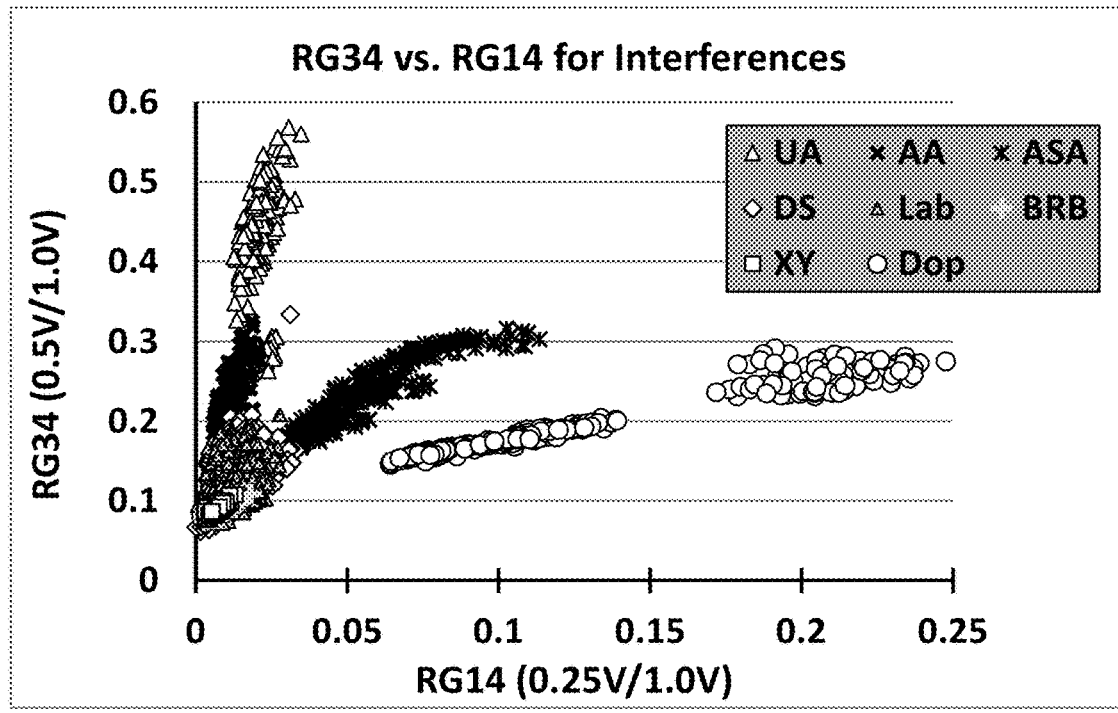
FIG. 21B shows a plot of the parameters $RG_{34}$ versus $RG_{14}$ for a subset range of $RG_{14}$ resulted from the tests for interference species in comparison to the data points from Lab and DS, in accord with aspects of the present disclosure.
Figure 21C:
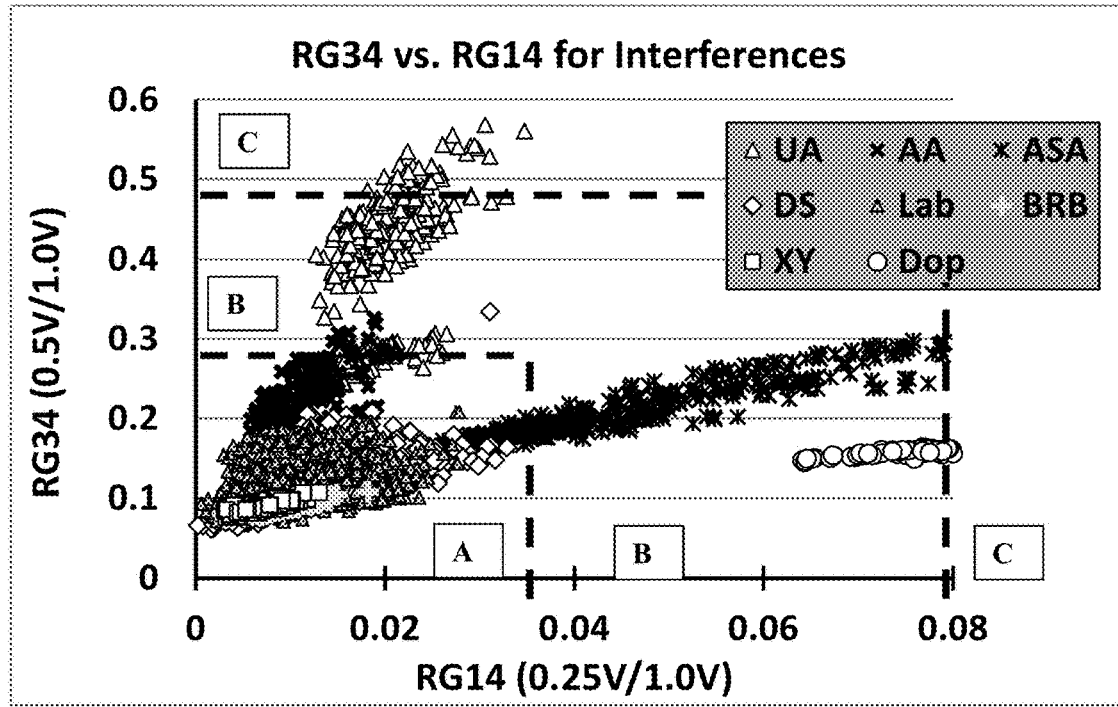
FIG. 21C shows a plot of the parameters $RG_{34}$ versus $RG_{14}$ for subset ranges of $RG_{34}$ and $RG_{14}$ for interference species in comparison to the data points from Lab and DS, in accord with aspects of the present disclosure.
Figure 21D:
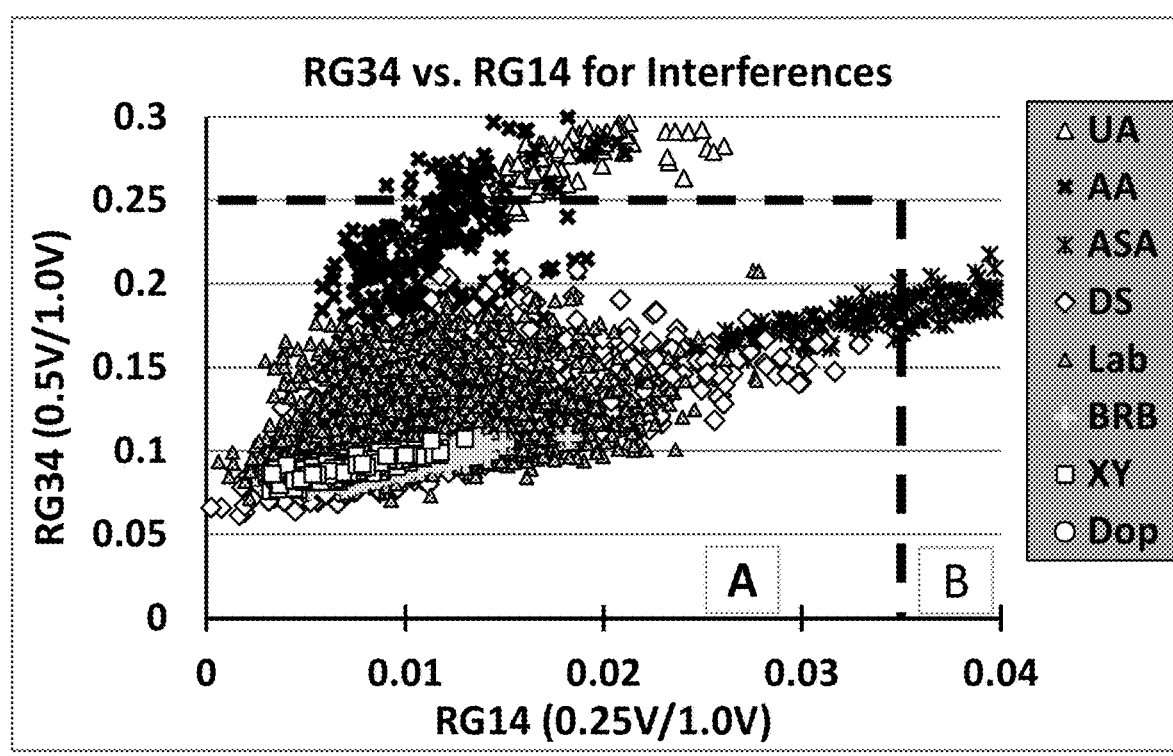
FIG. 21D shows a plot of the parameters $RG_{34}$ versus $RG_{14}$ for interference species in comparison to the data points from Lab and DS, in accord with aspects of the present disclosure.

It can be seen from FIGS. 21A and 21B that data points from lab and donor studies with no or low interference species present (the normal data) are located at the lower left corner effectively within about 0-0.035 $RG_{14}$ and about 0-0.25 $RG_{34}$. More detail distribution of the different species can be seen in FIG. 21C and further in FIG. 21D with the expanded x- and y-axes. For the non-electrochemically oxidizable species BRB and xylose, they are also within this region. However, for the electrochemically active species before, at, and beyond 0.25 V (or the same operation potential of the first working electrode), such as Dop and to a lesser extent ASA, the data is expressed along the horizontal direction, extending along the $RG_{14}$ axis. On the other hand, for the electrochemically less active species at 0.25 V but more active at higher potentials, such as AA and UA, the data is expressed along the vertical direction extending along the $RG_{34}$ axis. This characteristic is expressed more in FIG. 21B in the plot of $RG_{34}$ versus $RG_{14}$. The threshold values of separation between the normal and interference data are stored at the biosensor system memory storage. Once a data set is measured, the relevant parameters are computed and compared to the threshold values. The interference species is detected categorically by reference to these threshold values such that identification of the exact interference species is not necessary. Species other than Dop, ASA, UA, and AA may be detected as long as their relevant parameters fall in the defined regions of the $RG_{34}$ versus $RG_{14}$ or $RG_{24}$ versus $RG_{14}$ domains, such as the one in FIGS. 21C and 21D. Based on comparisons of the relevant parameters to the pre-set threshold values, the biosensor system can be directed to make a decision on calculating and reporting a glucose reading based on a normal compensation algorithm, providing a warning for the end-user, compensating for the interference effect, rejecting the test result, or combination thereof.

Figure 21E:
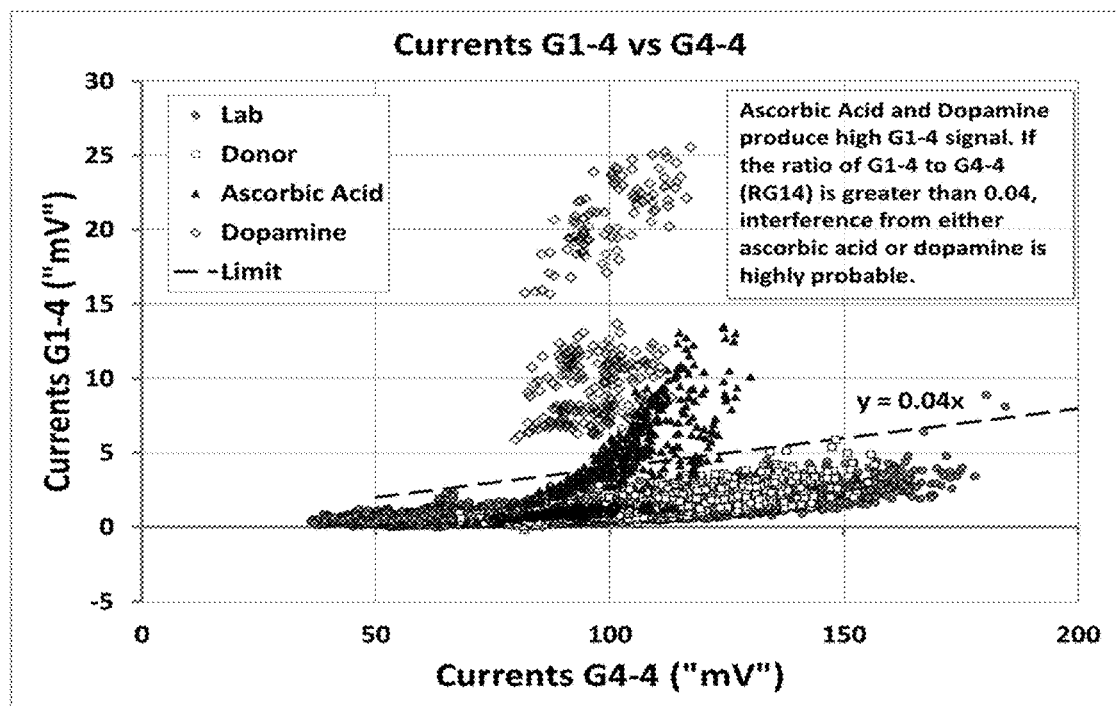
FIG. 21E shows a plot of sorting and separating of currents $i_{G1,4}$ versus $i_{G4,4}$ for ASA and Dop, in accord with aspects of the present disclosure.
Figure 21F:
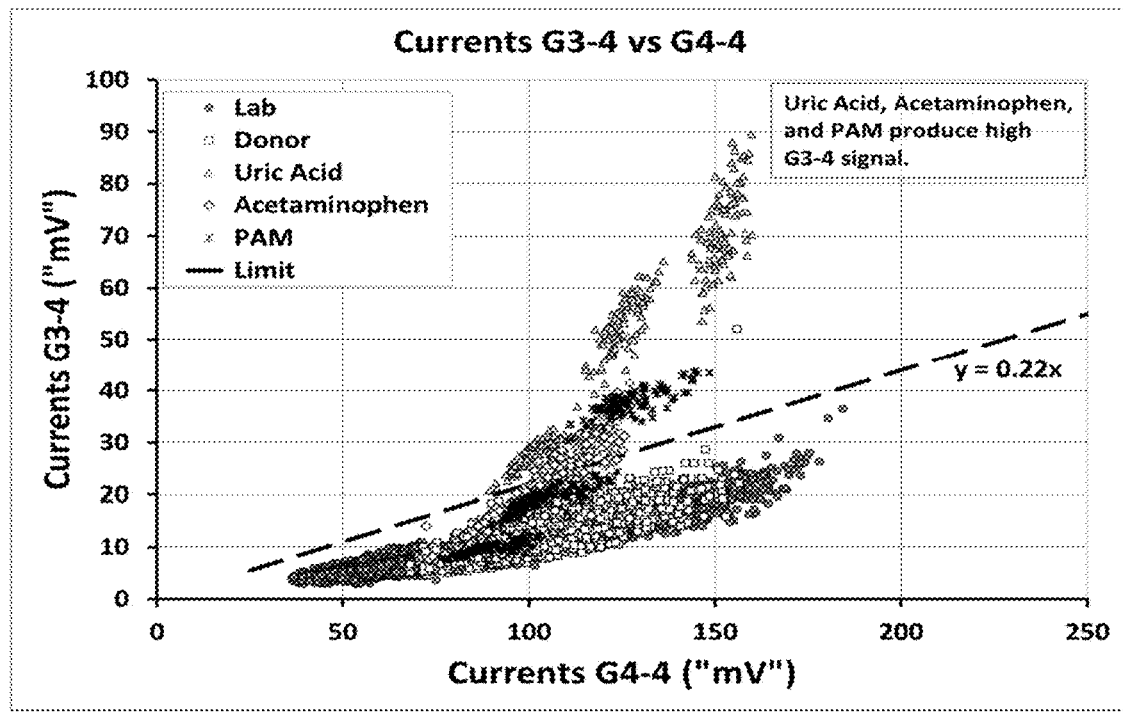
FIG. 21F shows a plot of the sorting and separation of currents $i_{G3,4}$ versus $i_{G4,4}$ for AA, UA, and pralidoxime iodide (PAM), in accord with aspects of the present disclosure.
Figure 21G:
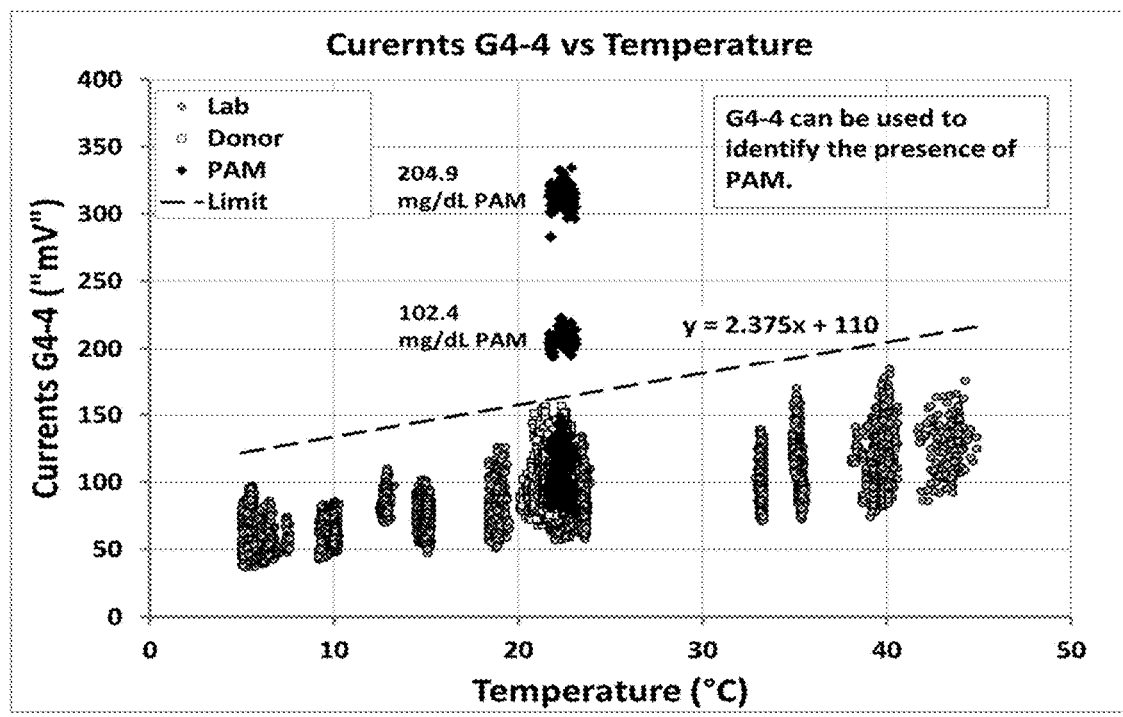
FIG. 21G shows a plot of the sorting and separation of currents $i_{G4,4}$ versus temperatures for PAM, in accord with aspects of the present disclosure.
Figure 21H:
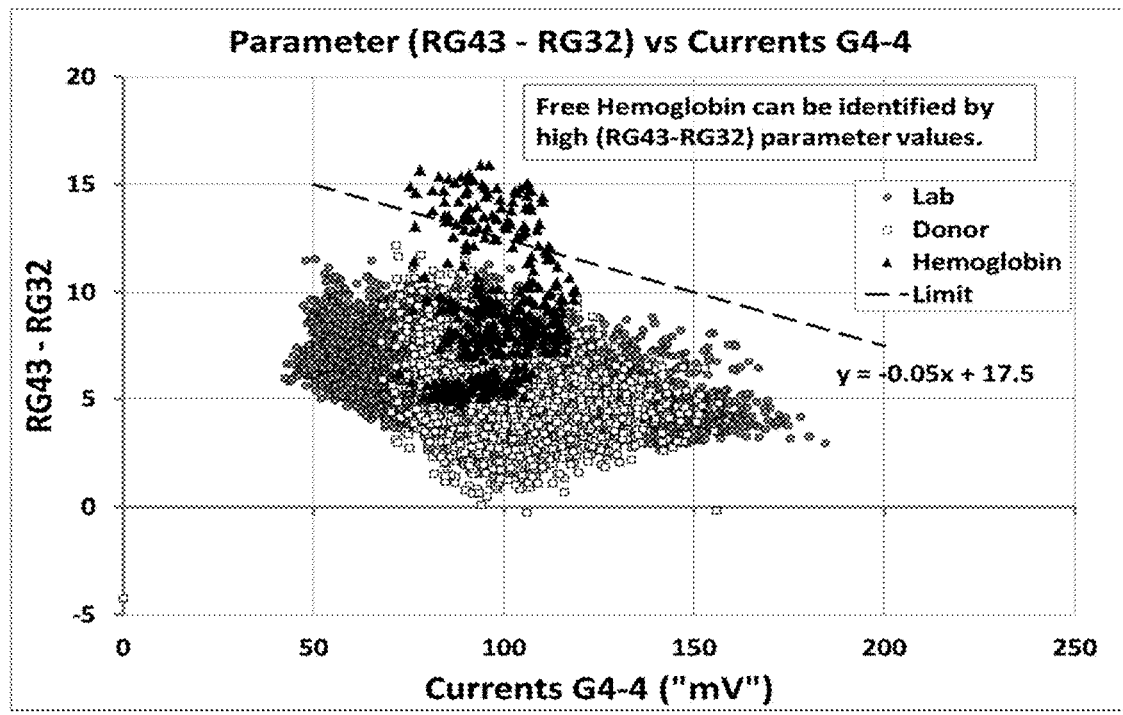
FIG. 21H shows a plot of the sorting and separation of the parameter $(RG_{43}-RG_{32})$ versus $i_{G4,4}$ for hemoglobin (Hb), in accord with aspects of the present disclosure.

Equally important is the sorting and separation of the interference data from normal data in terms of measured signals, which are presented in example plots in FIG. 21E-21H. In all figures, "Lab" represents the data acquired from lab tests at temperatures of 5-45° C., hematocrits of 0-70%, and glucose at 50 to 600 mg/dL at discrete levels. "Donor" represents data from internal donor studies with random glucose concentrations and hematocrit levels at ambient room temperatures (20-24° C.). The individual interference test results are shown in Tables 1-8. FIG. 21E represents the sorting and separation of ASA and Dop data from the lab and donor study data in terms of currents $G_{14}$ and currents $G_{44}$. Since the $G_1$ pulse is operated at the same potential of 0.25 V as the main pulses $M_3$, $M_4$, $M_5$, and $M_6$, positive signals above the separation limit defined by the line Y=0.04*x (where y is $i_{G1,4}$ and x is $i_{G4,4}$) signify the intolerable interference levels for normal calculation/compensation of the analyte concentrations from these two species. Similarly, FIG. 21F represents the sorting and separation of AA, UA, and PAM data from the lab and donor study data in terms of currents $G_{34}$ and currents $G_{44}$. Since the $G_3$ pulse is operated at the 0.5 V potential probing the distance neighborhood of the operation potential at 0.25 V of the main electrode, positive signals above the separation limit defined the line Y=0.22*x (where y is $i_{G3,4}$ and x is $i_{G4,4}$) also signify the intolerable interference levels for normal calculation/compensation of the analyte concentrations from these species. Furthermore, FIG. 21G presents the sorting and separation of PAM data from the lab and donor study data in terms of currents $i_{G4,4}$ versus temperature. The high currents $i_{G4,4}$ provide a unique identification of this interference species. Finally, FIG. 21H presents the sorting and separation of Hb data from the lab and donor study data in terms of parameter $RG_{43}$-$RG_{32}$ versus currents $i_{G4,4}$. This is a unique example of sorting and separation by combining the parameter and measured signals. In all examples, a special algorithm emphasizing the high levels of interference signals is used for the calculation/compensation, instead of the normal calculation/compensation algorithm.

Based on data distributions of the normal samples from lab studies and donor studies, as well as the those from interference species, a strategy for interference detection, compensation, and rejection was determined as follows: (A) if the $RG_{14}$ value is below $RG_{14}$_limit1 (0.035, for instance) and $RG_{34}$ value below $RG_{34}$_limit1 (0.3, for instance), normal compensation to the raw signals and the output results from a conversion function, as provided by the primary and residual compensations, is performed; (B) if the $RG_{14}$ value is between $RG_{14}$_limit1 (0.035) and $RG_{14}$_limit2 (0.08, for example), and $RG_{34}$ value between $RG_{34}$_limit1 (0.3) and $RG_{34}$_limit2 (0.6, for example), a special compensation is provided with significant inputs from these and other relative parameters to remove the effects on the output signals of the first working electrode; and (C) if the $RG_{14}$ value is outside the $RG_{14}$_limit2, or the $RG_{34}$ value is outside the $RG_{34}$_limit2, rejection of the data point can occur. These three regions are depicted in FIG. 21A.

Figure 22A:
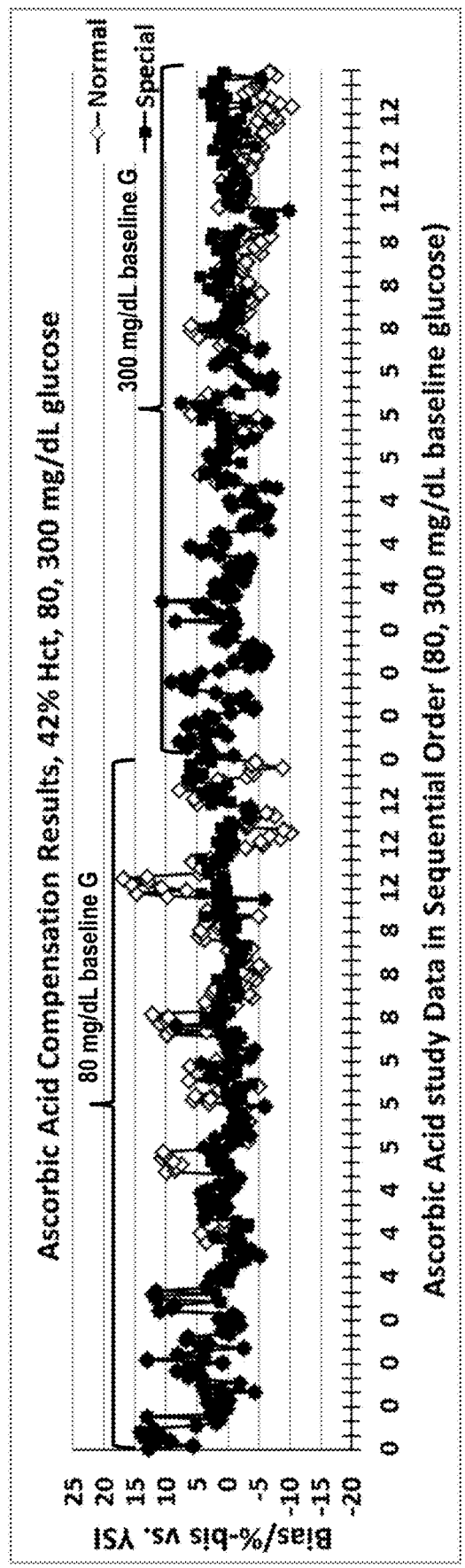
FIG. 22A shows a plot of the compensation results of a special algorithm in comparison to the compensation results of a normal algorithm for ASA, in accord with aspects of the present disclosure.
Figure 22B:
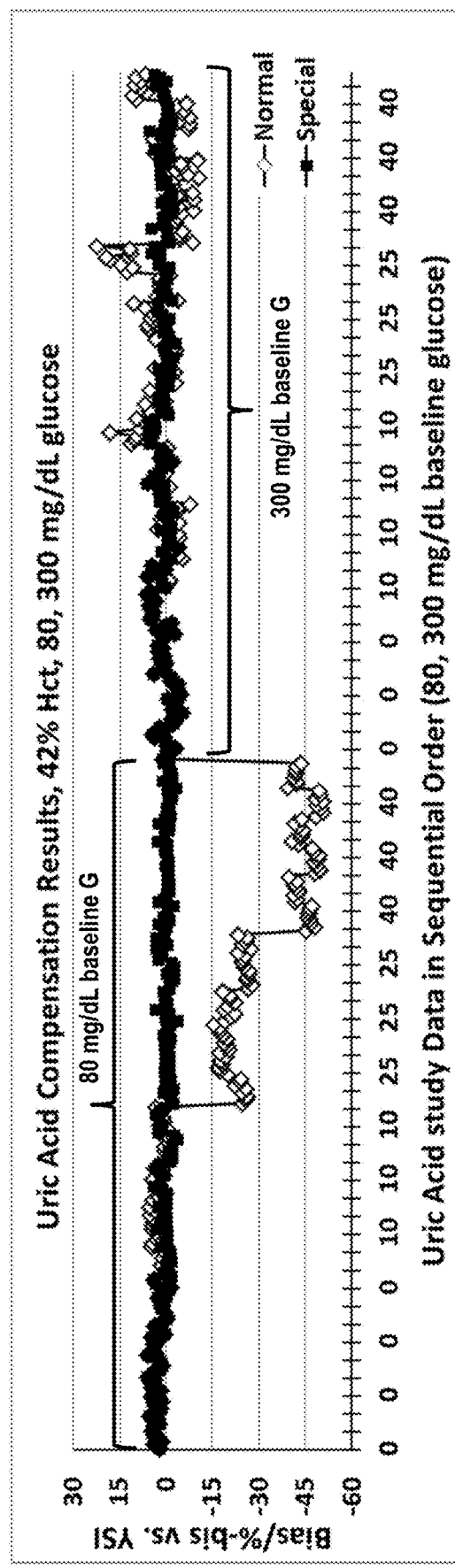
FIG. 22B shows a plot of the compensation results of the special algorithm in comparison to the compensation results of the normal algorithm for UA, in accord with aspects of the present disclosure.
Figure 22C:
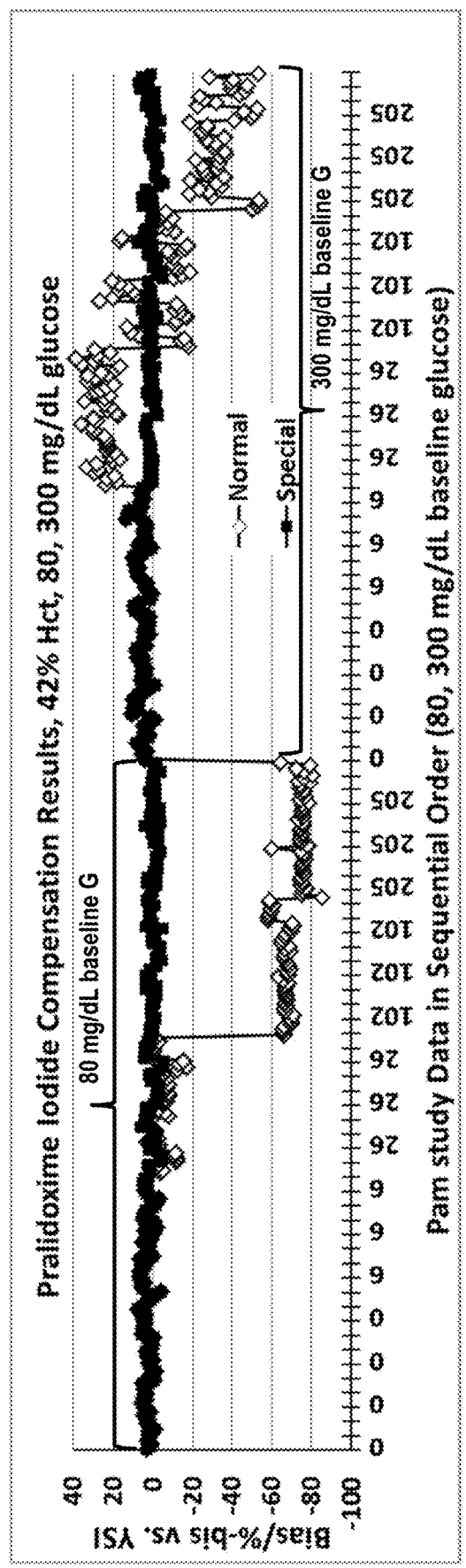
FIG. 22C shows a plot of the compensation results of the special algorithm in comparison to the compensation results of the normal algorithm for PAM, in accord with aspects of the present disclosure.
Figure 22D:
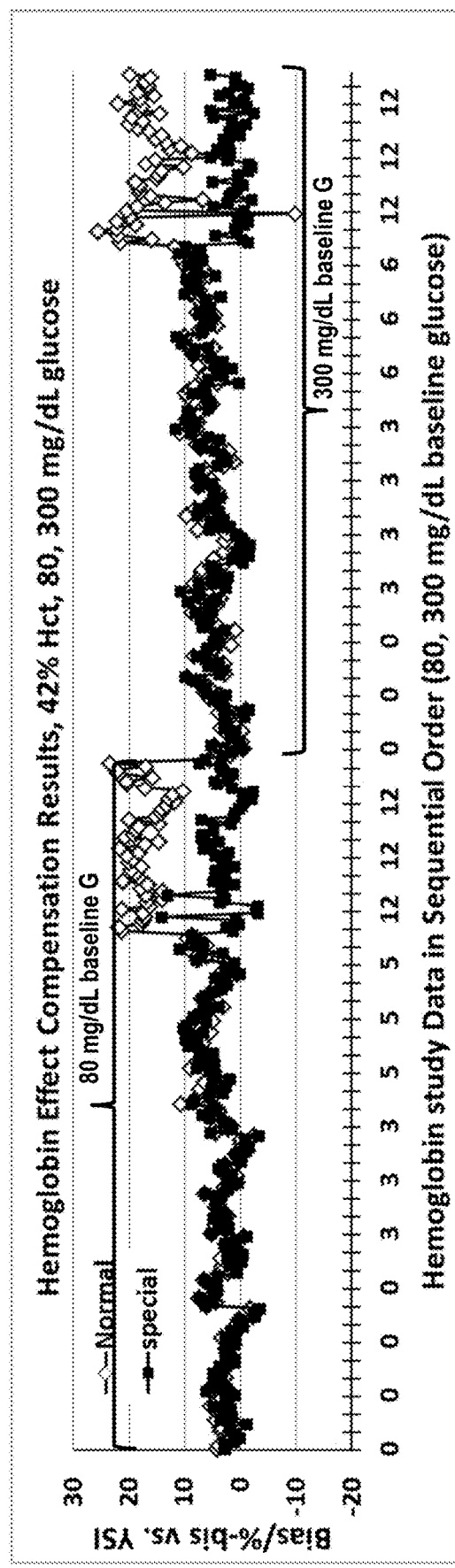
FIG. 22D shows a plot of the compensation results of the special algorithm in comparison to the compensation results of the normal algorithm for Hb, in accord with aspects of the present disclosure.

Referring to FIGS. 22A-22D, these figures present examples of compensation results with the special algorithm in comparison to compensation results with the normal algorithm for various different interference species, according to aspects of the present disclosure. Specifically, FIG. 22A shows the compensation results of the special algorithm in comparison to the compensation results of the normal algorithm for ASA. FIG. 22B shows the compensation results of the special algorithm in comparison to the compensation results of the normal algorithm for UA. FIG. 22C shows the compensation results of the special algorithm in comparison to the compensation results of the normal algorithm for PAM. FIG. 22D shows the compensation results of the special algorithm in comparison to the compensation results of the normal algorithm for Hb. The x-axes in FIGS. 22A-22D represent the added concentrations of ASA, UA, PAM, and Hb, respectively, in mg/dL for ASA, UA, and PAM and g/dL for Hb for each of the two baseline glucose concentrations, namely 80 mg/dL (data points left of center on the x-axes) and 300 mg/dL (data points right of center on the x-axes), where repeated x-axes values represent multiple data points for the same concentration of the interference species (e.g., ASA, UA, PAM, and Hb). For the normal compensation results, the large biases may be seen with high added interference levels, such as at 8 and 12 mg/dL of ASA of 80 mg/dL baseline glucose, 25 and 40 mg/dL of added UA, 102 and 205 mg/dL of added PAM, and 12 g/dL of added hemoglobin. Interference management for ASA and UA can rely on the boundary values in the sorting and separation shown in FIG. 21C, while that for PAM and Hb can rely on the boundary values in the sorting separation shown in FIGS. 21F and 21G, respectively.

For the detection of xylose, however, signals from direct electrochemical oxidation are not readily available from the second electrode having no added reagent, and thus detecting and isolating the xylose interference effects become difficult if not impossible based on the conventional method. Using enzymes that are insensitive to xylose has been the only choice in avoiding the xylose effect. However, according to the concepts of the present disclosure, it is demonstrated that, by processing the output signals from the intertwined input signals, certain ranges of xylose can be detected and glucose readings contaminated with xylose can be rejected based on certain criteria.

Figure 23A:
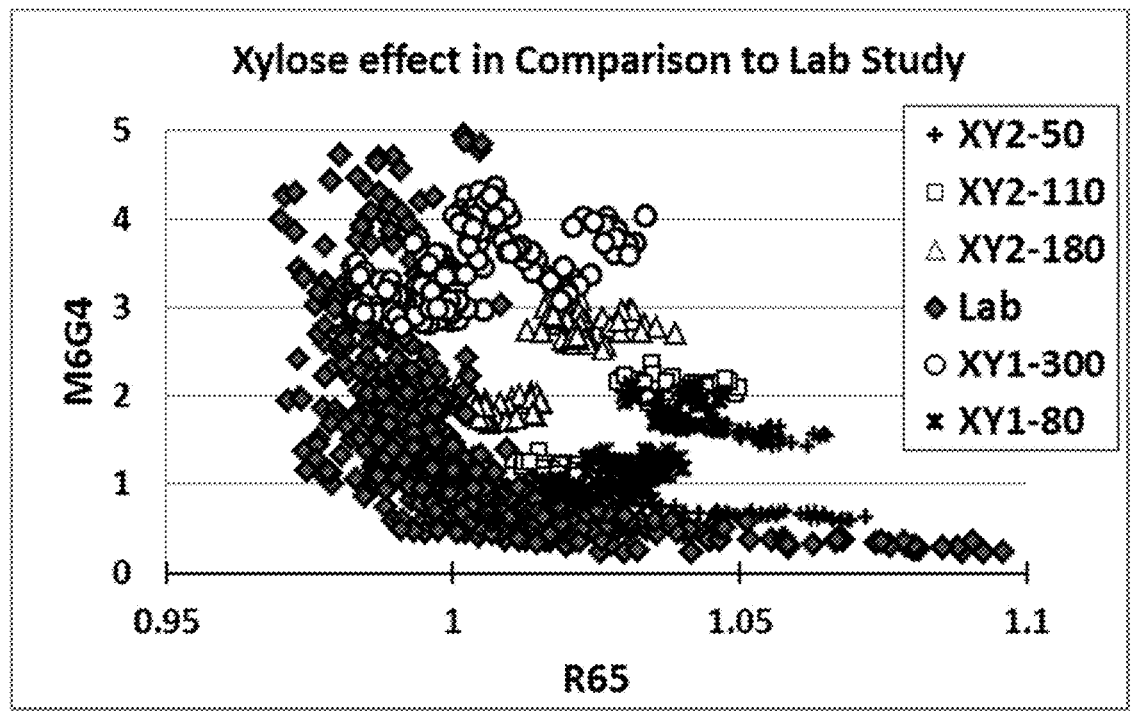
FIG. 23A shows a plot of the parameters $M_6G_4$ versus $R_{65}$ for xylose interference study data in comparison to the data from a lab study (Lab), in accord with aspects of the present disclosure.
Figure 23B:
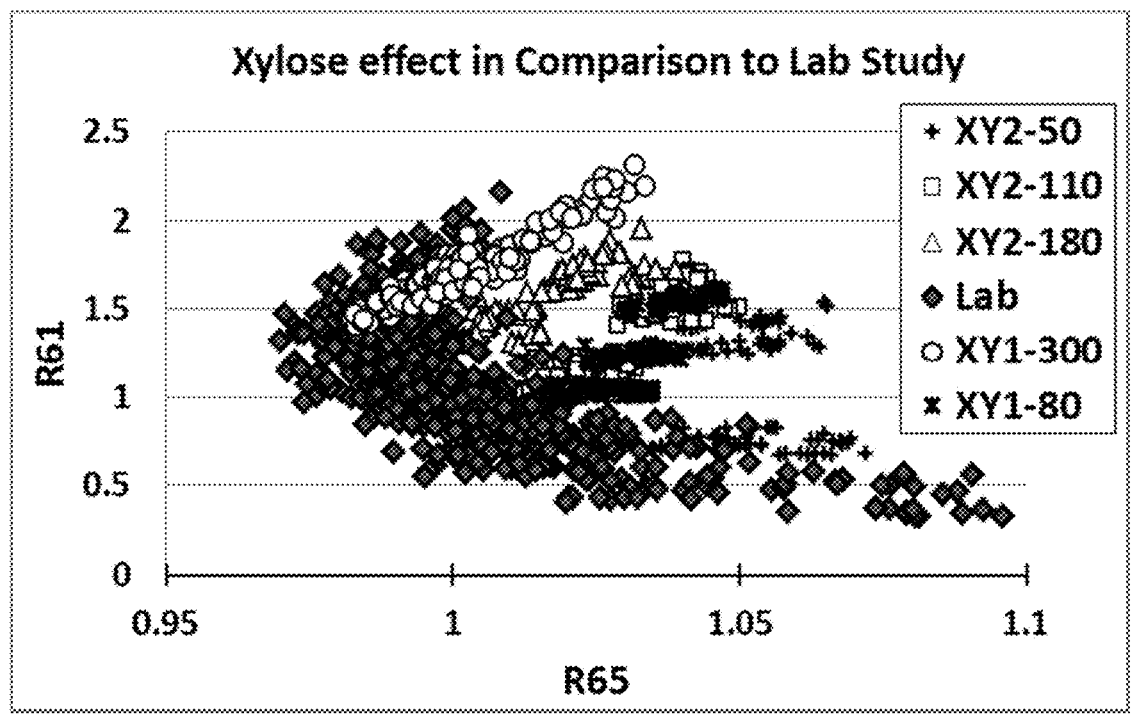
FIG. 23B shows a plot of the parameters $R_{61}$ versus $R_{65}$ for xylose interference study data in comparison to the data from a lab study (Lab), in accord with aspects of the present disclosure.

FIGS. 23A and 23B are graphs that show how detecting xylose at highly biased levels at room temperature (RT) is possible with information from processing output signals of the first, second and/or combination of both, in accord with aspects of the present disclosure. In the graphs of FIGS. 23A and 23B, the parameters $M_6G_4$ and $R_{61}$ (as defined above) are plotted against the parameter $R_{65}$ (also as defined above) for data from lab studies, and xylose interference studies at 80 or 300 mg/dL baseline glucose below. These parameters are based on the first output signals in relation to the second output signals.

FIG. 23A shows a plot of $M_6G_4$ ($M_6G_4=i_{M6,5}/i_{G4,4}$) versus $R_{65}$ for data from a normal lab study (fresh venous samples and altered venous samples tested at room temperature of 22±2° C., with glucose ranging from 43 to 600 mg/dL and %-Hct ranging from 20 to 60%) and data from two xylose interference studies at room temperature and 42% Hct (xylose Study 1: added xylose of 0, 50, 100, and 200 mg/dL to the WB samples of 80 and 300 mg/dL baseline glucose; xylose Study 2: added xylose of 0, 50 and 200 mg/dL to the WB samples of 50, 110 and 180 mg/dL baseline glucose). FIG. 23B shows a plot of $R_{61}$ versus $R_{65}$ for data from the same studies.

It can be seen from FIGS. 23A and 23B that both parameters $M_6G_4$ and $R_{61}$ against $R_{65}$ provide very noticeable patterns for detecting and isolating xylose from the normal glucose data. Without wishing to be bound by any theory, these two plots highlight two different xylose WB behaviors with respect to the xylose detection. First, there may be some rate difference in the enzyme reactions towards glucose and xylose at a short time and a later time. This is captured by the inter-pulse ratios of $R_{61}$ and $R_{65}$ and is plotted in $R_{61}$ versus $R_{65}$, where the inter-pulse ratios of the last pulse to pulse 1 and to the pulse 5 may provide subtle recording of this rate differences at earlier and later times. Secondly, there may be some subtle effect of xylose on the bare electrode pulse currents at various potential pulses, but to a larger extent at 1.0 V. This subtle effect is expressed as the depressed output signals relative to the normal WB samples. Subsequently, the ratios of pulse $M_6$ to pulse $G_4$ effectively rise above the normal WB sample data in the $M_6G_4$ versus $R_{65}$ plot.

According to FIGS. 23A and 23B, both plots can provide for detection of xylose. However, FIG. 23B represents an example of detecting xylose with measured signals from the main electrode alone (the electrode having reagent chemistry for the target analyte, such as glucose) without the G pulse signals. This detection method can be implemented with the general gated amperometry method, which is incorporated by reference here.

Figure 24A:
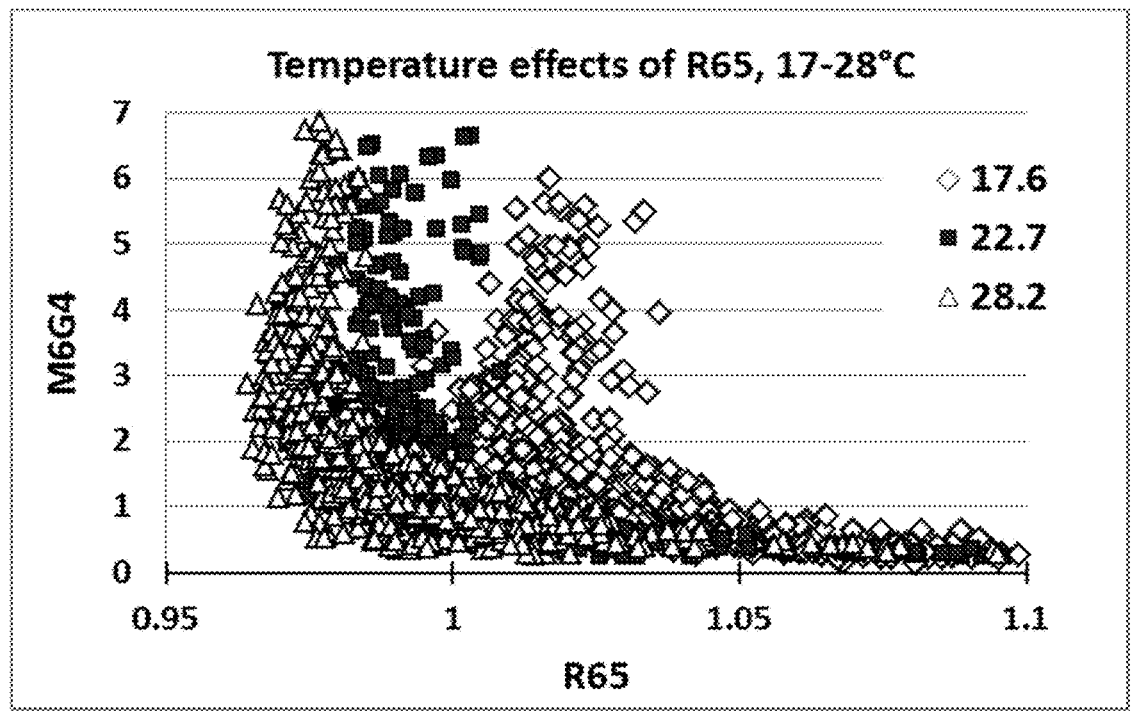
FIG. 24A shows a plot of the temperature effects of $R_{65}$ with data taken from lab tests of WB samples at 17, 23, and 28° C. using CONTOUR® NEXT strips by Ascensia Diabetes Care of Parsippany, N.J., in accord with aspects of the present disclosure.
Figure 24B:
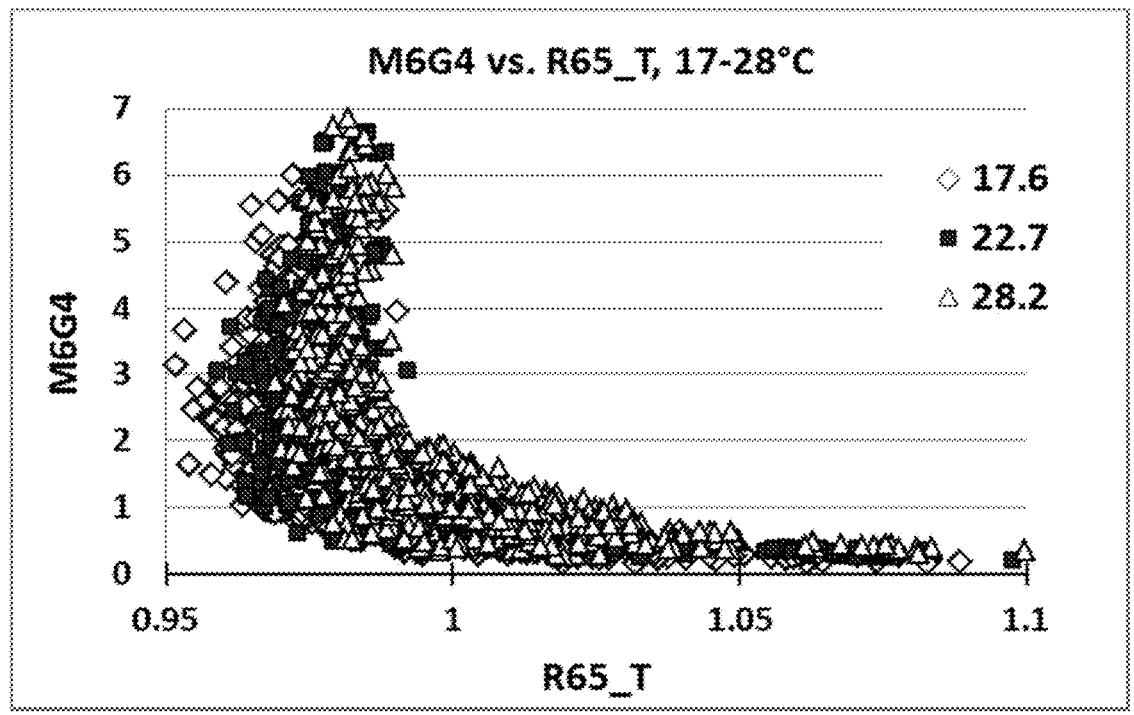
FIG. 24B shows a plot of parameters $M_6G_4$ versus $R_{65}\_T$ after temperature correction for $R_{65}$, in accord with aspects of the present disclosure.
Figure 24C:
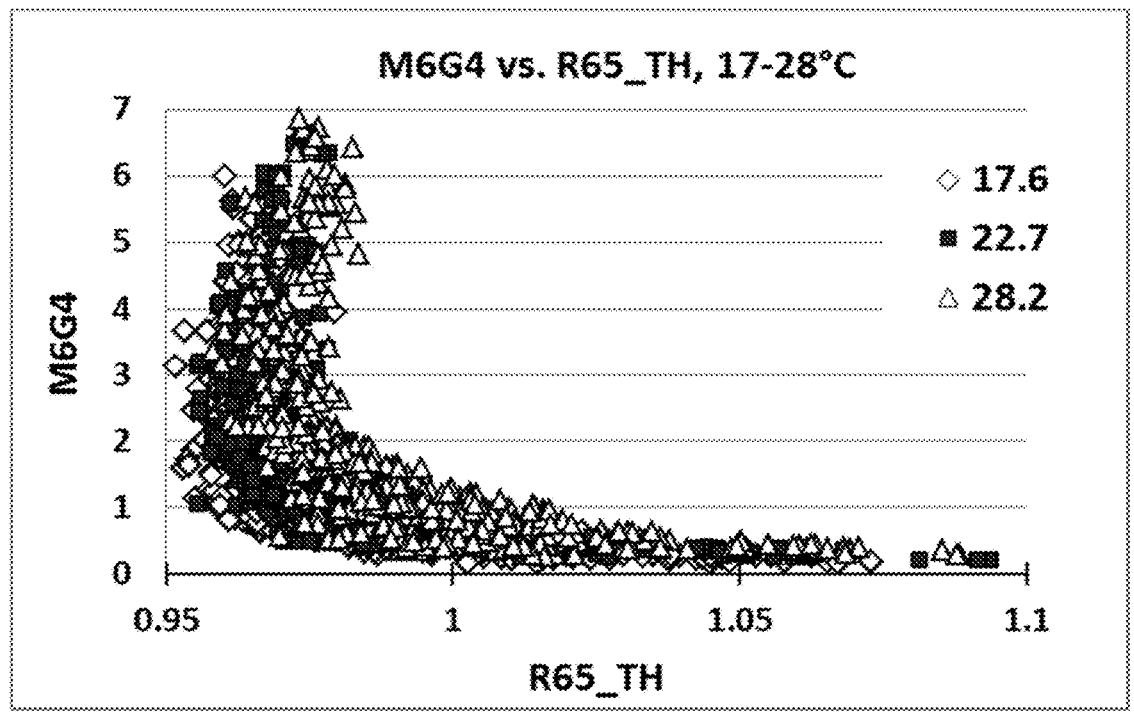
FIG. 24C shows a plot of the parameters $M_6G_4$ versus $R_{65}\_TH$ after adjusting for the hematocrit effect of $R_{65}\_T$, in accord with aspects of the present disclosure.
Figure 24D:
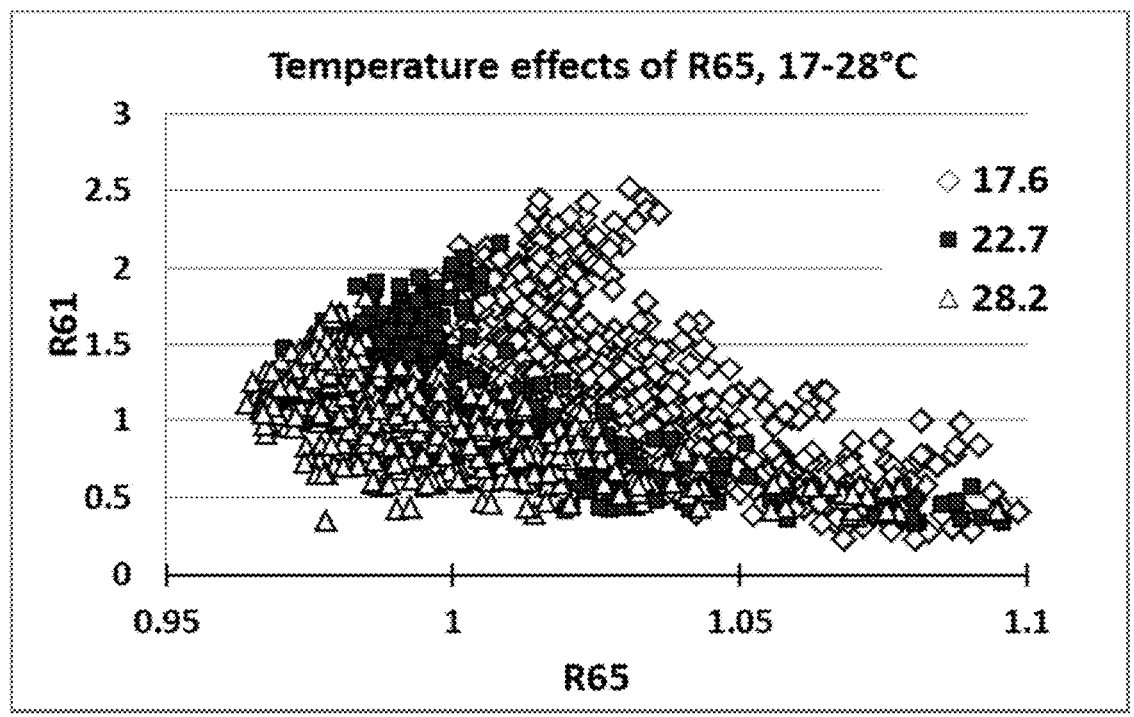
FIG. 24D shows a plot of the average temperature effect of $R_{65}$ with data from five different lab studies, in accord with aspects of the present disclosure.
Figure 24E:
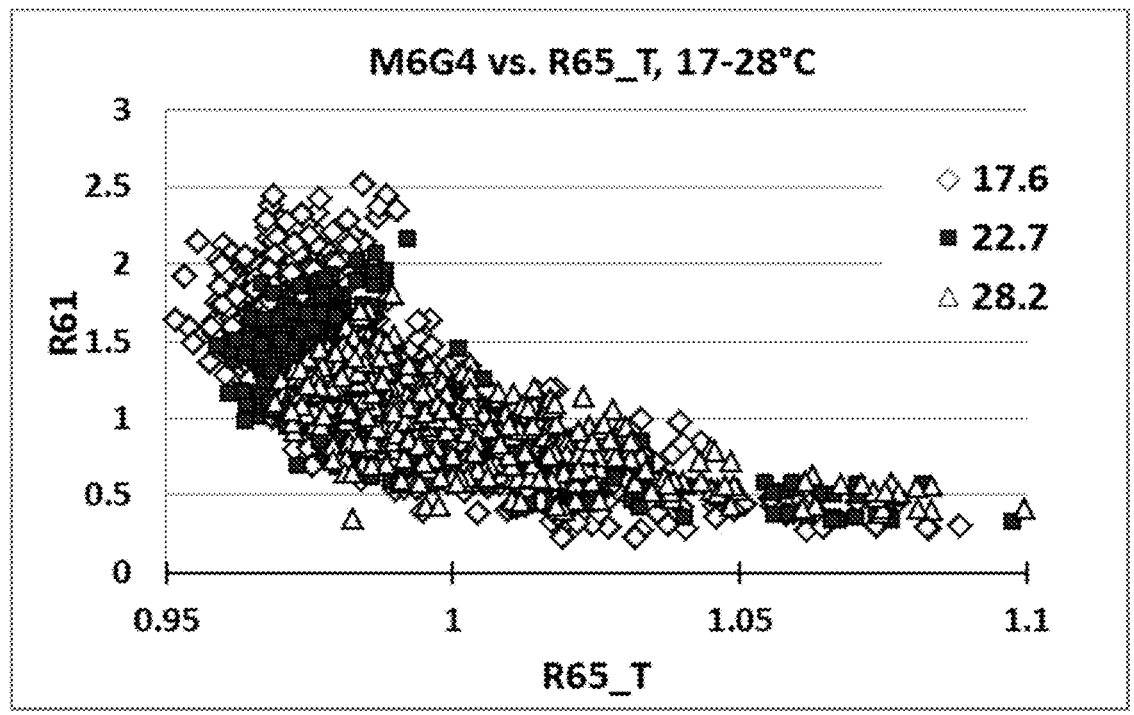
FIG. 24E shows a plot of the temperature function of $R_{65}$ in terms of $\ln(R_{65})$ (left axis), and the stepwise temperature coefficients of $R_{65}$ (right axis), in accord with aspects of the present disclosure.
Figure 24F:
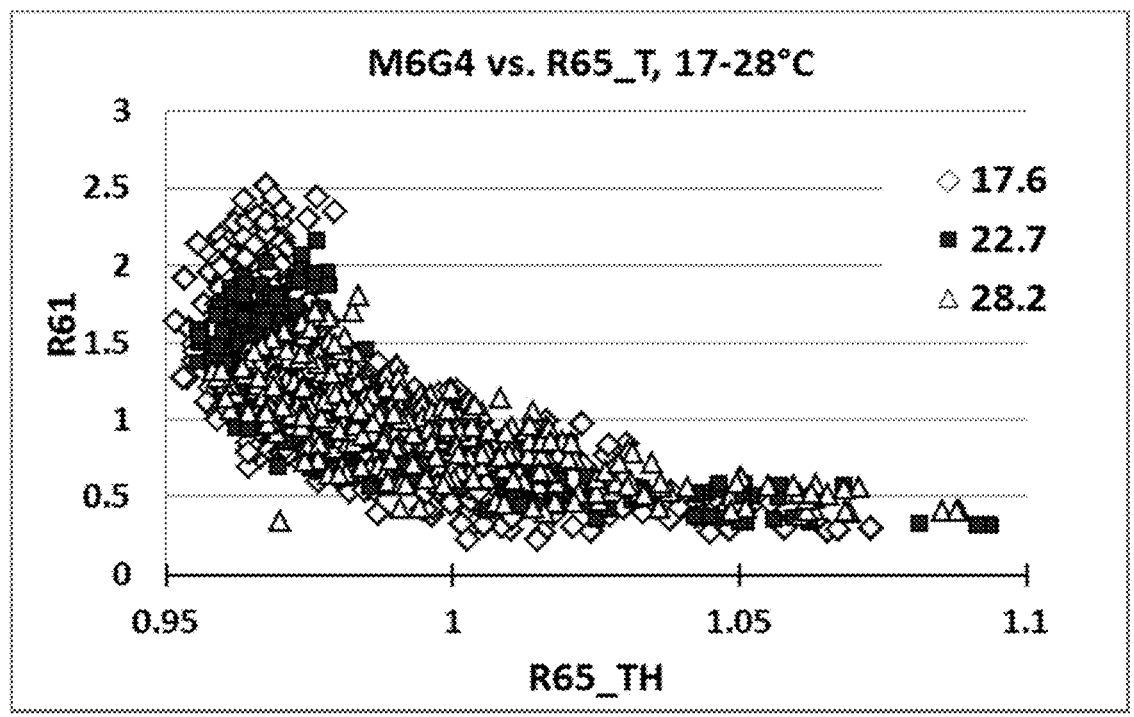
FIG. 24F shows a plot of the parameters $R_{61}$ versus $R_{65}\_TH$ after adjusting for the hematocrit effect of $R_{65}\_T$, in accord with aspects of the present disclosure.

Sorting and separating the normal data from the interference data for xylose can be further improved by adjusting the $R_{65}$ values through temperature correction of the $R_{65}$ values. FIGS. 24A-24C show $M_6G_4$ versus $R_{65}$ plots before and after the correction of temperature effects, and after the correction for temperature and hematocrit effects. Specifically, FIG. 24A shows the relationship of $M_6G_4$ versus $R_{65}$ before temperature correction. FIG. 24B shows the relationship of $M_6G_4$ versus $R_{65}$ after temperature correction. FIG. 24C shows the relationship of $M_6G_4$ versus $R_{65}$ after temperature correction and hematocrit correction. Similarly, FIGS. 24D-24F show $R_{61}$ versus $R_{65}$ plots before and after the correction of temperature effects, and after the correction for temperature and hematocrit effects. Specifically, FIG. 24D shows the relationship of $R_{61}$ versus $R_{65}$ before temperature correction. FIG. 24E shows the relationship of $R_{61}$ versus $R_{65}$ after temperature correction. FIG. 24F shows the relationship of $R_{61}$ versus $R_{65}$ after temperature correction and hematocrit correction. Correction for the temperature effect on $R_{65}$ can be done in many ways. One of such correction methods is by Equation 2:

$$R65\_T = R65 * \exp(TempCo * (25° C. - T)) \qquad (2)$$

where 25° C. is the reference point of temperature; $R_{65}$ is the uncorrected value and $R_{65\_T}$ is the temperature-corrected value, and TempCo is the temperature coefficient in %-change/° C., which is a function of temperature. Based on the existing R65 data, the temperature coefficients of $R_{65}$ are set as follow: if T<12° C., TempCo=−0.0075; if 12° C.≤T<19° C., TempCo=−0.006; if 19° C.≤T<26° C., TempCo=−0.0045; if 26° C.≤T<33° C., TempCo=−0.0015; above 33° C., TempCo=0. There is a small hematocrit effect on $R_{65}$ according to the following relationship: $R_{65\_T}$=−0.00001*$i_{H-4}$+1.0324 where $R_{65\_T}$ is the temperature corrected $R_{65}$ value and $i_{H-4}$ is the ending current of the Hct pulse. The hematocrit effects on $R_{65\_T}$ based on the $i_{H,4}$ values can be corrected to further adjust the $R_{65}$ distribution based on the $R_{65\_T}$ versus $i_{H-4}$ relationship. The relationships of $M_6G_4$ and $R_{61}$ to $R_{65\_TH}$ (after temperature and hematocrit corrections) are shown in FIG. 24C and FIG. 24F respectively.

Figure 25A:
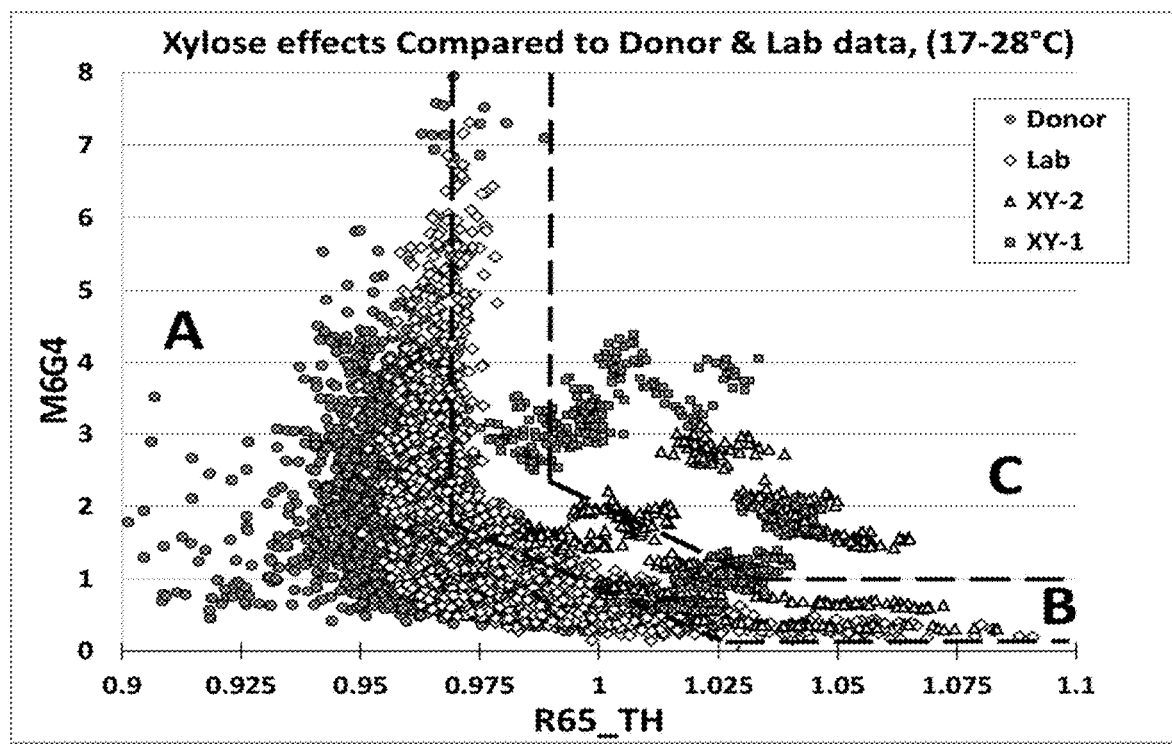
FIG. 25A shows a plot of the sorting and separation of normal and xylose interference data with defined boundaries, in accord with aspects of the present disclosure.

For the xylose interference management, FIG. 25A presents a plot of data sorting and separation between normal data and interference data caused by xylose interference. Three regions of data are shown in FIG. 25A, which include: (A) normal calculation/compensation where the user data (donor study self-testing data) and the lab data tested at 17, 23, and 28° C. dominate, (B) overlap between the lab/donor study data and the low xylose concentration data, and (C) high xylose concentration data. Region B with low xylose concentration can be practically important because this is where xylose interference may occur (MTC~60 mg/dL xylose). A special compensation algorithm can be applied in this region based on the values of $M_6G_4$ and $R_{65\_T}$ of the data points. Higher xylose concentrations are unlikely to occur and they are more readily detected and rejected. An example of the division boundaries can be represented by the first boundary between regions A and B as defined by a vertical line of x=0.9689, a horizontal line of y=0.1, and a line intersecting with the vertical and horizontal lines at y=−30.714*x+31.793, as well as by the second boundary between regions B and C as defined by a vertical line of x=0.99, a horizontal line of y=1.0 and a line intersecting with the vertical and horizontal lines at y=−30.714*x+32.543. Other boundary definitions may be possible depending the data populations of normal and xylose interference data.

Similar divisions and boundary definitions can be applied to the domain of $R_{61}$ versus $R_{65\_TH}$ for the separation of normal and xylose interference data, or the domain of the combined $R_{61}$ and $M_6G_4$ versus $R_{65\_TH}$ or the like. The compensation equation for data in region B follows the methodology of routine multi-variable regression as disclosed in U.S. Pat. No. 9,164,076, filed May 27, 2011, entitled "Slope-Based Compensation Including Secondary Output Signals," U.S. Pat. No. 8,744,776, filed Jun. 6, 2011, entitled "Method for Determining Analyte Concentration Based on Complex Index Functions," International Application No. PCT/US2009/067150, filed Dec. 8, 2009, entitled, "Biosensor System With Signal Adjustment," and International Application No. PCT/US2008/085768, filed Dec. 6, 2008, entitled, "Slope-Based Compensation." using error parameters such as the inter-pulse ratios, intra-pulse ratios, and the likes, each of which is hereby incorporated by reference herein in its entirety.

Figure 25B:
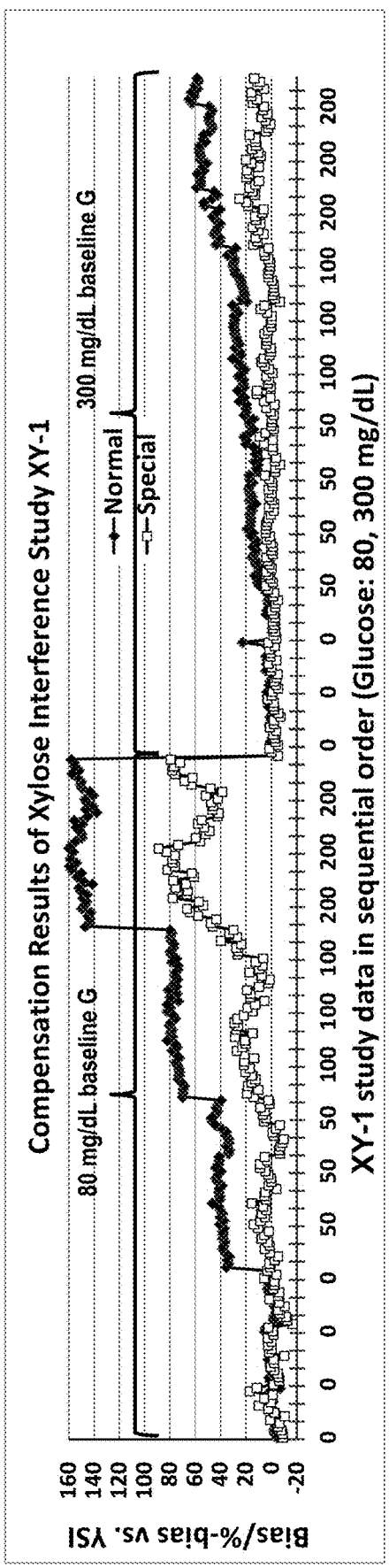
FIG. 25B shows a plot of the compensation results for a xylose interference study (XY-1) where the baseline glucose concentrations are at 80 and 300 mg/dL from left to right of the plot, in accord with aspects of the present disclosure.

FIG. 25B presents the compensation results for xylose interference study XY-1. In this data set, the 100 and 200 mg/dL of the xylose data points with the 80 mg/dL baseline glucose as well as the 200 mg/dL xylose data points with the 300 mg/dL baseline glucose were not in the algorithm regression. The numbers in the x-axis represent the added xylose concentration in mg/dL for each baseline glucose concentration, namely glucose concentrations of 80 mg/dL (data points left of center on the x-axes) and 300 mg/dL (data points right of center on the x-axes), where repeated x-axis values represent multiple data points for the same concentration. It can be seen from the plot that the compensation results with the normal algorithm (not accounting for the xylose effects) gave substantial positive biases as expected. The 50 mg/dL xylose results from the special algorithm gave results that are well within ±15% for 80 and 300 mg/dL baseline glucose. The large biases (~80%) from the 100 mg/dL xylose data points for the 80 mg/dL baseline glucose (not in training) were substantially reduced to ~20%, which may still be subjected to rejections or partial rejections due to the higher $M_6G_4$ values. For the 200 mg/dL xylose data points, they are very likely to be rejected based on the sorting and separation map in FIG. 25A.

Figure 25C:
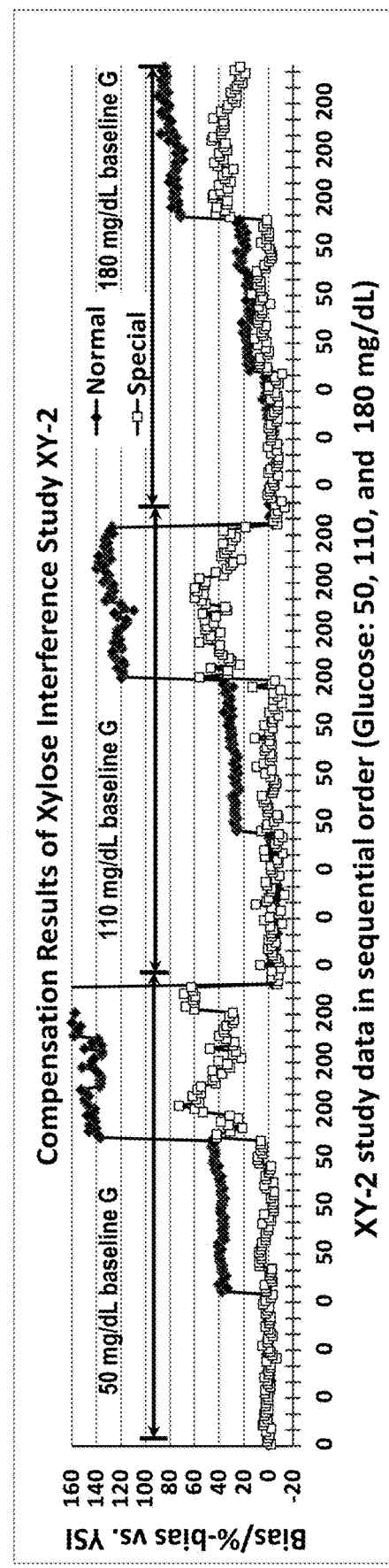
FIG. 25C shows a plot of the compensation results for a xylose interference study (XY-2) where the baseline glucose concentrations are at 50, 110, and 180 mg/dL from left to right of the plot, in accord with aspects of the present disclosure.

FIG. 25C presents the compensation results with the special algorithm to reduce the xylose effects with similar results of bias reduction. This study included three baseline glucose concentrations: 50, 110, and 180 mg/dL, to each of the baseline glucose are added 0, 50, and 200 mg/dL xylose. The data from normal and special compensations are presented in the order of 50, 110, and 180 mg/dL baseline glucose. The positive biases at 50 mg/dL xylose are reduced to the same level as the baseline glucose, while the much higher biases at 200 mg/dL xylose are substantially reduced. The much higher biases at 200 mg/dL xylose are also very likely being detected and rejected according to the method and process outlined in the present disclosure. The numbers in the x-axis represent the added xylose concentration in mg/dL for each baseline glucose concentration, namely glucose concentrations of 50 mg/dL (first grouping of data points on the left), 110 mg/dL (second grouping of data points in the middle), and 180 mg/dL (third grouping of data points on the right), where repeated x-axis values represent multiple data points for the same xylose concentration.

Figure 26:
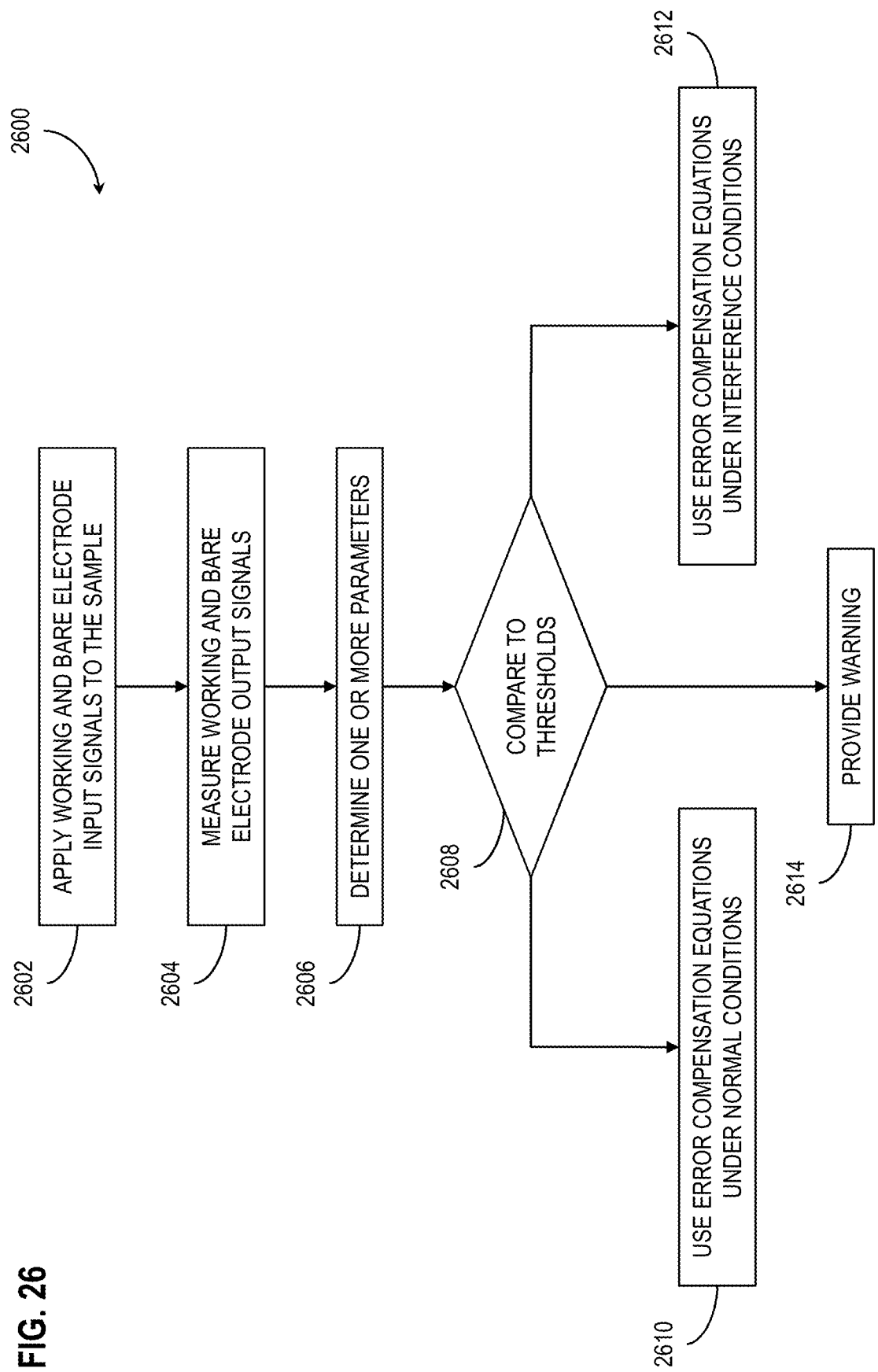
FIG. 26 is a flowchart of a process for determining a concentration of an analyte taking into account the effects of one or more interference species within the sample, in accord with aspects of the present disclosure.

FIG. 26 is a flowchart of a process 2600 for taking into account the effects of one or more interference species within a sample, in accord with aspects of the present disclosure. The process 2600 can be performed by a biosensor system, such as the biosensor system 100 discussed above. Specifically, the biosensor system performing the process 2600 can be a device for determining the concentration of glucose in a blood sample, such as a WB sample.

At step 2602, a first input signal (e.g., working input signal) and a second input signal (e.g., bare input signal) are applied to the sample according to the methods discussed above. Specifically, the working input signal and the bare input signal are applied in a nonconcurrent and intertwined relationship, as described above.

At step 2604, a working output signal and a bare output signal are measured in response to the intertwined working and bare input signals. The measurement of the first output signal and the second output signal occurs as discussed above, such as by a measurement device recording currents responsive to the working and bare output signals.

At step 2606, one or more parameters are calculated based on the bare output signal, the bare output signal relative to the working output signal, or a combination thereof. The one or more parameters that are calculated are related to the working output signal that is attributable to the one or more interference species in the sample. Thus, the one or more parameters can be analyzed to determine the levels of interference in the determination of the concentration of the analyte. The one or more parameters that can be calculated are, for example, $RG_{14}$, $RG_{24}$, and $RG_{34}$, as described above, in addition to other errors parameters, such as $M_6G_4$, $R_{65}$, and $R_{61}$.

At step 2608, the one or more parameters are compared to one or more corresponding thresholds of the parameters to determine the level of interference by the one or more interference species. For example, the parameters of $RG_{14}$, $RG_{24}$, and $RG_{34}$ can be compared to pre-set thresholds that relate the parameters to effects on the determination of the concentration of the analyte, which are attributable to known interferences species and their related concentrations. In some aspects, each parameter can be compared to a single threshold. The single threshold can distinguish between no effect or minimal effect of the interference species on the concentration determination of the analyte and some effect or more than a minimal effect of the interference species on the concentration determination of the analyte. In alternative aspects, each parameter can be compared to more than one threshold. For example, each parameter can be compared to two thresholds (step 2610). The first threshold can distinguish between normal levels of the interference species and elevated levels of the interference species, and the second threshold can distinguish between the elevated levels of the interference species and error levels of the interference species. The error levels may correspond to an error condition of the biosensor system or error levels of the interference species that cannot be accounted for in the determination of the concentration of the analyte. The situation illustrated and described with respect to the process 2600 corresponds to the situation where there are at least two thresholds for the parameters.

After determining that the parameters satisfy the first threshold, such as the parameters being within the pre-set limits of interference species, the biosensor system can proceed under step 2610 with determining the concentration of the analyte under normal conditions. Such a determination under normal conditions can include, for example, using correlations and/or compensation equations, or other methods as described above for determining an analyte concentration, that do not account for, or account for minimal effect, of the one or more interference species on the concentration determination of the analyte.

After determining that the parameters do not satisfy the first threshold but satisfy the second threshold, such as the parameters being above the pre-set limits of interference species but under the error conditions, the biosensor system can proceed under step 2612 with determining the concentration of the analyte under elevated or intermediate conditions. Such a determination under elevated or intermediate conditions can include, for example, using correlations and/or compensation equations, or other methods as described above for determining an analyte concentration, that account for effects of one or more interference species on the concentration determination of the analyte.

After determining that the parameters do not satisfy the first and second thresholds, such as the parameters being above the error condition thresholds, the biosensor system can proceed under step 2614. According to step 2614, the biosensor system can provide a warning to the user. The warning can be a visual, audible, and/or tactile warning indicating that the concentration determination of the analyte is not feasible and/or cannot be relied upon based on the presence of one or more interference species at above error level thresholds. In some aspects, the one or more interference species that are causing the conditions can be identified.

According the foregoing disclosure, intertwined first and second input signals provide benefits over conventional probing of a sample in determining a concentration of an analyte. Based on some of the benefits, the intertwined first and second input signals and associated methods of analysis allow for (1) improved detection and identification of controls; (2) improved information on interference species; (3) improved information for detecting error related to interference species on the working electrode; (4) improved information for error compensation from the working electrode and the bare electrode without chemical reagent; and (5) improved accurate and speed in the assay, such as an assay time of three second or less, while still achieving higher accuracy and precision.

Whole blood sample profiling is another subject of this disclosure. Interference species may be troublesome in the pursuit of better accuracy and interference free analysis. On the contrary, if the interference species, especially the endogenous species can be detected, the combination of determining glucose and reporting one or more endogenous species in one or more parameters or determined concentrations for species such as %-hematocrit, uric acid and cholesterol may provide additional information for the well-being of a person. Thus, a biosensor system for monitoring glucose having a function of WB profiling will enhance the diabetes care management. Specifically, the biosensor system may store the WB profile in terms of their determined concentrations or their reflected parameters along with the WB glucose readings.

Figure 27A:
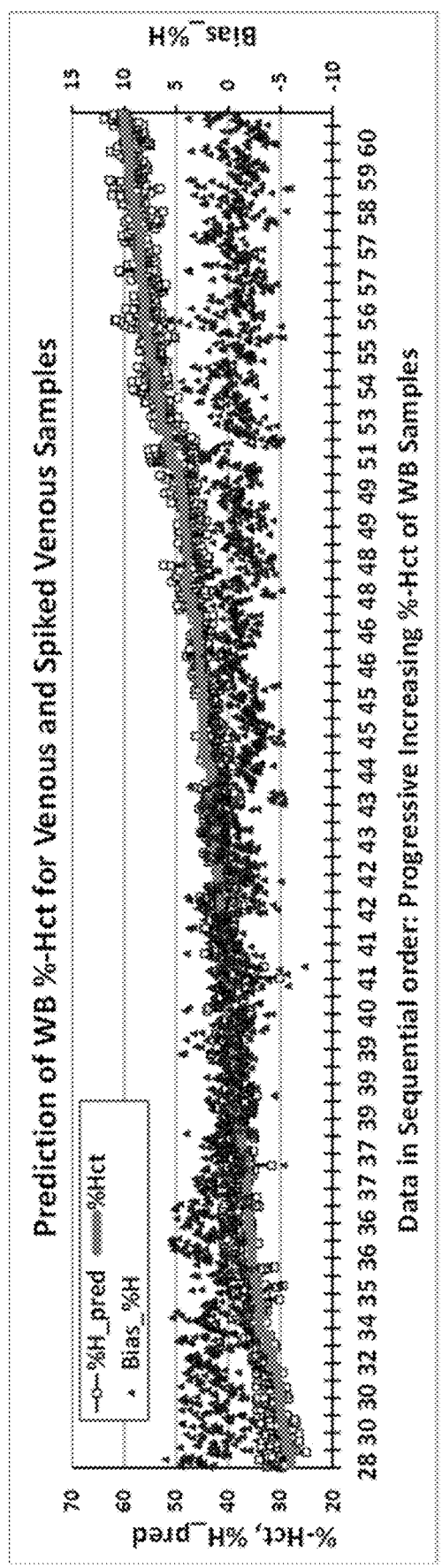
FIG. 27A shows a plot of the prediction of WB %-Hct and the accuracy of the prediction in terms of %-Hct bias, in accord with aspects of the present disclosure.

Detection and determination of the %-Hct can be done with currents from the Hct pulse. With the addition of the second input signals, determination of the %-Hct for a WB sample may be substantially enhanced. FIG. 27A shows a plot of predicted % Hct and the corresponding biases in %-Hct for WB samples. The %-Hct values of these WB samples range from 28 to 60 plotted in the sequential order of increasing %-Hct. The reference %-Hct values and the predicted %-Hct values are shown on the left y-axis while the bias of the predicted %-Hct from the reference %-Hct values are shown in the right y-axis. It can be seen from this plot that the predicted %-Hct tracks well with the reference %-Hct values along the way, with greater than 92% of the data points being within ±3%-Hct (absolute %-Hct bias=% $H_{pred}$-% $Hct_{Ref}$) and greater than 99% being within ±5%-Hct. A simple profiling of a person's WB with glucose and %-Hct values over a period of time will provide a recognized pattern for a particular user where his/her %-Hct values will not change significantly overtime. Occurrence of a sudden change in the %-Hct value may signify that a different user may be using the biosensor system, or that there may be a strip error associated with this particular test.

Figure 27B:
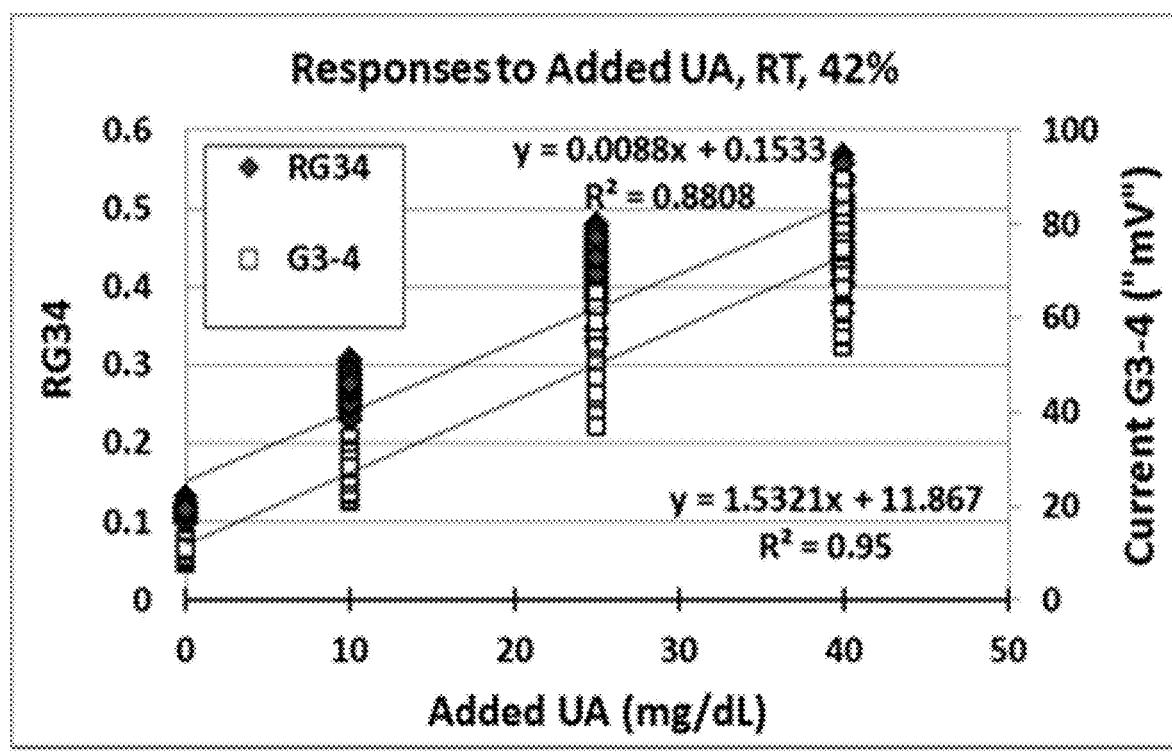
FIG. 27B shows a plot of the responses of the parameter $RG_{34}$ and current $i_{G3,4}$ to added uric acid in WB, in accord with aspects of the present disclosure.

Reporting the determined concentration of endogenous species, such as, for example, %-Hct, UA, and CH, or one or more of their representative parameters, along with the determined glucose value provides a profile of the WB sample for a user. This profiling can provide a long term WB profile of a user, reflecting the progressive change, or lack thereof over time, thus benefiting the diabetes care/management. Uric acid is a waste product that is normally found in the blood when a human body breaks down foods that contain amino acids. High levels of uric acid has been linked to the gout, which is a form of arthritis that causes swelling of the joints, especially in the feet and big toes. Uric acid levels can vary based on gender. According to the Clinical Reference Laboratory (CRL), normal values for women are 2.5 to 7.5 mg/dL and 4.0 to 8.5 mg/dL for men. However, the values may vary based on the lab doing the testing. Recent research indicates that UA may be linked to the onset of diabetes. According to American Diabetes Association, research has shown strong links between UA levels and metabolic syndrome, a combination of medical conditions that are related to insulin resistance (the body's inability to respond to and use the insulin it produces) and increase a person's chances of getting heart disease and diabetes. Studies in people with pre-diabetes and in the elderly have suggested that high UA levels raise a person's chances of getting diabetes. Thus, reporting a determined glucose concentration in a WB sample and the concentration of UA or a parameter related to UA will provide a progressive profile of a person as part of diabetes management. Shown in FIG. 27B is the response to added UA in WB samples. It can be seen from this figure that both parameter the $RG_{34}$ and current $i_{G3,4}$ can be used to show the presence of UA in the blood sample.

While various embodiments of the invention have been described, it will be apparent to those of ordinary skill in the art that other embodiments and implementations are possible within the scope of the invention.

Each of these embodiments, and obvious variations thereof, is contemplated as falling within the spirit and scope of the claimed invention(s), which are set forth in the following claims. Moreover, the present concepts expressly include any and all combinations and sub-combinations of the preceding elements and aspects.

What is claimed is:

1. A method of determining a concentration of an analyte in a sample, the method comprising:
   intertwining a first input signal, via a first electrode having a reagent, with a second input signal, via a second electrode lacking a reagent, the intertwining including:
   applying to the sample, via the first electrode, the first input signal having at least two excitations and a relaxation, and applying to the sample, via the second electrode, the second input signal having at least two excitations and a relaxation, such that the excitations of the first input signal are nonconcurrent with the excitations of the second input signal;
   measuring a first output signal responsive to the first input signal and a second output signal responsive to the second input signal; and
   determining the concentration of the analyte based on at least the first output signal and the second output signal, wherein intensities of the at least two excitations of the second input signal increase over time.

2. The method of claim 1, wherein the second electrode excludes any reagent that facilitates oxidation of the analyte.

3. The method of claim 1, wherein at least one of the at least two excitations of the second input signal is a constant potential excitation, and at least one of the at least two excitations of the second input signal is a linear scan, a cyclic excitation, or an acyclic excitation.

4. The method of claim 1, further comprising:
   determining one or more error parameters based on the second output signal, the second output signal relative to the first output signal, or a combination thereof,
   wherein the determination of the concentration of the analyte is based, at least in part, on the one or more error parameters.

5. The method of claim 1, wherein the second output signal includes at least two responses for one or more excitations of the at least two excitations of the second input signal, further comprising:
   determining at least one error parameter based on the at least two responses for at least one of the one or more excitations of the second input signal,
   wherein the determination of the concentration of the analyte is based, at least in part, on compensating for bias in an analyte concentration correlation based on the at least one error parameter.

6. The method of claim 1, wherein the second output signal includes at least two responses for one or more excitations of the at least two excitations of the second input signal, further comprising:
   determining at least one error parameter based on (i) one of the at least two responses of a first one of the one or more excitations of the at least two excitations of the second input signal and (ii) one of the at least two responses of a second one of the one or more excitations of the at least two excitations of the second plurality of duty cycles,
   wherein the determination of the concentration of the analyte is based, at least in part, on compensating for bias in an analyte concentration correlation in based on the at least one error parameter,
   wherein the at least one error parameter is based on a ratio of (i) the one of the at least two responses of the first one of the one or more excitations of the at least two excitations of the second input signal and (ii) the one of the at least two responses of the second one of the one or more excitations of the at least two excitations of the second input signal.

7. The method of claim 1, wherein the first output signal includes at least one response for one or more excitations of the at least two excitations of the first input signal, and the second output cycle includes at least one response for one or more excitations of the at least two excitations of the second input signal, further comprising:
   determining at least one error parameter based on (i) the at least one response for one of the one or more excitations of the at least one excitation of the first input signal and (ii) the at least one response for one of the one or more excitations of the at least one excitation of the second input signal, wherein the determination of the concentration of the analyte is based, at least in part, on compensating for bias in an analyte concentration correlation based on the at least one error parameter.

8. The method of claim 7, wherein the at least one error parameter is based on a ratio of (i) the at least one response for the one of the one or more excitations of the at least one excitation of the first input signal and (ii) the at least one response for the one of the one or more excitations of the at least one excitation of the second input signal.

9. The method of claim 1, wherein the first output signal is responsive to the concentration of the analyte in the sample, and the second output signal is not responsive to the concentration of the analyte in the sample.

10. The method of claim 1, further comprising:
determining an analyte concentration correlation for the analyte in the sample based on the first output signal; and
compensating for bias in the analyte concentration correlation based on one or more error parameters calculated based on the second output signal, the first output signal relative to the first output signal, or a combination thereof,
wherein the determination of the concentration of the analyte is based on the compensated analyte concentration correlation,
wherein the compensation of the bias includes adjusting the analyte concentration correlation according to a slope deviation value, an intercept deviation value, or a combination thereof.

11. A method of determining a concentration of an analyte in a sample, the method comprising:
intertwining a first input signal, via a first electrode having a reagent, with a second input signal, via a second electrode lacking a reagent, the intertwining including:
applying to the sample, via the first electrode, the first input signal having at least two excitations and a relaxation, and applying to the sample, via the second electrode, the second input signal having at least two excitations and a relaxation, such that the excitations of the first input signal are nonconcurrent with the excitations of the second input signal;
measuring a first output signal responsive to the first input signal and a second output signal responsive to the second input signal; and
determining the concentration of the analyte based on at least the first output signal and the second output signal,
wherein at least one of the at least two excitations of the second input signal is a constant potential excitation, and at least one of the at least two excitations of the second input signal is a linear scan, a cyclic excitation, or an acyclic excitation.

12. The method of claim 11, wherein the second electrode excludes any reagent that facilitates oxidation of the analyte.

13. The method of claim 11, further comprising:
determining one or more error parameters based on the second output signal, the second output signal relative to the first output signal, or a combination thereof,
wherein the determination of the concentration of the analyte is based, at least in part, on the one or more error parameters.

14. The method of claim 11, wherein the second output signal includes at least two responses for one or more excitations of the at least two excitations of the second input signal, further comprising:

determining at least one error parameter based on the at least two responses for at least one of the one or more excitations of the second input signal,
wherein the determination of the concentration of the analyte is based, at least in part, on compensating for bias in an analyte concentration correlation based on the at least one error parameter.

15. The method of claim 11, wherein the second output signal includes at least two responses for one or more excitations of the at least two excitations of the second input signal, further comprising:
determining at least one error parameter based on (i) one of the at least two responses of a first one of the one or more excitations of the at least two excitations of the second input signal and (ii) one of the at least two responses of a second one of the one or more excitations of the at least two excitations of the second plurality of duty cycles,
wherein the determination of the concentration of the analyte is based, at least in part, on compensating for bias in an analyte concentration correlation in based on the at least one error parameter,
wherein the at least one error parameter is based on a ratio of (i) the one of the at least two responses of the first one of the one or more excitations of the at least two excitations of the second input signal and (ii) the one of the at least two responses of the second one of the one or more excitations of the at least two excitations of the second input signal.

16. The method of claim 11, wherein the first output signal includes at least one response for one or more excitations of the at least two excitations of the first input signal, and the second output cycle includes at least one response for one or more excitations of the at least two excitations of the second input signal, further comprising:
determining at least one error parameter based on (i) the at least one response for one of the one or more excitations of the at least one excitation of the first input signal and (ii) the at least one response for one of the one or more excitations of the at least one excitation of the second input signal,
wherein the determination of the concentration of the analyte is based, at least in part, on compensating for bias in an analyte concentration correlation based on the at least one error parameter.

17. The method of claim 16, wherein the at least one error parameter is based on a ratio of (i) the at least one response for the one of the one or more excitations of the at least one excitation of the first input signal and (ii) the at least one response for the one of the one or more excitations of the at least one excitation of the second input signal.

18. The method of claim 11, wherein the first output signal is responsive to the concentration of the analyte in the sample, and the second output signal is not responsive to the concentration of the analyte in the sample.

19. The method of claim 11, further comprising:
determining an analyte concentration correlation for the analyte in the sample based on the first output signal; and
compensating for bias in the analyte concentration correlation based on one or more error parameters calculated based on the second output signal, the first output signal relative to the first output signal, or a combination thereof,
wherein the determination of the concentration of the analyte is based on the compensated analyte concentration correlation, wherein the compensation of the bias includes adjusting the analyte concentration correlation according to a slope deviation value, an intercept deviation value, or a combination thereof.

20. A method of determining a concentration of an analyte in a sample, the method comprising:
  intertwining a first input signal, via a first electrode having a reagent, with a second input signal, via a second electrode lacking a reagent, the intertwining including:
    applying to the sample, via the first electrode, the first input signal having at least two excitations and a relaxation, and applying to the sample, via the second electrode, the second input signal having at least two excitations and a relaxation, such that the excitations of the first input signal are nonconcurrent with the excitations of the second input signal;
  measuring a first output signal responsive to the first input signal and a second output signal responsive to the second input signal; and
  determining the concentration of the analyte based on at least the first output signal and the second output signal, wherein the first output signal is responsive to the concentration of the analyte in the sample, and the second output signal is not responsive to the concentration of the analyte in the sample.

21. The method of claim 20, wherein the second electrode excludes any reagent that facilitates oxidation of the analyte, further comprising:
  determining one or more error parameters based on the second output signal, the second output signal relative to the first output signal, or a combination thereof,
  wherein the determination of the concentration of the analyte is based, at least in part, on the one or more error parameters.

22. The method of claim 20, wherein the second output signal includes at least two responses for one or more excitations of the at least two excitations of the second input signal, further comprising:
  determining at least one error parameter based on the at least two responses for at least one of the one or more excitations of the second input signal,
  wherein the determination of the concentration of the analyte is based, at least in part, on compensating for bias in an analyte concentration correlation based on the at least one error parameter.

23. The method of claim 20, wherein the second output signal includes at least two responses for one or more excitations of the at least two excitations of the second input signal, further comprising:
  determining at least one error parameter based on (i) one of the at least two responses of a first one of the one or more excitations of the at least two excitations of the second input signal and (ii) one of the at least two responses of a second one of the one or more excitations of the at least two excitations of the second plurality of duty cycles,
  wherein the determination of the concentration of the analyte is based, at least in part, on compensating for bias in an analyte concentration correlation in based on the at least one error parameter,
  wherein the at least one error parameter is based on a ratio of (i) the one of the at least two responses of the first one of the one or more excitations of the at least two excitations of the second input signal and (ii) the one of the at least two responses of the second one of the one or more excitations of the at least two excitations of the second input signal.

24. The method of claim 20, wherein the first output signal includes at least one response for one or more excitations of the at least two excitations of the first input signal, and the second output cycle includes at least one response for one or more excitations of the at least two excitations of the second input signal, further comprising:
  determining at least one error parameter based on (i) the at least one response for one of the one or more excitations of the at least one excitation of the first input signal and (ii) the at least one response for one of the one or more excitations of the at least one excitation of the second input signal,
  wherein the determination of the concentration of the analyte is based, at least in part, on compensating for bias in an analyte concentration correlation based on the at least one error parameter.

25. The method of claim 24, wherein the at least one error parameter is based on a ratio of (i) the at least one response for the one of the one or more excitations of the at least one excitation of the first input signal and (ii) the at least one response for the one of the one or more excitations of the at least one excitation of the second input signal.

26. The method of claim 20, further comprising:
  determining an analyte concentration correlation for the analyte in the sample based on the first output signal; and
  compensating for bias in the analyte concentration correlation based on one or more error parameters calculated based on the second output signal, the first output signal relative to the first output signal, or a combination thereof,
  wherein the determination of the concentration of the analyte is based on the compensated analyte concentration correlation,
  wherein the compensation of the bias includes adjusting the analyte concentration correlation according to a slope deviation value, an intercept deviation value, or a combination thereof.

* * * * *